US009727691B2

(12) United States Patent
Ikeda et al.

(10) Patent No.: US 9,727,691 B2
(45) Date of Patent: Aug. 8, 2017

(54) METHOD FOR EVALUATING DRUG SENSITIVITY AND DISEASE VULNERABILITY BY ANALYZING CYCLIC AMP RESPONSIVE ELEMENT BINDING PROTEIN GENE

(71) Applicant: TOKYO METROPOLITAN INSTITUTE OF MEDICAL SCIENCE, Tokyo (JP)

(72) Inventors: Kazutaka Ikeda, Tokyo (JP); Daisuke Nishizawa, Tokyo (JP); Kenichi Fukuda, Tokyo (JP)

(73) Assignee: TOKYO METROPOLITAN INSTITUTE OF MEDICAL SCIENCE

( * ) Notice: Subject to any disclaimer, the term of this patent is extended or adjusted under 35 U.S.C. 154(b) by 0 days.

(21) Appl. No.: 14/347,500

(22) PCT Filed: Oct. 1, 2012

(86) PCT No.: PCT/JP2012/076054
§ 371 (c)(1),
(2) Date: Mar. 26, 2014

(87) PCT Pub. No.: WO2013/047912
PCT Pub. Date: Apr. 4, 2013

(65) Prior Publication Data
US 2014/0243237 A1    Aug. 28, 2014

(30) Foreign Application Priority Data

Sep. 30, 2011   (JP) ................................ 2011-217104

(51) Int. Cl.
*C12Q 1/68* (2006.01)
*G06F 19/18* (2011.01)

(52) U.S. Cl.
CPC ........... *G06F 19/18* (2013.01); *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 2008/0051437 | A1 | 2/2008 | Hallam et al. |
| 2008/0188525 | A1 | 8/2008 | Hallam et al. |
| 2008/0248470 | A1* | 10/2008 | Kim ..................... C12Q 1/6883 435/6.16 |
| 2009/0202565 | A1 | 8/2009 | Labow et al. |

FOREIGN PATENT DOCUMENTS

| EP | 1 731 606 A1 | 12/2006 |
| EP | 2 377 533 A2 | 10/2011 |
| JP | 2002-511850 A | 4/2002 |
| JP | 2008-517627 A | 5/2008 |
| WO | WO 98/48785 A2 | 11/1998 |
| WO | WO 2006/039663 A2 | 4/2006 |
| WO | WO 2007/137181 A2 | 11/2007 |
| WO | WO 2011/133949 A2 | 10/2011 |

OTHER PUBLICATIONS

Hirschhorn et al. Genetics in Medicine. 2002. 4(2): 45-61.*
Hattersley et al. The Lancet. 2005. 366: 1315-1323.*
Lucentini et al The Scientist (2004) vol. 18, p. 20.*
Mummidi et al Journal of Biological Chemistry 2000 vol. 275 No. 25 pp. 18946-18961.*
Halushka et al. Nature. Jul. 1999. 22: 239-247.*
Gagneux et al. Molecular Phylogenetics and Evolution. 2001. 18: 2-13.*
Langdahl et al Journal of Bone and Mineral Research (2000) 15: 402-414.*
Wall et al. Nature Reviews Genetics (2003) 4:587-597.*
Zill et al. Molecular Psychiatry. 2004. 9: 1030-1036.*
Suzuki et al. Eur Arch Psychiatry Clin Neurosci (2001). 251: 57-59.*
Nishizawa et al Molecular Psychiatry. Online Nov. 27, 2012. 19(1): 55-62.*
Maldonado et al Science. 1996. 273: 657.*
NCBI dbSNP database. National Center for Biotechnology Information (Bethesda, MD, USA). Nov. 9, 2006. ss66713294 for rs2952768.*
Zhang et al Anaesthesia. Dec. 2009. 65(2): 130-135.*
Extended European Search Report for Application No. 12837264.6 dated Jun. 1, 2015.
Fillingim, Roger B. et al., "The A118G Single Nucleotide Polymorphism of the μ-Opioid Receptor Gene (OPRM1) is Associated with Pressure Pain Sensitivity in Humans", J. of Pain, vol. 6, No. 3, 2005, pp. 159-167.
Ikeda, Kazutaka et al., "How individual sensitivity to opiates can be predicted by gene analyses", Trends in Pharmacological Sciences, vol. 26, No. 6, 2005, pp. 311-317.
Bokoch et al., "Purification and Properties of the Inhibitory Guanine Nucleotide-binding Regulatory Component of Adenylate Cyclase," J. Biol. Chem. (Mar. 25, 1984), vol. 259, No. 6, pp. 3560-3567.
Chrivia et al., "Phosphorylated CREB binds specifically to the nuclear protein CBP," Nature (Oct. 28, 1993), vol. 365, pp. 855-859.
Gonzalez, G. A. and M. R. Montminy, "Cyclic AMP Stimulates Somatostetin Gene Transcription by Phosphorylation of CREB at Serine 133," Cell (Nov. 17, 1989), vol. 59, pp. 675-680.

(Continued)

*Primary Examiner* — Carla Myers
(74) *Attorney, Agent, or Firm* — Birch, Stewart, Kolasch & Birch, LLP

(57) ABSTRACT

The present invention provides a method for evaluating (predicting, etc.) an individual difference (the tendency of every individual) in terms of drug sensitivity and disease vulnerability, comprising using a gene polymorphism of a cyclic AMP responsive element binding protein gene or the like. The method for evaluating drug sensitivity and the method for evaluating disease vulnerability according to the present invention comprise associating a gene polymorphism of a cyclic AMP responsive element binding protein gene or a haplotype constituted by the gene polymorphism with the drug sensitivity and disease vulnerability of an individual.

10 Claims, 16 Drawing Sheets

(56) References Cited

OTHER PUBLICATIONS

Kasao et al., "Correlation between Oprm1 gene polymorphism and morphine sensitivity in wild-derived inbred mouse strains,"Jpn. J. Neuropsychopharmacol. (2011), vol. 31, pp. 87-85, with English translation.

Kumar et al., "A polymorphism of the CREB binding protein (CREBBP) gene is a risk factor for addiction," Brain Research (2011), vol. 1406, pp. 59-64.

Montminy et al., "Identification of cyclic-AMP-responsive element with the rat somatostatin gene," Proc. Natl. Acad. Sci. USA (Sep. 1986), vol. 83, pp. 6682-6686.

Noda, Y. and T. Nabeshime, "The molecular mechanisms of morphine dependence," J. Clin. and Exp. Med. (Nov. 10, 2001), vol. 199, No. 6, pp. 423-426, with English translation.

Pierce et al., "Seven-Transmembrane Receptors" Nature Reviews—Molecular Cell Biology (Sep. 2002), vol. 3, pp. 639-650.

Communication Pursuant to Rule 164(1) EPC issued Jan. 20, 2015, in European Patent Application No. 12837264.6.

Crisafulli et al., "Case-control association study of 14 variants of CREB1, CREBBP and CREM on diagnosis and treatment outcome in major depressive disorder and bipolar disorder," Psychiatry Research (2012), vol. 198, pp. 39-46.

Dong et al., "Sequence variations of ABCB1, SLC6A2, SLC6A3, SLC6A4, CREB1, CRHR1 and NTRK2: association with major depression and antidepressant response in Mexican-Americans," Molecular Psychiatry (2009) vol. 14, pp. 1105-1118.

Mamdani et al., "Lithium Response and Genetic Variation in the CREB Family of Genes," American Journal of Medical Genetics Part B (Neuropsychiatric Genetics), (2008), vol. 147B, pp. 500-504.

Shi, Michael M., "Enabling Large-Scale Pharmacogenetic Studies by High-Throughput Mutation Detection and Genotyping Technologies," Clinical Chemistry (2001), vol. 47, No. 2, pp. 164-172.

European Search Report issued in European Patent Application No. 12 837 264.6 on Feb. 24, 2016.

Fukuda et al., "Association between OPRM1 gene polymorphisms and fentanyl sensitivity in patients undergoing painful cosmetic surgery", Pain, vol. 147, No. 1-3 (2009) pp. 194-201.

Nishizawa et al., "Genetic polymorphisms and human sensitivity to pain and opioids", MASUI—Japanese Journal of Anesthesiology, vol. 58, No. 9 (2009) pp. 1093-1101.

* cited by examiner

METHOD FOR EVALUATING DRUG SENSITIVITY AND DISEASE VULNERABILITY BY ANALYZING CYCLIC AMP RESPONSIVE ELEMENT BINDING PROTEIN GENE

TECHNICAL FIELD

The present invention relates to a method for evaluating drug sensitivity and disease vulnerability, comprising analyzing a cyclic AMP responsive element binding protein (cAMP responsive element binding protein; CREB) gene. Specifically, the present invention relates to a method for evaluating drug sensitivity and disease vulnerability, comprising associating a gene polymorphism of a CREB gene or a haplotype constituted by the gene polymorphism with the drug sensitivity and disease vulnerability of an individual. More specifically, the present invention relates to a method for evaluating a tendency in the presence or absence of the drug sensitivity and disease vulnerability of an individual, based on the results from the analysis of the above-described gene polymorphism or haplotype.

BACKGROUND ART

Pain is a pathology which is most frequently observed in the medical field, and it is often the case that the pain accompanying a disease is serious for the patient rather than the disease itself. The pain sensation plays an important role in terms of a biological warning system, however, excessive pain would significantly decrease QOL (quality of life) unless it is properly controlled. Recently, the importance of pain control has been recognized, and palliative care including pain therapy has remarkably progressed, and there is a tendency of increasing the frequency and amount of use of various analgesics.

It has been previously known that narcotic analgesics including morphine as a representative example act on a protein known as an "opioid receptor," so as to cause analgesic action. The opioid receptor includes three types of receptors, a μ-type opioid receptor, a δ-type opioid receptor, and a κ-type opioid receptor, and all of these receptors are related to analgesic action. Since these receptors are Gi/o protein-coupled receptors, they activate a GIRK channel and suppression of a calcium channel through the mediation of a Gi-o protein. In addition, the receptors suppress adenylate cyclase (Non Patent Literature 1: Pierce K. et al., Seven-transmembrane receptors, Nat Rev Mol Cell Biol, (2002) 3: 639-650; Non Patent Literature 2: Bokoch G M. et al., Purification and properties of the inhibitory guanine nucleotide-binding regulatory component of adenylate cyclase, J Biol Chem, (1984) 259: 3560-3567). Activation of adenylate cyclase activates cyclic AMP-dependent protein kinase, and it causes activation of a cyclic AMP responsive element binding protein (CREB) through phosphorylation of the serine residue at position 133 of the protein (Non Patent Literature 3: Gonzalez G A. et al., Cyclic AMP stimulates somatostatin gene transcription by phosphorylation of CREB at serine 133, Cell, (1989) 59: 675-680). The activated CREB binds to a CREB-binding protein acting as an activation cofactor (Non Patent Literature 4: Chrivia J C, et al., Phosphorylated CREB binds specifically to the nuclear protein CBP., Nature, (1993) 365: 855-859), and it binds to the cyclic AMP responsive element of genomic DNA, thereby promoting gene expression (Non Patent Literature 5: Montminy M R. et al., Identification of a cyclic-AMP-responsive element within the rat somatostatin gene., Proc Natl Acad Sci USA, (1986) 83: 6682-6686).

SUMMARY OF INVENTION

The objective of the present invention is to provide a method for evaluating (predicting, etc.) an individual difference (the tendency of every individual) in terms of drug sensitivity and disease vulnerability, comprising using a gene polymorphism of a cyclic AMP responsive element binding protein (CREB) gene or the like.

The present inventors focused on the cyclic AMP responsive element binding protein (CREB) gene and conducted extensive examinations based on conventional findings and clinical data. As a result, the inventors identified several useful gene polymorphisms by analyzing the association of each CREB gene polymorphism with sensitivity to drugs such as analgesics, and with disease vulnerability including pain sensitivity. Thereafter, the inventors found linkage disequilibrium among the thus identified gene polymorphisms, and we also revealed a significant correlation between drug sensitivity and disease vulnerability (more specifically, a change in the required administration amount of an analgesic and a change in the threshold value of pain sensitivity due to a difference in specific CREB gene polymorphisms), thereby accomplishing the present invention.

Thus, the present invention relates to the following:

1. A method for evaluating drug sensitivity, comprising associating a gene polymorphism of a cyclic AMP responsive element binding protein gene or a haplotype constituted by the gene polymorphism with an individual drug sensitivity.

The above-described evaluation method includes a method for evaluating a tendency in the presence or absence of an individual drug sensitivity based on the results from the analysis of the gene polymorphism or the haplotype.

2. The method according to 1 above, comprising the following steps: (1) a step of performing linkage disequilibrium analysis and haplotype analysis on a healthy subject and selecting gene polymorphisms in a linkage disequilibrium block; (2) a step of analyzing the association between the genotypes of the gene polymorphisms and drug sensitivity in a test subject; and (3) a step of using the gene polymorphism that has been significantly associated with drug sensitivity in the test subject for evaluation of the drug sensitivity.

3. A method for evaluating disease vulnerability, comprising associating a gene polymorphism of a cyclic AMP responsive element binding protein gene or a haplotype constituted by the gene polymorphism with an individual disease vulnerability.

The above-described evaluation method includes a method for evaluating a tendency in the presence or absence of an individual disease vulnerability is evaluated based on the results from the analysis of the gene polymorphism or the haplotype.

4. The method according to 3 above, comprising the following steps: (1) a step of performing linkage disequilibrium analysis and haplotype analysis on a healthy subject and selecting gene polymorphisms in a linkage disequilibrium block; (2) a step of analyzing the association between the genotypes of the gene polymorphisms and pain sensitivity; and (3) a step of using the gene polymorphism that has been significantly associated with pain sensitivity in the test subject for evaluation of the disease vulnerability.

5. The method according to 3 or 4 above, wherein the disease vulnerability is pain sensitivity or vulnerability to substance dependence (in particular, vulnerability to drug dependence).

6. The method according to any one of 1 to 5 above, wherein the gene polymorphism is at least one selected from the group consisting of a single nucleotide polymorphism, an insertion polymorphism, a deletion polymorphism, and a nucleotide repeat polymorphism.

7. The method according to any one of 1 to 6 above, wherein the gene polymorphism is at least one selected from among: rs16839837, rs2360969, rs10932200, rs2253206, rs2551640, rs11904814, rs16839883, rs6740584, rs3770704, rs2254137, rs2551645, rs2551946, rs4234080, rs2952768, rs2709386, rs7591784, and rs7594560 of a CREB1 subtype gene (which is a CREB1 gene as a subtype of the CREB gene (the same shall apply hereafter); rs1243872, rs2145925, rs2025126, rs1885373, rs1885374, GA007473, rs2295794, rs4879926, GA007477, rs867194, rs11541908, rs741917, rs7862485, rs2756894, rs2249250, rs2295795, rs877365, rs2737273, rs2295797, rs2295798, rs1534847, rs7873822, rs2737274, rs10972567, rs3763630, rs10814274, rs3750434, rs1570246, GA025684, rs1570248, rs1570249, rs34478611, rs1322045, rs1951432, GA025687, rs10814275, rs10758320, rs4878628, rs10758321, and rs10758322 of a CREB3 subtype gene (which is a CREB3 gene as a subtype of the CREB gene (the same shall apply hereafter); rs4722778, rs177479, rs177480, rs11981754, rs177486, rs177498, rs2175738, rs17156579, rs17156603, rs17642145, rs10229500, rs10243659, rs4722785, rs16874503, rs11772815, rs6958133, rs16874525, rs17715174, rs6953524, rs10239810, rs17156649, rs1811248, rs887623, rs740988, rs7794304, rs6952227, rs42695, rs1029897, rs4722793, rs10233653, rs6955105, rs17156685, rs17156694, rs17156699, rs177572, rs177573, rs177574, rs177576, rs13437706, rs177580, rs177581, rs12666636, rs177584, rs177585, rs216715, rs10951197, rs160335, rs1008262, rs310353, rs310359, rs41273, rs1637457, rs17156919, rs41276, rs160375, rs917275, rs41348, rs886816, rs17157048, rs6462098, rs10951201, rs13311248, rs12540480, rs10265166, rs7798774, rs7799246, rs6972081, rs12533079, rs7806547, rs6462100, rs6979352, rs6950574, rs4722835, rs2066979, rs10486591, rs721993, rs2237351, rs3735566, rs11975539, rs6462107, rs2190306, rs4719955, and rs10228137 of a CREB5 subtype gene (which is a CREB5 gene as a subtype of the CREB gene (the same shall apply hereafter); and rs1153711, rs1153702, rs7583431, rs1153699, rs2302663, rs3845744, rs212349, rs212347, rs12693057, rs1153685, rs212360, rs212361, rs2072538, rs1205399, rs1153676, rs7566401, rs7578569, rs3755490, rs13388308, rs11888507, rs10497434, rs268214, rs166531, rs268228, rs268229, rs268230, rs268231, rs10497435, rs1982235, rs268237, rs13030474, and rs268174 of an ATF2 subtype gene (which is an ATF2 gene as an alias of a CREB2 gene that is a subtype of the CREB gene (the same shall apply hereafter)).

8. The method according to any one of 1 to 7 above, wherein the haplotype is at least one selected from the following table.

It is to be noted that haplotypes constituted by a combination of any given number and type of various gene polymorphisms according to 7 above can also be selected as haplotypes used in the evaluation method and the like of the present invention.

TABLE 1

Gene name CREB1
Linkage disequilibrium block No. 1

| Haplotype No. | Gene polymorphism name (※) | | | | | | | | | | | | | | | | |
|---|---|---|---|---|---|---|---|---|---|---|---|---|---|---|---|---|---|
| | 1 Tag | 2 Tag | 3 Tag | 4 | 5 | 6 | 7 | 8 | 9 | 10 | 11 | 12 Tag | 13 Tag | 14 | 15 | 16 | 17 Tag |
| H1 | C | C | C | A | G | G | G | T | C | C | C | C | C | C | A | A | T |
| H2 | C | C | A | G | A | T | A | C | T | A | T | C | C | T | G | G | T |
| H3 | C | T | C | A | G | G | A | T | T | C | C | C | C | C | A | A | T |
| H4 | T | C | A | G | A | T | A | C | T | A | T | C | A | T | G | G | C |
| H5 | C | C | A | G | A | T | A | C | T | A | T | A | C | C | A | A | T |
| H6 | T | C | A | G | A | T | A | C | T | A | T | C | C | T | G | G | T |
| H7 | T | C | A | G | A | T | A | C | T | A | T | C | A | T | G | G | T |
| ... | Haplotypes which are estimated to occur at a frequency of less than 1% | | | | | | | | | | | | | | | | |

(※) 1~17: (in this order)rs16839837, rs2360969, rs10932200, rs2253206, rs2551640, rs11904814, rs16839883, rs6740584, rs3770704, rs2254137, rs2551645, rs2551946, rs4234080, rs2952768, rs2709386, rs7591784 and rs7594560

TABLE 2

Gene name CREB3

Linkage disequilibrium block No. 1
Gene polymorphism name (※)

| Haplotype No. | 1 Tag | 2 Tag | 3 Tag | 4 | 5 | 6 | 7 | 8 | 9 Tag | 10 | 11 Tag | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| H1 | G | C | G | T | A | T | T | T | C | T | C | C | G | C | T | G | T | G | T | C | A | G | G | A |
| H2 | G | C | G | T | A | T | T | T | T | T | C | C | G | C | T | G | T | G | T | C | A | G | G | A |
| H3 | T | T | A | T | A | T | C | T | C | T | T | C | G | A | G | A | C | A | C | C | G | T | G | C |
| H4 | T | T | A | T | A | T | C | T | C | T | C | C | G | A | G | A | C | A | C | C | G | T | G | C |
| H5 | T | C | G | C | C | C | C | C | C | T | C | C | A | A | G | G | C | A | T | C | A | T | A | C |
| H6 | T | T | G | T | A | T | C | T | C | C | C | T | G | A | T | G | C | G | T | C | A | G | G | C |
| H7 | T | C | A | T | A | T | C | T | C | T | T | C | G | A | G | A | C | A | C | C | G | T | G | C |
| ... | Haplotypes which are estimated to occur at a frequency of less than 1% | | | | | | | | | | | | | | | | | | | | | | | |

| Haplotype No. | Linkage disequilibrium block No. 2 Gene polymorphism name (※) | | | | | | | | | | | | | | | |
|---|---|---|---|---|---|---|---|---|---|---|---|---|---|---|---|---|
| | 25 Tag | 26 Tag | 27 | 28 | 29 Tag | 30 | 31 | 32 | 33 | 34 | 35 | 36 Tag | 37 | 38 Tag | 39 Tag | 40 |
| H8 | C | C | G | G | G | C | G | G | A | T | A | C | C | G | C | |
| H9 | C | T | A | T | G | T | A | G | A | G | A | T | C | A | T | |
| H10 | T | C | G | G | C | T | G | A | A | G | A | A | T | C | G | C |

TABLE 2-continued

| | | | | | | Gene name CREB3 | | | | | | | | | |
|---|---|---|---|---|---|---|---|---|---|---|---|---|---|---|---|
| H11 | C | T | A | G | G | T | A | G | A | G | A | A | T | C | G | T |
| H12 | C | C | G | G | C | T | G | A | A | G | A | A | T | C | G | C |
| H13 | C | T | A | T | G | T | A | G | A | G | A | G | T | C | A | T |
| H14 | C | C | G | G | G | C | G | G | G | A | T | A | C | T | G | C |
| ... | | | | | | Haplotypes which are estimated to occur at a frequency of less than 1% | | | | | | | | | |

(X) 1~40: (in this order) rs1243872, rs2145925, rs2025126, rs1885373, rs1885374, GA007473, rs2295794, rs4879926, GA007477, rs867194, rs11541908, rs741917, rs7862485, rs2756894, rs2249250, rs2295795, rs877365, rs2737273, rs2295797, rs2295798, rs1534847, rs7873822, rs2737274, rs10972567, rs3763630, rs10814274, rs3750434, rs1570246, GA025684, rs1670248, rs1570249, rs34478611, rs1322045, rs1951432, GA025687, rs10814275, rs10758320, rs4878628, rs10758321 and rs10758322

TABLE 3

Gene name CREB5

Linkage disequilibrium block No.

| | 1 | | | | 5 | | | | | | 8 | | 9 | | 10 | |
|---|---|---|---|---|---|---|---|---|---|---|---|---|---|---|---|---|

Gene polymorphism name (✗)

| Haplotype (H) No. | 1 Tag | 2 Tag | 3 | 4 | 5 Tag | 6 Tag | 7 Tag | 8 Tag | 9 Tag | 10 Tag | 11 Tag | 12 | 13 Tag | 14 Tag | 15 Tag | 16 Tag | 17 Tag | 18 Tag | H No. |
|---|---|---|---|---|---|---|---|---|---|---|---|---|---|---|---|---|---|---|---|
| H1 | C | T | A | A | G | C | C | C | G | C | A | G | T | G | T | A | G | T | H14 |
| H2 | G | C | G | A | G | T | C | A | A | C | G | G | C | C | C | A | G | G | H15 |
| H3 | G | C | G | A | A | T | C | A | G | C | G | G | C | C | C | G | A | G | H16 |
| H4 | C | C | G | A | G | T | T | A | A | C | A | | | | | | | | ... |
| H5 ... | G | C | G | A | G | C | C | C | A | G | G | | | | | | | | |

Haplotypes which are estimated to occur at a frequency of less than 1%

| | H No. |
|---|---|
| | H11 |
| | H12 |
| | H13 |
| | ... |

Mapping for second group: H No. H6 (row H1), H7 (row H2), H8 (row H3), H9 (row H4), H10 (row H5); then H17, H18, H19 from cols 15-18.

Linkage disequilibrium block No.

| | 11 | | | 12 | | | | 13 | | | | | 15 | | | | 16 | | | |
|---|---|---|---|---|---|---|---|---|---|---|---|---|---|---|---|---|---|---|---|---|

Gene polymorphism name (✗)

| Haplotype (H) No. | 19 Tag | 20 Tag | 21 Tag | 22 Tag | 23 Tag | 24 Tag | 25 Tag | 26 Tag | 27 Tag | 28 Tag | 29 Tag | 30 Tag | 31 Tag | 32 | 33 Tag | H No. |
|---|---|---|---|---|---|---|---|---|---|---|---|---|---|---|---|---|
| H20 | T | A | G | C | C | A | A | G | T | C | C | C | C | G | C | H35 |
| H21 | T | G | G | C | T | G | A | A | C | T | T | C | A | G | C | H36 |
| H22 | C | G | A | C | T | G | G | A | T | T | C | C | A | G | C | H37 |
| H23 | C | A | G | T | T | | | | T | C | T | T | C | A | T | H38 |

H No. column mid: H24, H25, H26, H27 (rows H20–H23); H28, H29, H30, ... (block 12); H31, H32, H33, H34 (block 13).

Haplotypes which are estimated to occur at a frequency of less than 1%

Linkage disequilibrium block No.

| | 25 | | | 26 | | | 27 | | | | | 32 | | | | |
|---|---|---|---|---|---|---|---|---|---|---|---|---|---|---|---|---|

Gene polymorphism name (✗)

| Haplotype (H) No. | 34 Tag | 35 Tag | 36 Tag | 37 Tag | 38 Tag | 39 Tag | 40 Tag | 41 | 42 Tag | 43 Tag | 44 Tag | 45 Tag | 46 Tag | 47 Tag | 48 | 49 | 50 Tag | H No. |
|---|---|---|---|---|---|---|---|---|---|---|---|---|---|---|---|---|---|---|
| H39 | T | A | G | A | G | G | A | A | A | T | C | G | G | G | T | T | T | H49 |
| H40 | C | G | G | A | A | A | G | G | A | T | C | G | T | G | T | C | C | H50 |
| H41 | T | G | A | G | G | A | | | A | T | A | C | C | G | T | C | C | H51 |

H No. (middle column) for rows H39–H41: H42, H43, H44; then H47, H48 (block 27).

TABLE 3-continued

Gene name CREB5

| Haplotype (H) No. | 51 Tag | 52 Tag | 53 Tag | 54 Tag | 55 | 56 | H No. | 57 Tag | 58 Tag | 59 Tag | 60 | 61 | 62 | 63 | 64 |
|---|---|---|---|---|---|---|---|---|---|---|---|---|---|---|---|
| ... | | | | | | | | | | | | | | | |
| | | G | A | C | G | A | H52 | C | T | A | C | T | T | C | C |
| H45 | | | | | | | | | | | | | | | |
| | | G | A | C | G | A | H53 | C | T | A | C | T | T | C | C |
| H46 | | | | | | | | | | | | | | | |
| ... | | | | | | | H54 | A | C | C | G | T | G | T | T |
| | | | | | | | H55 | A | T | A | G | T | G | T | C |

Haplotypes which are estimated to occur at a frequency of less than 1%

Linkage disequilibrium block No. 35

Gene polymorphism name (X̄)

| Haplotype (H) No. | 51 Tag | 52 Tag | 53 Tag | 54 Tag | 55 | 56 | H No. | 57 Tag | 58 Tag | 59 Tag | 60 | 61 | 62 | 63 | 64 |
|---|---|---|---|---|---|---|---|---|---|---|---|---|---|---|---|
| H56 | T | G | G | C | A | A | H61 | C | T | G | G | C | T | T | C |
| H57 | T | A | A | T | G | C | H62 | T | C | A | A | T | C | C | A |
| H58 | G | A | A | C | G | C | H63 | T | T | | | | | | |
| H59 | T | A | G | C | A | A | ... | | | | | | | | |
| H60 | T | A | A | C | G | C | | | | | | | | | |

Haplotypes which are estimated to occur at a frequency of less than 1%

(X̄) 1-64: (in this order) rs4722778, rs4722785, rs1774779, rs177480, rs1774486, rs11981754, rs10229500, rs10229500, rs10243659, rs4722785, rs16874503, rs16874525, rs6958133, rs6953524, rs10239810, rs17156649, rs1811248, rs887623, rs740988, rs6952227, rs42695, rs1029897, rs10233653, rs6956105, rs17156699, rs177572, rs177573, rs177580, rs177581, rs2666636, rs177584, rs17156919, rs1008262, rs310353, rs41273, rs1637457, rs17156919, rs41276, rs160375, rs917275, rs17157048, rs6462098, rs10951201, rs13311248, rs12540480, rs10265166, rs10651166, rs7798774, rs7799246, rs6972081, rs7806547, rs4722835, rs721993, rs2237351, rs11975539, rs6462107, rs2190306, rs4719955 and rs10228137

TABLE 4

Gene name ATF2

Linkage disequilibrium block No. 1

Gene polymorphism name (✕)

| Haplotype No. | 1 Tag | 2 Tag | 3 Tag | 4 Tag | 5 Tag | 6 | 7 | 8 | 9 | 10 | 11 | 11 | 13 | 14 | 15 | 16 |
|---|---|---|---|---|---|---|---|---|---|---|---|---|---|---|---|---|
| H1 | T | C | A | A | G | C | C | A | G | C | G | T | C | A | A | A |
| H2 | G | C | A | G | G | T | T | G | A | T | A | C | A | C | C | G |
| H3 | T | T | C | G | A | T | T | G | A | T | A | C | A | C | C | G |
| H4 | T | T | A | G | A | T | T | G | A | T | A | C | A | C | C | G |
|  |  |  |  | G | G | T | T | G | A | T | A | C | A | C | C | G |
| ... | Haplotypes which are estimated to occur at a frequency of less than 1% | | | | | | | | | | | | | | | |

Linkage disequilibrium block No. 2
Gene polymorphism name (✕)

| Haplotype No. | 17 | 18 | 19 | 20 | 21 Tag | 22 | 23 | 24 | 25 | 26 | 27 | 28 Tag | 29 | 30 | 31 |
|---|---|---|---|---|---|---|---|---|---|---|---|---|---|---|---|
| H5 | C | T | T | C | C | C | G | A | C | A | C | T | T | G | T |
| H6 | T | C | C | T | T | T | A | G | A | C | T | G | C | G | G |
| H7 | T | C | C | T | T | T | A | G | A | C | T | T | C | G | C |
| H8 | T | C | C | T | T | T | A | G | A | C | T | G | C | G | C |
| H9 | T | C | C | T | C | C | G | A | C | A | C | T | T | G | T |
| ... | Haplotypes which are estimated to occur at a frequency of less than 1% | | | | | | | | | | | | | | |

(✕) 1~31: (in this order) rs1153711, rs1153702, rs7583431, rs2302663, rs3845744, s212349, rs212347, rs12693057, rs1153685, rs212360, rs212361, rs2072538, rs1205399, rs1153676, rs7566401, rs7578569, rs3755490, rs13388308, rs11888507, rs10497434, rs268214, rs166531, rs268228, rs268229, rs268230, rs268231, rs10497435, rs1982235, rs268237, rs13030474 and rs268174

9. A method for determining the type, amount, and/or frequency of administration of a drug to be administered to an individual, comprising using the result from the evaluation by the method according to any one of 1 to 8 above as an index.

10. A method for predicting a side effect of a drug to be administered to an individual, comprising using the result from the evaluation by the method according to any one of 1 to 8 above as an index.

11. The method according to any one of 1, 2, 5, 9, and 10 above, wherein the drug is an opioid receptor function modulator and/or a cyclic AMP responsive element binding protein function modulator.

12. The method according to 11 above, wherein the opioid receptor function modulator is at least one selected from the group consisting of methamphetamine, methylenedioxymethamphetamine, amphetamine, dextroamphetamine, dopamine, morphine, DAMGO, codeine, methadone, carfentanil, fentanyl, heroin, cocaine, naloxone, naltrexone, nalorphine, levallorphan, pentazocine, pethidine, buprenorphine, oxycodone, hydrocodone, levorphanol, etorphine, dihydroetorphine, hydromorphone, oxymorphone, tramadol, diclofenac, indomethacin, ethanol, methanol, diethyl ether, propanol, butanol, flupirtine, laughing gas, F3 (1-chloro-1,2,2-trifluorocyclobutane), halothane, estradiol, dithiothreitol, thioridazine, pimozide, fluoxetine, paroxetine, desipramine, imipramine, clomipramine, tetramide, isoflurane, ginsenoside, ifenprodil, bupivacaine, tertiapin, clozapine, haloperidol, SCH23390, and cocaine; and the cyclic AMP responsive element binding protein function modulator is at least one selected from the group consisting of phosphodiesterase 4 (PDE4), calcineurin, protein kinase A, protein kinase C, p90 ribosome S6 kinase 1 (RSK1), calmodulin kinase, glycogen synthase kinase 313, and CREB-regulated transcription coactivator 1 (CRTC1).

13. The method according to any one of 1 to 12 above, comprising using an oligonucleotide consisting of a nucleotide sequence of at least 10 nucleotides comprising the 51$^{st}$ nucleotide of the nucleotide sequence represented by any one of SEQ ID NOS: 1 to 172, or a complementary nucleotide sequence thereto, which can specifically hybridize to a DNA fragment comprising a gene polymorphism of a cyclic AMP responsive element binding protein gene.

14. The method according to 13 above, wherein the oligonucleotide spans a length of 10 to 150 nucleotides.

15. The method according to 13 or 14 above, wherein the oligonucleotide is selected from the group consisting of the nucleotide sequence represented by any one of SEQ ID NOS: 1 to 38 and a complementary nucleotide sequence thereto.

16. A gene polymorphism marker for evaluating a tendency in the presence or absence of an individual drug sensitivity, comprising a gene polymorphism of a cyclic AMP responsive element binding protein gene or a haplotype constituted by the gene polymorphism. Examples of the drug applied herein are the same as those described in 11 and 12 above.

17. A gene polymorphism marker for evaluating a tendency in the presence or absence of an individual disease vulnerability, comprising a gene polymorphism of a cyclic AMP responsive element binding protein gene or a haplotype constituted by the gene polymorphism.

According to the present invention, there can be provided: a gene polymorphism of a cyclic AMP responsive element binding protein gene or a haplotype constituted by the gene polymorphism, which is capable of evaluating an individual difference in terms of drug sensitivity and disease vulnerability; a method for evaluating drug sensitivity and disease vulnerability, comprising using the gene polymorphism or the haplotype; etc. According to this evaluation method, it becomes possible to readily know or predict a proper prescribed amount, a proper prescribed schedule, and the like, associated with a narcotic drug such as morphine, and hence the method is extremely useful for personalized pain therapy, drug dependence therapy and the like.

DESCRIPTION OF EMBODIMENT

Figure 1:
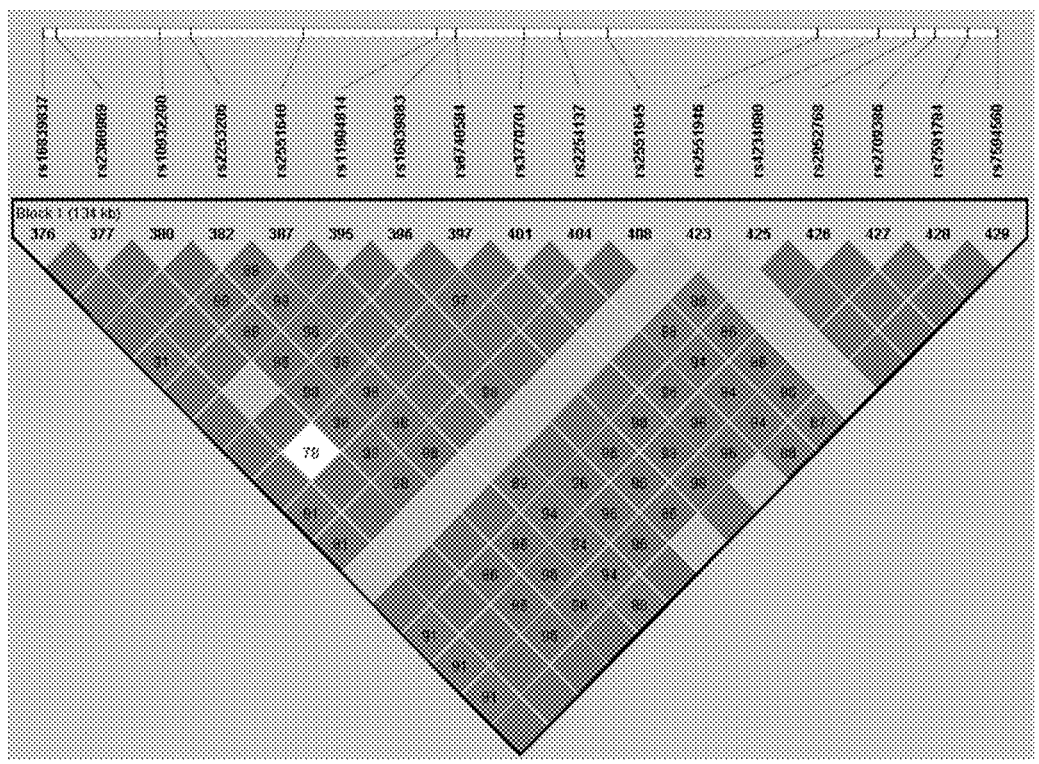
FIG. 1 is a schematic view showing gene polymorphisms identified regarding a CREB1 subtype gene and a linkage disequilibrium found among them. In the figure, high-color squares indicate SNPs showing strong linkage with each other. In addition, the square found at the intersection of squares continued from each SNP to the lower left direction or the lower right direction indicates the calculation value (percentage) of D' that is an index of the linkage disequilibrium of a SNP and another SNP. For example, the calculation value of D' between rs16839837 and rs2551640 is 0.91.

Hereinafter, the present invention will be described in detail. However, the scope of the invention is not limited to the description, and changes and modifications can be made therein without departing from the spirit of the invention other than the following examples.

It is to be noted that the present specification includes all of the contents as disclosed in the specification and/or drawings of Japanese Patent Application No. 2011-217104 (filed on Sep. 30, 2011), which is a priority document of the present application. Moreover, all publications cited in the present specification, including prior art documents and patent literatures such as patent laid-open applications or patent publications, are incorporated herein by reference in their entirety.

1. Outline of the Present Invention
(1) Cyclic AMP Responsive Element Binding Protein Cyclic AMP responsive element binding protein (cAMP responsive element binding protein; CREB) is a protein, which includes a signaling system downstream of G protein-coupled receptor such as a μ-type opioid receptor, is activated depending on an intracellular cyclic AMP concentration, and binds to a cyclic AMP responsive element (cAMP responsive element) of nuclear genomic DNA, so that it is associated with regulation of gene expression. The cyclic AMP responsive element binding protein is present in various tissues and/or organs such as cardiac muscle, various types of smooth muscle, fat cells, skeletal muscle and brain, and it is also associated with neurogenesis, memory, dependence, etc., through the expression of various genes.

Narcotic analgesics including morphine as a representative example act on a protein known as an "opioid receptor," so as to cause analgesic action. The opioid receptor includes three types of receptors, a μ-type opioid receptor, a δ-type opioid receptor, and a κ-type opioid receptor, and all of these receptors are related to analgesic action. Since these receptors are Gi/o protein-coupled receptors, they activate a GIRK channel and suppression of a calcium channel through the mediation of a Gi-o protein. In addition, the receptors suppress adenylate cyclase. Activation of adenylate cyclase activates cyclic AMP-dependent protein kinase, and it causes activation of a cyclic AMP responsive element binding protein (CREB) through phosphorylation of the serine residue at position 133 of the protein. The activated CREB binds to a CREB-binding protein acting as an activation cofactor, and it binds to the cyclic AMP responsive element of genomic DNA, thereby promoting gene expression.

Herein, the cyclic AMP responsive element binding protein will be described. The cyclic AMP responsive element binding protein is distributed in various tissues and/or organs including brain and heart, and plays an important role for neurogenesis, memory, the expression of dependence, etc., through the expression of various types of genes. The cyclic AMP responsive element binding protein has a domain structure comprising a Q-rich domain, a kinase-inducible domain (KID), a basic region/leucine zipper (bZIP), etc. The protein binds to genomic DNA.

The cyclic AMP responsive element binding protein functions as a dimer formed from two subunits. The type of a receptor subtype is broadly classified into CREB1, CREB3, CREB5, ATF2 and the like, and their homologs have also been known. These subtypes are expressed in various tissues and/or organs including brain and heart.

(2) Gene Polymorphism

The present inventors identified gene polymorphisms (such as SNP) of the subtypes CREB1, CREB3, CREB5 and ATF2 (CREB2) capable of constituting a cyclic AMP responsive element binding protein in healthy subjects (FIGS. 1 to 8). Further, a linkage disequilibrium analysis was carried out as needed, and a block exhibiting a strong linkage disequilibrium (a haplotype block) was identified.

Here, the linkage equilibrium means a case where the relationship between two gene polymorphisms on the chromosome is independent, and the linkage disequilibrium means a case where a gene polymorphism is linked to the other gene polymorphism thereby deviating from the equilibrium situation according to Mendel's law of independence. Further, the haplotype means a genetic structure of such as genes or gene polymorphisms located in the vicinity of each other in one allele of a set of alleles (a gene derived from one of the parents).

Gene polymorphisms or the like located in the vicinity on a genome are inherited in a haplotype block. In other words, a haplotype also refers to a combination of the arrangement of the same gene in this haplotype block.

In the case where several gene polymorphisms appear in association with a certain phenotype in the cyclic AMP responsive element binding protein genes, even if not all the respective gene polymorphisms are typed, by analyzing several gene polymorphisms constituting a haplotype, a relationship between the genotype and the phenotype of a patient can be elucidated.

The present inventors analyzed the cyclic AMP responsive element binding protein CREB1 subtype gene, and as a result, they found 4 and 6 gene polymorphisms in the 5' and 3' flanking regions, respectively, and also found 7 gene polymorphisms in the intron region (see Table 5).

In addition, with regard to the CREB3 subtype gene, the inventors found 25 and 14 gene polymorphisms in the 5' and 3' flanking regions, respectively, and also found 1 gene polymorphism in the intron region (see Table 5).

Moreover, with regard to the CREB5 subtype gene, the inventors found 9 and 5 gene polymorphisms in the 5' and 3' flanking regions, respectively, and also found 241 gene polymorphisms in the intron region and 2 gene polymorphisms (rs2190305 and rs3735566) in the noncoding region of exon (see Table 6).

Furthermore, with regard to the ATF2 subtype gene, the inventors found 11 and 6 gene polymorphisms in the 5' and 3' flanking regions, respectively, and also found 16 gene polymorphisms in the intron region and 1 gene polymorphism (rs10497434) in the noncoding region of exon (see Table 5).

According to the present invention, by analyzing gene polymorphisms of the cyclic AMP responsive element binding protein gene or haplotypes constituted by the gene polymorphisms, an individual difference in phenotypes regarding sensitivity to drugs (i.e. drug sensitivity), such as the effectiveness of a drug, the side effects of a drug, and an effective duration of a drug (e.g. the required number of administration of analgesic, the total amount of analgesic, prolongation of stimulant-induced psychosis, etc.), and in phenotypes regarding the development of a disease including pain sensitivity, vulnerability to substance dependence (in particular, vulnerability to drug dependence), etc., can be easily evaluated.

The results of evaluating drug sensitivity and disease vulnerability can be important information for determining the administration number, amount, type or the like of drugs to be administered to an individual, and predicting side effects. Therefore, the present invention provides a method for evaluating drug sensitivity and disease vulnerability based on the results obtained by analyzing gene polymorphisms of the cyclic AMP responsive element binding protein or haplotypes constituted by the gene polymorphisms, and specifically, a method for evaluating (specifically, knowing in advance or predicting) a tendency in the presence or absence of drug sensitivity and disease vulnerability (more specifically, the presence or absence of the genetic factor thereof) in an individual (an individual person). In addition, the present invention also provides a gene polymorphism marker used for evaluating (specifically, knowing in advance or predicting) a tendency in the presence or absence of drug sensitivity and disease vulnerability (more specifically, the presence or absence of the genetic factor thereof) in an individual (an individual person), wherein the gene polymorphism marker comprises gene polymorphisms of the cyclic AMP responsive element binding protein or haplotypes constituted by the gene polymorphisms.

In particular, because morphine, a stimulant or the like may cause a big social problem depending on the usage, it is important to know in advance an appropriate amount of drugs to be administered to an individual before administering the drugs. Therefore, the present invention is extremely useful for personalized pain therapy or drug dependence therapy.

Moreover, according to the present invention, by analyzing gene polymorphisms of the cyclic AMP responsive element binding protein or haplotypes constituted by the gene polymorphisms, an individual difference in terms of dependence-prone personality can be easily evaluated. The results of evaluating dependence-prone personality can be information for determining whether reward dependence is high or low about the personality of an individual. Therefore, the present invention provides a method for evaluating dependence-prone personality based on the results obtained by analyzing gene polymorphisms of the cyclic AMP responsive element binding protein or haplotypes constituted by the gene polymorphisms, and specifically, a method for evaluating (specifically, knowing in advance or predicting) a tendency in the presence or absence of dependence-prone personality (high reward dependence or low reward dependence) (more specifically, the presence or absence of the genetic factor thereof) in an individual (an individual person). In addition, the present invention also provides a gene polymorphism marker used for evaluating (specifically, knowing in advance or predicting) a tendency in the presence or absence of dependence-prone personality (high reward dependence or low reward dependence) (more specifically, the presence or absence of the genetic factor thereof) in an individual (an individual person), wherein the gene polymorphism marker comprises gene polymorphisms of the cyclic AMP responsive element binding protein or haplotypes constituted by the gene polymorphisms. Herein, with regard to the types of a gene polymorphism and a haplotype constituted by the gene polymorphism that can be applied to the above-described evaluation of dependence-prone personality, the same gene polymorphisms and haplotypes as those that can be applied to the above-described method for evaluating drug sensitivity and disease vulnerability can be used. Moreover, with regard to oligonucleotides used for the above described evaluation of dependence-prone personality as well, the same oligonucleotides as those used for the above-described method for evaluating drug sensitivity and disease vulnerability can be used.

Furthermore, according to the present invention, by analyzing gene polymorphisms of the cyclic AMP responsive element binding protein or haplotypes constituted by the gene polymorphisms, an individual difference in terms of the expression level of a CREB1 gene can be easily evaluated. The results of evaluating the expression level of a CREB1 gene can be information for predicting whether the expression level of a CREB1 gene in an individual is high or low. Therefore, the present invention provides a method for evaluating the high or low expression level of a CREB1 gene based on the results obtained by analyzing gene polymorphisms of the cyclic AMP responsive element binding protein or haplotypes constituted by the gene polymorphisms, and specifically, a method for evaluating (specifically, knowing in advance or predicting) a tendency in the presence or absence of the high or low expression level of a CREB1 gene (more specifically, the presence or absence of the genetic factor thereof) in an individual (an individual person). In addition, the present invention also provides a gene polymorphism marker used for evaluating (specifically, knowing in advance or predicting) a tendency in the presence or absence of the high or low expression level of a CREB1 gene (more specifically, the presence or absence of the genetic factor thereof) in an individual (an individual person), wherein the gene polymorphism marker comprises gene polymorphisms of the cyclic AMP responsive element binding protein or haplotypes constituted by the gene polymorphisms. Herein, with regard to the types of a gene polymorphism and a haplotype constituted by the gene polymorphism that can be applied to the above-described evaluation of the high or low expression level of a CREB1 gene, the same gene polymorphisms and haplotypes as those that can be applied to the above-described method for evaluating drug sensitivity and disease vulnerability can be used. Moreover, with regard to oligonucleotides used for the above described evaluation of the high or low expression level of a CREB1 gene as well, the same oligonucleotides as those used for the above-described method for evaluating drug sensitivity and disease vulnerability can be used.

2. Gene Polymorphism of Cyclic AMP Responsive Element Binding Protein Gene

The human cyclic AMP responsive element binding protein gene polymorphisms of the present invention mainly include single nucleotide polymorphisms (hereinafter also referred to as "SNP"), however it is not limited to this, and insertion polymorphisms, deletion polymorphisms, and nucleotide repeat polymorphisms can also be included.

The single nucleotide polymorphism [SNP (SNPs)] means a gene polymorphism caused by substitution of a specific one nucleotide of a gene with another nucleotide. The insertion/deletion polymorphism means a gene polymorphism caused by deletion/insertion of one or more nucleotides.

Further, the nucleotide repeat polymorphism means a gene polymorphism caused by a difference in the number of repeats of nucleotide sequence. The nucleotide repeat polymorphism is divided into a microsatellite polymorphism (the number of nucleotides: about 2 to 4 nucleotides) and a VNTR (variable number of tandem repeat) polymorphism (repeated nucleotides: several to several tens of nucleotides) according to the difference in the number of repeated nucleotides, and the number of repeats varies depending on individuals.

The information of human cyclic AMP responsive element binding protein gene polymorphisms (SNPs in the CREB1 subtype gene, the CREB3 subtype gene, the CREB5 subtype gene and the ATF2 subtype gene observed on the genome of Japanese healthy subjects) elucidated by the present invention is shown in Table 5 and Table 6. The gene polymorphisms shown in Table 5 and Table 6 include the cyclic AMP responsive element binding protein gene polymorphisms of the present invention.

TABLE 5

| | CREB1 gene polymorphism | | | CREB3 gene polymorphism | | | ATF2 gene polymorphism | |
| --- | --- | --- | --- | --- | --- | --- | --- | --- |
| Position | Gene polymorphism name | Major allele: minor allele | Position | Gene polymorphism name | Major allele: minor allele | Position | Gene polymorphism name | Major allele: minor allele |
| 5' Flanking region | rs16839837 | C:T | 5' Flanking region | rs1243872 | G:T | 5' Flanking region | rs268174 | C:T |
| | rs2360969 | C:T | | rs2145925 | C:T | | rs13030474 | G:T |
| | rs10932200 | A:C | | rs2025126 | G:A | | rs268237 | C:T |
| | rs225326 | G:A | | rs1885373 | T:C | | rs1982235 | T:G |
| Intron | rs2551640 | A:G | | rs1885374 | A:C | | rs10497435 | T:C |
| | rs11904814 | T:G | | GA007473 | T:C | | rs268231 | C:A |
| | rs16839883 | A:G | | rs2295794 | T:C | | rs268230 | A:C |
| | rs6740584 | C:T | | rs4879926 | T:C | | rs268229 | G:A |
| | rs3770704 | T:C | | GA007477 | C:T | | rs268228 | A;G |
| | rs2254137 | A:C | | rs867194 | T:C | | rs166531 | T:C |
| | rs2551645 | T:C | | rs11541908 | C:T | | rs268214 | T:C |
| 3' Flanking region | rs2551946 | C:A | | rs741917 | C:T | Exon | rs10497434 | T:C |
| | rs4234080 | C:A | | rs7862485 | G:A | Intron | rs11888507 | C:T |
| | rs2952768 | T:C | | rs2756894 | C:A | | rs13388308 | C:T |
| | rs2709386 | G:A | | rs2249250 | T:G | | rs3755490 | T:C |
| | rs7591784 | G:A | | rs2295795 | G:A | | rs7578569 | G:A |
| | rs7594560 | T:C | | rs877365 | T:C | | rs7566401 | C:A |
| | | | | rs2737273 | G:A | | rs1153676 | C:A |
| | | | | rs2295797 | T:C | | rs1205399 | A:C |
| | | | | rs2295798 | C:T | | rs2072538 | C:T |
| | | | | rs1534847 | A:G | | rs212361 | A:G |
| | | | | rs7873822 | G:T | | rs212360 | T:C |
| | | | | rs2737274 | G:A | | rs1153685 | A:G |
| | | | | rs10972567 | A:C | | rs12693057 | G:A |
| | | | | rs3763630 | C:T | | rs212347 | T:C |
| | | | Intron | rs10814274 | C:T | | rs212349 | T:C |
| | | | 3' Flanking region | rs3750434 | G:A | | rs3845744 | A:G |
| | | | | rs1570246 | G:T | | rs2302663 | G:A |
| | | | | GA025684 | G:C | 3' Flanking region | rs35507277 | T:G |
| | | | | rs1570248 | T:C | | rs1153699 | G:T |
| | | | | rs1570249 | G:A | | rs1153700 | C:G |
| | | | | rs34478611 | G:A | | rs7583431 | A:C |
| | | | | rs1322045 | A:G | | rs1153702 | T:C |
| | | | | rs1951432 | G:A | | rs1153711 | T:G |
| | | | | GA025887 | A:T | | | |
| | | | | rs1081425 | A:G | | | |
| | | | | rs10758320 | T:C | | | |
| | | | | rs4878628 | C:T | | | |
| | | | | rs10758321 | G:A | | | |
| | | | | rs10758322 | C:T | | | |

TABLE 6

| | CREB5 gene polymorphism | | | CREB5 gene polymorphism | | | CREB5 gene polymorphism | |
| --- | --- | --- | --- | --- | --- | --- | --- | --- |
| Position | Gene polymorphism name | Major allele: minor allele | Position | Gene polymorphism name | Major allele: minor allele | Position | Gene polymorphism name | Major allele: minor allele |
| 5' Flanking region | rs4722778 | C:G | Intron | rs177576 | T:C | Intron | rs41320 | C:T |
| | rs177479 | T:C | | rs177578 | G:A | | rs41321 | A:G |
| | rs177480 | A:G | | rs13437706 | C:T | | rs41322 | A:G |
| | rs11981754 | A:G | | rs177580 | C:T | | rs7780656 | G:T |
| | rs177486 | G:A | | rs177581 | C:T | | rs41327 | A:G |
| | rs177498 | C:T | | rs12666636 | C:A | | rs42322 | T:C |
| | rs849322 | A:G | | rs177584 | G:A | | rs41333 | A:G |

TABLE 6-continued

| | CREB5 gene polymorphism | | | CREB5 gene polymorphism | | | CREB5 gene polymorphism | |
| --- | --- | --- | --- | --- | --- | --- | --- | --- |
| Position | Gene polymorphism name | Major allele: minor allele | Position | Gene polymorphism name | Major allele: minor allele | Position | Gene polymorphism name | Major allele: minor allele |
| | rs177505 | T:G | | rs177585 | C:T | | rs9655280 | A:G |
| | rs2175738 | G:A | | rs177588 | G:A | | rs9655281 | G:A |
| Intron | rs4719932 | A:C | | rs6462088 | G:A | | rs4719945 | A:G |
| | rs10258745 | C:T | | rs7796539 | C:T | | rs6945988 | A:G |
| | rs1013900 | G:T | | rs1859020 | A:G | | rs10258405 | T:G |
| | rs6955393 | G:A | | rs1011384 | A:G | | rs10243376 | G:A |
| | rs6953880 | A:G | | rs6462090 | G:T | | rs41334 | T:C |
| | rs17156573 | T:C | | rs12671247 | T:C | | rs10245004 | C:T |
| | rs6960209 | C:T | | rs217508 | T:C | | rs41339 | G:T |
| | rs17156577 | T:C | | rs4719936 | G:T | | rs982947 | C:T |
| | rs7811922 | A:C | | rs217509 | G:T | | rs982950 | A:G |
| | rs6973453 | T:C | | rs217510 | T:C | | rs16874653 | A:G |
| | rs17156579 | C:T | | rs17718257 | G:A | | rs41346 | G:T |
| | rs1073298 | T:C | | rs149591 | C:A | | rs41348 | A:G |
| | rs6961801 | C:T | | rs1910553 | C:A | | rs9969149 | C:T |
| | rs6977728 | C:A | | rs217517 | G:A | | rs6968464 | G:A |
| | rs6978238 | C:T | | rs217519 | G:A | | rs886816 | G:A |
| | rs13230543 | C:A | | rs2391668 | T:G | | rs757980 | A:G |
| | rs12673465 | A:G | | rs4722804 | G:T | | rs41351 | G:A |
| | rs10251129 | T:C | | rs618776 | A:G | | rs9691873 | A:C |
| | rs2391656 | T:C | | rs217503 | C:T | | rs17157048 | A:C |
| | rs6971345 | A:G | | rs217513 | C:T | | rs6462098 | T:C |
| | rs17156603 | A:G | | rs65264 | C:T | | rs10951201 | C:A |
| | rs7806362 | C:A | | rs441355 | G:T | | rs13311248 | G:C |
| | rs17642145 | T:C | | rs2391670 | C:T | | rs12540480 | T:C |
| | rs10229500 | C:T | | rs2391671 | A:G | | rs10265166 | G:T |
| | rs10243659 | C:A | | rs216708 | A:G | | rs7798774 | T:C |
| | rs4722785 | G:A | | rs11980665 | C:T | | rs7799246 | T:C |
| | rs16874503 | C:T | | rs11980669 | C:T | | rs6972081 | T:C |
| | rs11772815 | G:A | | rs11984308 | T:C | | rs7777929 | T:C |
| | rs6958133 | G:A | | rs160346 | G:A | | rs12533079 | T:G |
| | rs16874525 | C:T | | rs150607 | A:G | | rs7806547 | G:A |
| | rs17715174 | G:C | | rs177594 | G:A | | rs6462100 | G:A |
| | rs10242868 | T:G | | rs6969064 | A:G | | rs6979352 | C:T |
| | rs12700884 | G:A | | rs150610 | A:G | | rs6950574 | A:G |
| | rs17156635 | G:A | | rs216715 | T:C | | rs4722835 | A:C |
| | rs10239606 | C:T | | rs10951197 | T:C | | rs9649352 | A:G |
| | rs16874528 | G:A | | rs12539927 | A:G | | rs879593 | A:C |
| | rs7799687 | C:A | | rs216720 | A:G | | rs879591 | G:T |
| | rs714218 | G:A | | rs17156823 | G:A | | rs2299110 | C:T |
| | rs1860759 | A:G | | rs2078980 | G:A | | rs2237349 | C:T |
| | rs997908 | G:A | | rs216730 | T:G | | rs2066979 | T:C |
| | rs12112050 | C:T | | rs13228899 | G:T | | rs10486589 | A:G |
| | rs2191827 | A:G | | rs160335 | G:A | | rs10486591 | G:A |
| | rs4498447 | T:C | | rs10951200 | G:A | | rs6462103 | C:T |
| | rs10254657 | G:A | | rs10486588 | G:A | | rs721993 | C:T |
| | rs6953524 | C:T | | rs216735 | G:A | | rs2237351 | T:C |
| | rs10239810 | A:G | | rs216737 | C:T | | rs740315 | G:A |
| | rs17156649 | G:A | | rs216743 | G:A | | rs2237353 | A:C |
| | rs1811248 | T:G | | rs216744 | A:G | | rs2073537 | T:C |
| | rs887623 | T:C | | rs216747 | C:T | | rs4722844 | G:T |
| | rs740988 | A:G | | rs1976489 | A:G | | rs17730621 | C:T |
| | rs7794304 | T:C | | rs150613 | C:T | | rs2282907 | G:A |
| | rs42694 | A:G | | rs17156878 | G:A | | rs10238623 | G:A |
| | rs6952227 | G:A | | rs767834 | C:G | | rs2299116 | C:A |
| | rs42695 | C:T | | rs4722820 | G:A | | rs2299117 | T:C |
| | rs1029897 | T:C | | rs160337 | C:A | | rs2237355 | A:G |
| | rs42699 | A:C | | rs160338 | G:A | | rs2237360 | T:G |
| | rs4722793 | C:A | | rs1008262 | T:C | | rs2237361 | T:C |
| | rs735101 | T:C | | rs310353 | G:A | | rs2237362 | T:C |
| | rs10233653 | G:A | | rs310359 | T:C | | rs7791555 | G:T |
| | rs6955105 | G:A | | rs310361 | C:T | | rs2237364 | A:G |
| | rs2286841 | C:A | | rs13233942 | A:G | | rs2282909 | T:G |
| | rs979915 | C:T | | rs310338 | T:C | | rs2282910 | C:T |
| | rs7794347 | C:T | | rs41273 | G:A | | rs2282911 | T:C |
| | rs16874562 | G:T | | rs1637457 | A:G | | rs1544470 | A:G |
| | rs17156685 | A:G | | rs17156919 | G:A | | rs1964240 | A:C |
| | rs174024 | C:T | | rs41276 | A:G | | rs17669844 | T:C |
| | rs6949786 | G:A | | rs160375 | A:G | | rs886750 | A:G |
| | rs7793437 | A:G | | rs917275 | A:G | | rs12531253 | G:A |
| | rs3757677 | T:C | | rs160342 | A:G | | rs10951205 | A:G |
| | rs6462085 | T:G | | rs160343 | T:C | Exon | rs2190305 | A:G |
| | rs17717216 | T:C | | rs41295 | C:T | | rs3735566 | G:A |
| | rs17156694 | G:A | | rs160357 | A:G | 3' | rs11975539 | G:A |

TABLE 6-continued

| | CREB5 gene polymorphism | | | CREB5 gene polymorphism | | | CREB5 gene polymorphism | |
|---|---|---|---|---|---|---|---|---|
| Position | Gene polymorphism name | Major allele: minor allele | Position | Gene polymorphism name | Major allele: minor allele | Position | Gene polymorphism name | Major allele: minor allele |
| | rs17156699 | A:G | | rs41298 | G:A | Flanking region | rs6462107 | C:T |
| | rs177572 | T:C | | rs41305 | G:A | | rs2190306 | T:C |
| | rs177573 | T:C | | rs41307 | C:T | | rs4719955 | T:C |
| | rs6977204 | A:G | | rs10228740 | A:G | | rs10228137 | C:A |
| | rs177574 | A:G | | rs3888613 | G:A | | | |

In Table 5 and Table 6, "CREB1" (italic form) indicates a CREB1 subtype gene (a CREB1 gene as a subtype of the cyclic AMP responsive element binding protein (CREB) gene), "CREB3" (italic form) indicates a CREB3 subtype gene (a CREB3 gene as a subtype of the CREB gene), "CREB5" (italic form) indicates a CREB5 subtype gene (a CREB5 gene as a subtype of the CREB gene), and "ATF2" (italic form) indicates an ATF2 subtype gene (an ATF2 gene that is an alias of a CREB2 gene as a subtype of the CREB gene).

"Position" means a position on the genome of a cyclic AMP responsive element binding protein gene, and indicates a 5' flanking region, a 3' flanking region, intron, and exon.

"Gene polymorphism name" is the name of SNP at a position on the genome, and it has been registered in the dbSNP database (which is accessible from the NCBI website dbSNP Short Genetic Variations) (the same shall apply in the present specification). Basically, the ID "rs" is given before four or more digit numbers, so that the type of SNP can be identified.

"Major allele" indicates an allele occurring in the majority of the genomes of Japanese healthy subjects, and "minor allele" indicates an allele occurring in the minority of the genomes of Japanese healthy subjects.

In the present invention, a method of obtaining gene polymorphism information is as follows, for example.
(1) Genomic DNA is purified from a blood specimen collected from a human using the phenol method and the like. At this time, a commercially available genomic DNA extraction kit such as GFX Genomic Blood DNA Purification Kit (manufactured by GE Healthcare Bio-Sciences KK) or a device may be used.
(2) Then, the obtained genomic DNA is dissolved in TF buffer (10 mM Tris-HCl, 1 mM EDTA, pH 8.0) and the concentration of the obtained solution is adjusted to 100 ng/μl.
(3) Total genome genotyping is carried out by an infinium assay II method or the like, using iScan system (manufactured by Illumina, San Diego, Calif.), in accordance with the protocols provided by the manufacturer.
(4) Total genome genotyping data are analyzed using BeadStudio Genotyping module v3.3.7 (Illumina) or the like, and the quality of gene polymorphism data of each sample is evaluated (quality control).
(5) Based on these total genome genotyping data, gene polymorphism included in the gene regions and flanking regions of a gene of interest are selected, using the annotation information of the name of the gene of interest as a key, and all information regarding such gene polymorphisms is extracted using an output function of BeadStudio Genotyping module v3.3.7 (Illumina) or the like.

The present invention provides an oligonucleotide, which contains any one of CREB1 subtype gene polymorphisms (rs16839837, rs2360969, rs10932200, rs2253206, rs2551640, rs11904814, rs16839883, rs6740584, rs3770704, rs2254137, rs2551645, rs2551946, rs4234080, rs2952768, rs2709386, rs7591784 and rs7594560), CREB3 subtype gene polymorphisms (rs1243872, rs2145925, rs2025126, rs1885373, rs1885374, GA007473, rs2295794, rs4879926, GA007477, rs867194, rs11541908, rs741917, rs7862485, rs2756894, rs2249250, rs2295795, rs877365, rs2737273, rs2295797, rs2295798, rs1534847, rs7873822, rs2737274, rs10972567, rs3763630, rs10814274, rs3750434, rs1570246, GA025684, rs1570248, rs1570249, rs34478611, rs1322045, rs1951432, GA025687, rs10814275, rs10758320, rs4878628, rs10758321 and rs10758322), CREB5 subtype gene polymorphisms (rs4722778, rs177479, rs177480, rs11981754, rs177486, rs177498, rs2175738, rs17156579, rs17156603, rs17642145, rs10229500, rs10243659, rs4722785, rs16874503, rs11772815, rs6958133, rs16874525, rs17715174, rs6953524, rs10239810, rs17156649, rs1811248, rs887623, rs740988, rs7794304, rs6952227, rs42695, rs1029897, rs4722793, rs10233653, rs6955105, rs17156685, rs17156694, rs17156699, rs177572, rs177573, rs177574, rs177576, rs13437706, rs177580, rs177581, rs12666636, rs177584, rs177585, rs216715, rs10951197, rs160335, rs1008262, rs310353, rs310359, rs41273, rs1637457, rs17156919, rs41276, rs160375, rs917275, rs41348, rs886816, rs17157048, rs6462098, rs10951201, rs13311248, rs12540480, rs10265166, rs7798774, rs7799246, rs6972081, rs12533079, rs7806547, rs6462100, rs6979352, rs6950574, rs4722835, rs2066979, rs10486591, rs721993, rs2237351, rs3735566, rs11975539, rs6462107, rs2190306, rs4719955 and rs10228137), and ATF2 subtype gene polymorphisms (rs1153711, rs1153702, rs7583431, rs1153699, rs2302663, rs3845744, rs212349, rs212347, rs12693057, rs1153685, rs212360, rs212361, rs2072538, rs1205399, rs1153676, rs7566401, rs7578569, rs3755490, rs13388308, rs11888507, rs10497434, rs268214, rs166531, rs268228, rs268229, rs268230, rs268231, rs10497435, rs1982235, rs268237, rs13030474 and rs268174), and which is capable of being specifically hybridized to a DNA fragment containing a gene polymorphism of the cyclic AMP responsive element binding protein gene. The gene polymorphic site is the 51$^{st}$ nucleotide in the nucleotide sequence represented by any one of SEQ ID NOS: 1 to 172.

It is preferred that the oligonucleotide of the present invention has at least 10 nucleotides, preferably 10 to 150 nucleotides, more preferably 10 to 45 nucleotides, further more preferably 14 to 25 nucleotides.

Examples of the oligonucleotide of the present invention include oligonucleotides having a nucleotide sequence represented by any one of SEQ ID NOS: 1 to 172 containing the above-mentioned gene polymorphism of the cyclic AMP responsive element binding protein gene or a nucleotide sequence complementary to the nucleotide sequence (Tables 7 to 10).

The oligonucleotides of the present invention can be used as a probe or a primer specific to a cyclic AMP responsive element binding protein gene in the detection of cyclic AMP responsive element binding protein gene polymorphism described in the below-mentioned 6.

TABLE 7

| Gene name | Position | Gene polymorphism name | Sequence | SEQ ID NO: |
|---|---|---|---|---|
| CREB1 | 5' Flanking region | rs16839837 | ATTTAAAGAAGACCAGCAGAAAAATATTTATGAACTTATTTTCAACTTGT[T/C]CCCATTTTTGAACTTTTTTATCAGTGAAGAAATGGAAACATTTTTTCAAT | 1 |
| | | rs2360969 | ATGAAAAATTGGGGATGAGGGCCAGTCATCTGTATTTCAACAAGTCTTGC[T/C]GGTGATTCCGATGCACGCCATAGCGTGAGAACCAGTATAGCAATAAAACC | 2 |
| | | rs10932200 | AATAGGGAGAGCAAAAGAGCAAAGAGGTGGTTGTTCGGTGATCAATTTCC[A/C]CCAGAGTAGTAAGGAAAGGCCTCACAGAAACAGGAGCATTTGAGCAAAGA | 3 |
| | | rs2253206 | ACAAATAATGAGAAGTAGGAATTGGAAAAGAAAGTGATAACTTACAGTTA[A/C]GTAGGAGGAATGGGTGACAGAAAAAAAATTCCAGGGGAAGGGAAGGGCATG | 4 |
| | Intron | ts2251640 | TTATAATACCTTATACAGTGCCTGCCCATCACTTGACTCTTATGGGTTCA[A/C]CATAGGAGTCAGCATGCAGCAAATTCAAGCTTTACTTCTGGGACTTGGGG | 5 |
| | | rs11904814 | AAGATAGTGTTGTGCATGTAAAGATCTAAGAACTTGATATTTCTATGAAA[T/G]CACAATGACTGAGCAATAGTCCTTTGCCTTAGTTTTTATTCCATTGAGTG | 6 |
| | | rs16839883 | CGAGGGATAGTACTTAAGTTTCCAAAGGACCATATATAGGTTTAGGAAAC[A/C]TCAATATTACCATTGTTTTGATTGGTTCTAGTTACTTTATAGTTTATTT | 7 |
| | | rs6740584 | GTACTTAAGTTTCCAAAGGACCATATATAGGTTTAGGAAACATCGAATAT[T/C]ACCATTGTTTTGATTGGTTCTAGTTACTTTATAGTTTATTTTAAAATTTC | 8 |
| | | rs3770704 | AAAATTTAATTTAAAAATTAGATGATTTATTTGGAAGAAGCATTTTTAGA[T/C]AGGTGGCAATATCCTCTCTAGACAATTCTCCCTGTAGGGGTCAAGCTTTT | 9 |
| | | rs2254137 | AAACCTTTAACTTAAAATTAGAAGGAAGTGTGATGAAGAAGTCTCAACCA[A/C]AGGCTGAGTAGTAATATTTAAGACAACACTGCTTACTAAAGAAAAGAGTT | 10 |
| | | rs2551645 | AGGTCATATGTACTAAAACAGTTTATCCAAAAAGGGCTTTCTAAGACACA[T/C]TATTTTCAAACTCAAAAGTCAAAAACAAAGAAAAAATTCTTATGGAACCA | 11 |
| | 3' Flanking region | rs2551946 | GTGTTTATGTAATACATATATAATCACTGAAAAATTACTGAATTGTATGA[A/C]AGTAATGTAAGTGAAAATACTTGTTCTTTAAGTGGTAAGTTAAAGTTGTT | 12 |
| | | rs4234080 | ATTTCTGCAACCCAAATTCCGTGGTCTCCTCATAGGGCACGAGGGCCATT[A/C]CGCCTGCACCCCGCCCTCTGCTCAGACCTGCCGTGCAAAAGAATCCTGGG | 13 |
| | | rs2952768 | CTCTGTCTCAAAAAAAAAAAAAATAGTGCTTTTTACTTTTATCTGAATGA[T/C]TGAAATGTCCTTTTCCCAATCCTATGATGCCTGACTGCAAAATAATGGTA | 14 |
| | | rs2709386 | AACACTGACTTCCTATCACTGACTGTAAATATACAACTGATACATTATCA[A/G]TTTTCTTGTTATCTTTAACGTGAAAGCAGTATAGAGAGAGTGTGTTCAAA | 15 |
| | | rs7591784 | CTGGCTGTCCAGTCCCCACTCCACACCACAGAGCAACACCTAGCCAAAGA[A/G]GGTAGGTAAGAAAAGCTAAACACCCAGGGATATGAAACCAGCCTTCACAG | 16 |
| | | rs7594560 | TGGCAATTTTTGAATAAAAAGATTAACTACTAATTCTGAGGCAGTGGAGA[T/C]TGAGGAGAATAAGAAAGATGGCCAGCACTGCTTGCTTCTCTGGCTGTCCA | 17 |

TABLE 8

| Gene name | Position | Gene polymorphism name | Sequence | SEQ ID NO: |
|---|---|---|---|---|
| Gene name | 5' Flanking region | rs1243872 | AGTCCTCCTGTTCCCTGTGAGAGCACTTCAAGTGCTGGGGCCAGGTCTGA[T/G]GCAGCTCTGATTCCTACACAGCAAAGCCTGGCCCAGGTAAGGGGATGGGA | 18 |
| Gene name | | rs2145925 | GGAGACGCGGTGTGTGTAGGGGCGCTACTAAGATTTGGAGGCTACTGGGA[T/C]GGAAGCGGAATAACATAAAAGGGACAGTACAGTCAAGGGTACTGGTGGGA | 19 |
| Gene name | | rs2025126 | GTTGCCAACCTAAGACGACTGTCAGAGAGTCCATGCATTATGGACAGAGT[A/G]GCTGGATGGGGACGTGGAAGCACACAGCATCCACCTCTCTGACTGCCTCT | 20 |
| Gene name | | rs1885373 | CCCCCTCTAACAATAAATTCTCACACCTGGGTCAAGCTCTTCACTTTTAG[T/C]GCTACCCTAGGCAGGAGTGTCCCAACCCAATCAAGAGCGGTGCCTACCCG | 21 |
| Gene name | | rs1885374 | AATGTCCTGGTAGCCACAAGGAACTGTGGTAGCTGCTGTCCCAGCAGCAG[A/C]AGAACGACACTTTGTGAGGCTTAGGTGCTGGCCAGGGAGGTGAGGATAAC | 22 |
| Gene name | | GA007473 | GATAGTATCAAAAAACGGTGAAGAGAGCTGATGAGGCTGTGGGGACTGGC[T/C]GGAAGCTGCTGGCAGGGTGGAGTGGGCTGGGGCCCCGGCAGATTCAGATC | 23 |
| Gene name | | rs2295794 | AGCTTTAGGCCCCGCAGATCCCTACAGTTTCTCTCCCACTATGTTCTGGC[T/C]CAAAGCTGCCTCACGGAAATGCCTCAAGGATTTCTACCTTGCAAGCCCGA | 24 |
| Gene name | | rs4879926 | GAACTTGGACTTTTACATAATATGTGAAAGTCATAAAATATTTTGATGTA[T/C]GGGTTCAATCTGCAAACATTTATTAAAGATCAGCTAGGTGGCAGATTCTA | 25 |
| Gene name | | GA007477 | CTCCCAGCTGCGTTTTGCACCAGGACCTTGGTGTCCTCCACCAGCACCTT[T/C]GCAGTCTTCAGGATGCCCTCCCTGAGGGAGGGCCCAGCTTAGTCAGATCT | 26 |
| Gene name | | rs867194 | CATAACCCCATACAGGCCACATGGTAATCCACGGCCCTCTGATTCCCACA[T/C]TCAAGCATAAAGTGCTCCTCCCCTTCTCCCCACTGTGCTTAACACAATCC | 27 |
| Gene name | | rs11541908 | GTGGATTACCAAACAACTATGGTGCGGACAGCCAAGGCCATTGCAGTGAC[T/C]GTTCAGGAGATGGTGAGTTTGGGCGAGTCCCAGAGGACTGCCCTCGGAGA | 28 |
| Gene name | | rs741917 | TGCCCATCCTCCATTCTGCCACAATGTATGCCCCCCAGCCACACTGGTTC[T/C]CCATCCCTCAATACCTCATGCTTGTAATTAGCTTCTTGATGGAGTCTGAG | 29 |
| Gene name | | rs7862485 | CAGAGATACCCAAAGATGAACTGGGCATGGGAGAGGAAAGACATACTAAT[A/G]GAGAAACCATAAGAGGGCATGTGGGAGAGTAAGCTCGAACATCTACAGAG | 30 |
| Gene name | | rs2756894 | ATGTTGGGTCTTAGAGTGAAAAGTATGGCTTACTGTAAGTAGCAGTAAAA[A/C]GTTTGAGAGCCATATATAAATACACACCTTTGTGCACACAAGCAAAGCCT | 31 |
| Gene name | | rs2249250 | GAGCTTCTTGAAATGTCCCAGTGCTAGGAGGAAGCTGCAAGGTGAGAGGG[T/G]AAGTCAGACAGAAGAGTGGGGAATGATGCAGGGAGAAGTCTGGTAAAGGA | 32 |
| Gene name | | rs2295795 | CTGGCATTCTTTGACTCCTACGTTCCCCCACCCCCTACCGTCCTCCTACC[A/G]AGTCACTCAGGAGTCGCTTGCTGGCATCTCCAACTGCCCTCAGGGCATTA | 33 |
| Gene name | | rs877365 | CCAGCTCCCATTTTCCTACCTCCCTCACAATATGCCCCATGCCTGGCTCT[T/C]TGCCCACATACCTGCATAATTCTCATTGCCCTGGGCAACCTCTCCCAGTA | 34 |
| Gene name | | rs2737273 | CCTCCCGAAGTGTTAGGATTGCAGGCATGAGCCACCACACCTGGCCTAAA[A/G]TTATTTTTTAATTGACATAATTTTACATATTCATGAGGTACATAGTGACA | 35 |
| Gene name | | rs2295797 | ATGGGGAAGAATTTAGCAAAGAGTTTCATATCACAGCTAAGGAATTAAGG[T/C]TGGATGCTAACTCTAACGAGAGAGAATTATGGGGACACTGGAAAGGTTGA | 36 |

TABLE 8-continued

| Gene name | Position | Gene polymorphism name | Sequence | SEQ ID NO: |
|---|---|---|---|---|
| Gene name | | rs2295798 | TCAGATTATGCTACCTCATTTGATCCTATCAGTCCTACACGGGGCAAGTA[T/C]TGTTATCCCAAATCAGAGGTAAATAAAAGATTACAAGAATATTGAACTGA | 37 |
| Gene name | | rs1534847 | ATGTAGTTCAGTATCTCTGCCCCTACCCCCATCTCTGAAGCAAGCATGTC[A/G]CTCTTTTTTGAGATTATCTGAAGAATTTTGCTGCAGTAGCCAGAGGGAAA | 38 |
| Gene name | | rs7873822 | TTATCTGGTCAACTCTTGTGTTTTGGAGAAGGGGAAATAGACTCTGGGAG[T/G]CCAGGAAACATTTTCAAGACAGGCCAGAGAAAGGACCCAGTCCCTGTAAC | 39 |
| Gene name | | rs2737274 | TCTCACCAGAGGCTTCCGTGCTTGAGGAGGAAGGGGGTGTCTAAGTGTCC[A/G]GAGGAAATGGGGGGAGACATGCAGTTTCAGCTTAGTGTGAAGGGTCCTTT | 40 |
| Gene name | | rs10972567 | ACAAGTATGAGTAGAAGCTAGCTCATTCCTCCTTTGGCCTGAGAACTTTG[A/C]TCCCTTTTCCATTGTGTTTGATGGAACAGCAACTCCCCACTGCCGTGTCC | 41 |
| Gene name | | rs3763630 | GGTCCCTATTTCCCACCTATGTTGTCTGTAAACAACACAGTCCAGAATCT[T/C]TGTCCCCTAACTGTGGTGGCCACAGCAAGGGCCTTGGGCTTAGAGAATGG | 42 |
| Gene name | Intron | rs10814274 | TTTTTTTAATAGTTTAAAATGGTCTGGCTTGTTAGGGTTAACACCTGGTC[T/C]GTGGAGGCATTCAGAAAGAATCTGAATGCCTGTTGGTCAGGGAAGCTGTA | 43 |
| Gene name | 3' Flanking region | rs3750434 | AAGGAACATGTACCTCCCAAGATGGAAAGGATTTGGGGGTTCAGCAGAGT[A/G]GGATCATCAAATGAATCCCAGTGCAAGTCTACTGACTTTGGTGGGTGGAG | 44 |
| Gene name | | rs1570246 | ATTCCAGATGCGGGCGCCGGTCGTTGTTAGGTATCGTCCCGGAGGGCCGG[T/G]CGTTGGGGAAAGCTTAAATGAGCTGGTGTTTCAGTGGAGCCGGGGAGCTC | 45 |
| Gene name | | GA025684 | TTGGCTGGGGAGGCGCTGGAGTGTGTAGTGACCGTCACCAACCCCCTTCC[C/G]CCCACGGCCACTTCTGCATCCAGGTGGGGATGCTGGCACTGAAGGTGGTG | 46 |
| Gene name | | rs1570248 | TTTAGCCATCTCATGTTAGAATCTAAAACCCTAACCTCTACTCTCATCTC[T/C]GTTCCCTCTCAGCATTACCTCTCCACTCATTCTTTCTCTAGGCCTTCAGG | 47 |
| Gene name | | rs1570249 | GAGGGTGTAATGGATCCTGATTCCTTATACACACTCCCAGACATACCCAC[A/G]TCTAGCCTCTGACCCGGAACAGTTTCTCAGACCTTCAACCTCTTCCTGTT | 48 |
| Gene name | | rs34478611 | AGTACGCACTATCCCCGTATTTAGTTTGTCTTTCCTGTTTCACAGCTGGA[A/G]GAAGCCTGGGTATTTTGACACGGGATCATCTGTAAGGCCCCATCCTCCCT | 49 |
| Gene name | | rs1322045 | TGGAGGGGGCACTGGACTGGGCACTTCCCCAGCAAGGAGGCAGGAGGGGC[A/G]AGGGCCCCCAGGTGGTCCCCAGATCTCTTCCCTGACCTGGAGAGAAGGAA | 50 |
| Gene name | | rs1951432 | CTGGCGCGCAGGTCCCGGAGGGGGCGGCTGGCGCGCACTACACGCTTGGG[A/G]ACAAGGAAAACATCCGCCGGAGGCCCGGCCGGGCGGCGCTCCAGCCTCGG | 51 |
| Gene name | | GA025687 | GTCGTGGTGTCGCTACGGGCGCGAAACGGACACTGAACACAGTCTGACTG[A/T]ATGGAGGCAGGTGGGGAGGGATCCCCTGGGAGAACTTGGCGGGCCGAGAG | 52 |
| Gene name | | rs10814275 | TGCATTGCCTTTGGTCCCAAACAAGCAAATCTGGGTCAATTAATGAAAAA[A/G]AAAGAAAAGAAAAGAAAATGTCTTACTTTGGGCCCTGTTGCACTCTCCC | 53 |
| Gene name | | rs10758320 | TTGGATAACAAATTAACCTCCATTTCCACTGGACAGAGAACTCATTCTTC[T/C]GGTATGTTTCAGAAGGCTAATGGAGCAAGGATAACCTTATATTACTAATG | 54 |
| Gene name | | rs4878628 | TGGCTAGTGTTTTTGTATCCTGCATAAGAAATCTTCCCTTACACCAGGT[T/C]ACAAAGATTTTTTCCTACATTTTCTCCTATATCTAAAAGTTTTATGATT | 55 |

TABLE 8-continued

| Gene name | Position | Gene polymorphism name | Sequence | SEQ ID NO: |
|---|---|---|---|---|
| Gene name | | rs10758321 | AGACATCATTAAATTCATCATGGCATTCTTTCTTGCTGAGCCTGGACATA[A/G]CCTGGTAAGACTAGAACTAGATAATAGGAAAAGAAATGTAGACATTAAGT | 56 |
| Gene name | | rs10758322 | TGGGAGAGGCTGGCATCAAATTACTCCTCTGTTTTTCTCTCTTGGTGACC[T/C]AGCAGGTGTTTAGGACAATGACGACTACTCATGTGGAACCTTTGCAGTCA | 57 |

TABLE 9

| Gene name | Position | Gene polymorphism name | Sequence | SEQ ID NO: |
|---|---|---|---|---|
| CREB5 | 5' Flanking region | rs4722778 | AATCACCATTTTATGTGAACAAATTGAAGTCTTTATAGCATTCTTAATTT[C/G]GTTTCTGAAAGACATTTAGATAATTGGGCAATTTACAAAAGAGTATGTTC | 58 |
| | | rs177479 | CAAGTTTCATCCACGTTGTAGCGTGTATCAAAACTTCAATTAATATTCTT[T/C]TATATGGGTATGTTACATTTTGTTTATCCATTCATCAGTTGGTAGACATG | 59 |
| | | rs177480 | GCTGCTGTGGACATTTGCATACAAGTTTTTTTGTGTGGAAATATGTTTTC[A/G]ATTCTCTTGGGAATATACCTAGGACTGGAATGGGTCATTTGGAAACTACG | 60 |
| | | rs11981754 | ATTCAAAAATAACAGGATTGTGAAATATCCAACTAAAATCATATTTGAAA[A/G]TGGTCCAGGAATCCCCAAATAACTTTTATGCATGTTATATGAAGATAAAT | 61 |
| | | rs177486 | CCTTCCTTTCAGCATGCAGAATTGAACTTGGCTCTGAAGTAAAACAATAC[A/G]GGTTTTTGAGTGATCCAGCAGCTGTTCTACTTTGGTGAGAGTTTTCTTCT | 62 |
| | | rs177498 | GTCCTCAATTACATCTTTGTGAGAATCAAATGTGATAAGGCATAACACTC[T/C]TGGCATGGTGGCTTTAGATATTAACAACTCTTGCTATGTTGGTTGTGCTT | 63 |
| | | rs2175738 | ATTAGTTTCTGGCTATTGCAGCTAATTCTCGGGTAAAGAATTTGAATGGC[A/G]TTCTAGTATTGCATTTTACCTAGACTACACTGTTACAGAATTGTGTGTAG | 64 |

TABLE 9-continued

| Gene name | Position | Gene polymorphism name | Sequence | SEQ ID NO: |
|---|---|---|---|---|
| | Intron | rs17156579 | TATCACAGGGTTCTTTGTT GGCTATTTATTGACCCAT CTTCTCTCAGGCA [T/C] GTATATTCTCTGGGCAAG TATAGACTCACAAGTGCC TGGAGTCCCTCCTC | 65 |
| | | rs17156603 | ATCAGTACATCAAACAAC TCAATTAACAAATGCTTGC ATCTGCAATGTTC [A/G] TTATAATACAGCATCATAG TTGCAGAATTAAAATGGC AAGATTATAAAAC | 66 |
| | | rs17642145 | GGAAGTAGGACCACCATC GGCCCATACAACTTAAGT CCAATATATAGACT [T/C] TTAACCTATGTCAGTGTG AATAGTTGCCTGCTTGAC CAGGGACTTTAATT | 67 |
| | | rs10229500 | TCCAGTCAGATGACTATT TGTTCAAATATTTATTCTA CTACATGACACAC [T/C] GTGCTGGACACTTCAGAG ATAGCTGTGAGTTTTGCT TCCTGTGTGGTAGC | 68 |
| | | rs10243659 | GTGGGATGCAGGACAAA GTGTTTACTTTTGTCTTTC AGAGTCAAAATGGG [A/C] AAGGTTAACACAAGGAGT AAACTAAGAAAATATATCC ATATCCATATTCA | 69 |
| | | rs4722785 | AACTGGCTTCAGCCAATT ACTATACCTGTTTCCTCTG GCTATAGTGATTG [A/G] TTCAGGGAGAGGCCCTTA ATCTAGTAGCTGTTGAGA TGGAAAAAAAAACA | 70 |
| | | rs16874503 | GAGATAGTTCCTATTCAG GACACACACCCAGTGCTT GCAGATCCATACTG [T/C] TAGACTACGTGAAGGAGG AAGAAAGATGTTTGCAAA GGAGCCAAGGGGGA | 71 |
| | | rs11772815 | ATCCATACTGCTAGACTA CGTGAAGGAGGAAGAAA GATGTTTGCAAAGGA [A/G] CCAAGGGGGAAAGCAGG TTGCCTGCACCAAGATCA GACTGTCTCTTGTGT | 72 |
| | | rs6958133 | GATGTTTGCAAAGGAGCC AAGGGGGAAAGCAGGTT GCCTGCACCAAGATC [A/G] GACTGTCTCTTGTGTTCTT TGATAACTCTGAGATTTTC CTTTCCTATTCC | 73 |

TABLE 9-continued

| Gene name | Position | Gene polymorphism name | Sequence | SEQ ID NO: |
|---|---|---|---|---|
| | | rs16874525 | CTTTCTTCCCATCTATTAA TGAGCATGAACTACATCC TGGCCTTTAATCA [T/C] TGATATCATTTCATATATA CTTTTTCATTATCCTCATC TCTCCTTTGCTT | 74 |
| | | rs17715174 | CATTTTTCATAGAGTCTTT GGCATTGGGTTGGACAAT GATGGAAATTAGT [C/G] AGTTTTACTCAGACAAGG TCCCTTCCTTTGAGGAAT TTATCCTCCATAAT | 75 |
| | | rs6953524 | TGGTATTTCCAGGGAAGA ATACATTAGTAATGCAGG CTTGGGTAACCACT [T/C] GCAGCTCACCTCACTACT GAGCAATGACGTGGAATT GGAGCTGGTATCAC | 76 |
| | | rs10239810 | ATCAGAGCCTGAGCCAAT AATATGAGCTGTCTTCTT GGATAGCTTGGGCT [A/G] GGCTCCACAACAGAAGAA GCTGGGGCAAATTGGCTC TGTTGCTGAGACCT | 77 |
| | | rs17156649 | TTCTGGCAGTGTGAACTT CAATGGCCCACATAATTT TTTTGACCTAATGT [A/G] TAAACATTTTACCTCATGT GTAGAAATAGGGACAATG GTACTACCTCGTG | 78 |
| | | rs1811248 | ATCCTCATTTTAAAGGGA AGGAAACCAATGAGAGTG AAATTTAAGAAACA [T/G] ATCAGATTATTGGGAAAT GGAGTATTCTTCCCAGAG CTCCTCAAAATATC | 79 |
| | | rs887623 | GAGTACCCCTTAACTCAG TGAGGTAGACACCCAAAA GCAACCATCCTGCA [T/C] TTTTTTCCGTGAGCATTAA TAAAGTCTATTGTTCATTG TAGAATGTTCTG | 80 |
| | | rs740988 | TCCCATCTTTCTCACCATT AACATGTACACATTATGC CTAACACGAATCC [A/G] CCAATCCCTTGCAGCCAC TGGCATGCTCATTGGTCT CTGCCTCCAGACCC | 81 |
| | | rs7794304 | TCCTTGCTTACTTCTTTCT CAATCACGCATAATGCCT CAACTCTTAGAGC [T/C] GGCATTTGTTGTATCAGT CCTAATAACTCTTGAGGT ATCTCTGAAATCAG | 82 |

TABLE 9-continued

| Gene name | Position | Gene polymorphism name | Sequence | SEQ ID NO: |
|---|---|---|---|---|
| | | rs6952227 | TAAAGACTTGGAAAGTGT CACATTGTAGTACAGTGG GGTTTTCTCCTGAT [A/G] GCTACAATTTACATGCCA GGAGCCCTGTAAGCCCTC TAGCATTTTCTTGA | 83 |
| | | rs42695 | CATAATTTTATCAAAATTT TTTTCACATACGTTGGCAT GGTCTTCAGACC [T/C] GTGGTAATAATCACACCT CTCTTAACGGGTGGCGTG CTGATCAAATAAGT | 84 |
| | | rs1029897 | CTGTTGAGTGTTCAAGTC TGATTTGGCTTCACCAAG AATAGAACAATGTT [T/C] CTAAAAAGTTTGTCATGAA GAGAAGCCCATTTAGAAA TTCATCCTCTAAC | 85 |
| | | rs4722793 | GGGAGGTGTATTAACTTT TGCCTATGGAGCTAGTAA CAGGTAGAACCGGG [A/C] TTCTTTTTTTTCATCATTTT TTATTATGTAAAATATATA TAACAAAATTT | 86 |
| | | rs10233653 | AAGTTCAGAGTAACTTCC CAGATTTTAAATATTCTGT GTCATGTAAGAAC [A/G] AGGAGGAATCGCTGATCA ATTAGGTTTAAAAGCTACT GAAATTCTCAAGA | 87 |
| | | rs6955105 | CGGCTGTCAAATCTCTTG CTGTCTGCTGCCTTTCCT CTCAGCATGTGAGC [A/G] TGGAGCTGGGGGTCTGG TGGATCCTGTCAATCATA TGTCTGTGGGCAGCA | 88 |
| | | rs17156685 | TTTATCATATGTATCTCCA GCTTGCACCTCTCTCCTT GGCAATGGCCTTC [A/G] CTGCACCTTTGACATTTTC CAACTGCGCCTTTGACAT TTTCCTCTAGATG | 89 |
| | | rs17156694 | CTCAGACTTTCTTTGATG GAGCCAGCCTCCTTGAAA GCAGTTATTTTAG [A/G] TGTTCCAACAGCCATCTA TCTTACAAAAGGATTTTCT CTTCAGATAGGCT | 90 |
| | | rs17156699 | AGAGGAGCTCAGTCAATG GTGAGATCGAATCTTTGG ACCTCCTTTGGACC [A/G] CCGGAATGAAATCACACG TTCCCTACAATAACAAGA GAAGCTGTTATTTT | 91 |

TABLE 9-continued

| Gene name | Position | Gene polymorphism name | Sequence | SEQ ID NO: |
|---|---|---|---|---|
| | | rs177572 | CTCACCTTATTTCCATGAT GCTTGGTTGTCAGTGAAC GCAGATATTGGAG [T/C] TAAGGCCAGTGTTTGTCC CAGGGCCCCAGATCCAA CTGGAGTGAATATTA | 92 |
| | | rs177573 | TTTCTATGGGTGCTATTAA GCATATAAAATTTTTTTC AAAAGGACTGAG [T/C] TGAGTTGGTATGCCACTG TGAACAGTAACTTCATCA CTTGGAAGATCCGA | 93 |
| | | rs177574 | ATTTCCTCATGGTAGCATT TGAACCAAGCCTTTAAGT AGAACAAGATTTT [A/G] CTAAACATAGAAGGCAGA AAGGGCACTGCTGACTAG CTATTTGAAGAAAA | 94 |
| | | rs177576 | TCATTGGTGGATCTGGAG AGTAGCTGACCTGAAAAC AGTCTTCATCTTTC [T/C] GCCAAAATAATTTTAACAC TTAAAAAAATTTTTTTGA GAAGGTACTAGA | 95 |
| | | rs13437706 | CTGAGACACAGTGGGCCT TGGAAATGGCAGTTCCCA TAGGGAGTCCTGCA [T/C] GAGCCATGAAGGCGAGA AGCCAAGGCTTTGCATGC TATGCTTTGGGTGTG | 96 |
| | | rs177580 | TGCAGATCTGATGACAGT ACATCCACACCCTGTCGC TTTCCCTGCCAAGA [T/C] GAACTGTAGCCGTCAGAG CCTCCATTCTGCTCCCCA CACCCATCCAGTGA | 97 |
| | | rs177581 | TGACAGTACATCCACACC CTGTCGCTTTCCCTGCCA AGACGAACTGTAGC [T/C] GTCAGAGCCTCCATTCTG CTCCCCACACCCATCCAG TGACCATCCACTAA | 98 |
| | | rs12666636 | TCTTCTGCACTCCAGCCT CTCCCTCTACTTCCCTCC TTTTTGCTTCAGCC [A/C] GAGGCAGATGGCAGACA TGGATACACATTTATGGA TTGGCTGATGTGTCT | 99 |
| | | rs177584 | GGGTGACGTAAGGGGGT GCAGAGATTCCCACTTG GGTTTATGCTGGCCTC [A/G] TCTTTGACTGGCTCTGTC ATGTTGCCCTTGTGGGGT CCTGTTTTCATTAA | 100 |

TABLE 9-continued

| Gene name | Position | Gene polymorphism name | Sequence | SEQ ID NO: |
|---|---|---|---|---|
| | | rs177585 | TTTTGCACGGTAAATGCT TCGTAAACGTCAGCTATT CATTAGTGAGGTGT [T/C] GGGGAGTTGTCGGGGGA AGAGAGAGGAGAAAGAA GGAAGTGAGAGGGGAG | 101 |
| | | rs216715 | AAAAAGAAAGAGCCAGC CTTTAAGGAAACGGGAA GTCAAAGCTTGTGTAA [T/C] GAAGCAAGACCAGACTTT TTAAATCTACCTCCCTTA ACCTTTATAAACAT | 102 |
| | | rs10951197 | ATGGTGCTACATAGGCTG GCTTAACATCTTTTTTGA AATAAAAACCAAG [T/C] GTAAACATGAGTCAGAAT GACAGGGCATATGCAGG ACTCCAACATTTACT | 103 |
| | | rs160335 | TGAATTTGATGCTGTTCT CTTGGTCTTTTTCACAAC TGAAACATTGGGCC [A/G] TTGGTGGGACGTTCTGT GCCTTGAAACTTTTAATA CGTGCAGCTCCATCT | 104 |
| | | rs1008262 | GTCTTCTCCCCAAGAGG CCACCTTTTTGACCAGGT GACTCTCCTCAGTGA [T/C] GATATGGTGCAATTTTA TGAGATTTTGGGATGTGA AGCAGCTCTGTAGA | 105 |
| | | rs310353 | TGCTAACAGTGCCCTTGG GGAATGTTTGGAGGGAC TTGATTCCAGATCAG [A/G] AAAGATAAACAGTGATCT GGAGGGTCTGGTTTAGA TGCAAGTCATATTTC | 106 |
| | | rs310359 | CACCCTTTACATACCTGT GTCCCTGGATCTTCCTTT CTCCATGGTCCTCA [T/C] AGCCTCTCTTCTTTTACA CTTACCTCTCCTTGAGCT CCCTGATGTGCCTT | 107 |
| | | rs41273 | TGGTTCTGACAAGAAAAA GAAAGTATTCATATTTGG TGGACGTGGTGGTA [A/G] GTAAACTACTAATTTGTA AACATTGGAAATTTTTACT TTAAGTGAGAGCA | 108 |
| | | rs1637457 | AGCTGTTGAGCACACTC GCCTGTGGTTGACAGGA CTCTGGCACAAGTGCC [A/G] TGGAGGATGATGTTAGA GAGGTGGACACATGGGG TCAGAAGAGGAAGGAG | 109 |

TABLE 9-continued

| Gene name | Position | Gene polymorphism name | Sequence | SEQ ID NO: |
|---|---|---|---|---|
| | | rs17156919 | ATTCACCGCATACATTCA CGCAAAGGGAAAATTTA CTGCCTAAACAGAG [A/G] GACCTAAATCCCCCAGG CTAAATAAACCCAATGAA AACACAAGAACTGCA | 110 |
| | | rs41276 | TAAAAAGGTTTCTTCAAA TGAAAAATGGATGGCTGA GCTGCTAATGGCCC [A/G] GTAACCTAAAAATTTAAC TCTTCCCTAATGCTCAGG GACCTCAGGTAAGG | 111 |
| | | rs160375 | TTTTTGTCCTTTATTATTT TTTGAATTACTTTGCTTTA TTTTTCATGTGT [A/G] AAAACACCATATGGTGGC CACAGTGGGAAGCCAGG TCCTCTGCACTAAGA | 112 |
| | | rs917275 | ATAGGAGGTTAGGTATG GTTCTGACATTGCAATAT TCTCTTCAAGTTAAC [A/G] GCAGGCATTTGTTACATG CTCAGAGAATTTTATGAT TTATAAAGAACTTT | 113 |
| | | rs41348 | TTCATTTACGTTATCAACT TAATTAATTTATTTATAAA ATTTCCATGACC [A/G] TAGGATGACCACGTAGAA GTGTGGACTATGGATCAC TAGCATCAAAATCT | 114 |
| | | rs886816 | CAGGAAAGCCATCTTTAC ATCACCTCTATTTAAAGC ACAGGGTCCCTTTT [A/G] CCTATGTCACTGAAAAAC AGCAGAAGCCTGGTATCT AGTGGATTCACCCC | 115 |
| | | rs17157048 | ATGCAATCTGATTTATTTC CATGGATTCTGAGCTAGG AATCGCAATTGGG [A/C] ATCTCCAGAACCAATGGG GATTTTTGCTGTAGGACC ATCGTTCTTTTCTG | 116 |
| | | rs6462098 | TTTTCCAAAGCAGCTTAA TGTAGAACAATAGGGCCA AGAAGGGGTTTTTT [T/C] GCTCTGAAAAATACCGAG TCCCCTGCCCAAGAGCT CCAGTGCCTCCCTCC | 117 |
| | | rs10951201 | CCCCAAATACCACATTTG TTTGCAAGTAGGAATAGG ACTGTCTGAGGAAT [A/C] ATTTGAGAAACTGAGCAA GTCACTCTCTTTGGCAAC ATGCAGGGCCACCA | 118 |

TABLE 9-continued

| Gene name | Position | Gene polymorphism name | Sequence | SEQ ID NO: |
|---|---|---|---|---|
| | | rs13311248 | TTGTGTGCCAAGCTCAGT GCTCTCAAATATTCTCCC TTCAGCCTAGAAGA [C/G] AGACTGGTACCTGCTGTA AGGGGTCTGGCATGGAG AGAAAGCCGGCTTCC | 119 |
| | | rs12540480 | TATTTTCTACAGCAGATC ACTCATCTCTTAAATAGA TTATGCATTGATCG [T/C] CTTCAAAGGGCTAAGCAC ACTCAAAATATTCTCTAAA GTCATTCTCATGC | 120 |
| | | rs10265166 | TCCCTAGAAAGCAAGTCA GACAGGGACAAGTCTATT TTTTAAGAGCCCAA [T/G] AAGAGGAAATTTCAAAAT CTCTATTAGCCATTTAATT GTTTTACACTATT | 121 |
| | | rs7798774 | CATCATTATCTGCCAGCC TTCTCTAATGTCTCCCCC ATGGGCTAAAGAAG [T/C] CTTATTTCCTTTACTTTTC CCATTAAGTCTTCCCTTC CGGCTTTTTAGTA | 122 |
| | | rs7799246 | TCAGCCTTGTTAGGCAAT GCCCCTTTCCTTGTTCAT GTTTCCTTGGAGAA [T/C] AAGTGATCCTCTCAGCAC GCTATCACTTTATCATTAA GAATAGAACTTGA | 123 |
| | | rs6972081 | TTGGTTAATAAATGAATC AAGCTGACTGCATGACTA ATTCAGATTAATGG [T/C] GCAGAAATCAGTCACTAA AGAAGCCAAAAAAGTTT GCTTTAATAGTCTT | 124 |
| | | rs12533079 | GCTTGACAGTAAGATTTG GTTCGGAACATGAGCTCA TTCACAAAAAGATA [T/G] GGGTAATAAGACGTCTTT TAAAAATATGGGTCAGGC AGCTTTCTCGTGTT | 125 |
| | | rs7806547 | CTTCAAGAGTCTTTGAGA TGCCTATAGGCTCATCTG TTCATTACAAGATG [A/G] TGAAATGGAGAGCCTGA AAGTTAAGAGTCTTTTCC CCCAGTCAATAACTT | 126 |
| | | rs6462100 | CAGATCTTCTGAAGACCT GAGAAAGGACAGCAGGG TGGAGAGACCCCTTC [A/G] CACCTTCCAGACGAAAG CACTGGCCTGAGGATAG GCTTGCCCAAGGGCAA | 127 |

TABLE 9-continued

| Gene name | Position | Gene polymorphism name | Sequence | SEQ ID NO: |
|---|---|---|---|---|
| | | rs6979352 | ACCCCTAGACAGGAAAA CATCCTTCGGGGGAAA AATGAGGACATGAAAT [T/C] GCTTGCTGCGGTGCCTA TCATTCTGTTAAGGACAG TGAAAACACAGTCTG | 128 |
| | | rs6950574 | TATTCAGAATCCAAACAT ATAGGGATCTCAAATAAT CCTTTCCCTTCTAT [A/G] CACTACTAATTAGCTTGA TCGATATCATTAGGAAAT TATTATTATAATCC | 129 |
| | | rs4722835 | ACATTAAGACCGGAGGAT ATCAACAAATTTGGTTGA CTGAGCCACATCCT [A/C] TACCTATCTGACTCAGTC TATCCACCTGTGAAGGAG ACTTTAAGACCTAG | 130 |
| | | rs2066979 | TGGTGAATGAAAGGCAG TGCAGAGACTGCCTCTCT TTTTGAGGATGTTTG [T/C] TACAGAGCCTTGGTGTCA GATAATCATGTAACAAGC ACTGGATTGGCAAG | 131 |
| | | rs10486591 | GGATTCATTTTCTGAAGA ATTAAGTCAACAGACATG GCTTCACAATGCAC [A/G] TATTGGATTCCTTTTGGG GGTCAGAGCAGACTCAG AGCTCTGAGAGGCTT | 132 |
| | | rs721993 | GAGAGCCTCAGCTTCCC AGTTGCTTGCTGGACCCT AAAGCTGTAAGAACT [T/C] TGTGAAACTTGAATGTTT CTTTTTTTAACCAAGGTA AGGAATTTAATGCC | 133 |
| | | rs2237351 | GGAGGTACCTTCATCCTT GAGAAGAGAGACTTCAG TATCTGTGGAACAAG [T/C] GAAGCTAGAACTTGGCAT CGGAGCATAGTGCTGAG CAAAGAAGCCTCTAC | 134 |
| | Exon | rs3735566 | TCTCTTAAACTCCCTCCA CTCAACACAACTGATACC TTTCATTATCTCCT [A/G] TAGTGTCTGTGGCATTGG TATTCTAAAGGAGAAAAC TAGAATCTAATGAG | 135 |
| | 3' Flanking region | rs11975539 | TTGTTGTTTTTGTTGCCA CCACAAGAGCAAAGGTAT TTCCTATTTTGTTT [A/G] AATTTGTCACTAAGATCT AAAACAGTGGACACACAA TGGGCACACAACAA | 136 |

TABLE 9-continued

| Gene name | Position | Gene polymorphism name | Sequence | SEQ ID NO: |
|---|---|---|---|---|
| | | rs6462107 | ATGCCTCCAGGCTTATGT TCTTAGTCTAATACTCAG CCCTTAGCTCACAA [T/C] GGAATCATCAATCCCAGC AACTAGATATTGGGACAG GGAACCTAGAGAGT | 137 |
| | | rs2190306 | TTGATAACCTAGTTTAGT ATCCTATGAGTGCCTTAA ATACAGAGGATGCT [T/C] AATGAAAATTTATTAGACT GCCCGCTCAGCAGCTCA CTGGGATTGAATAT | 138 |
| | | rs4719955 | ATCTGCACATGCCAGTG GTCTGAATAACAGAAGGA GTCCTTCCAAGGCCA [T/C] CCTGACCTGCAGCCATG TTGGTGTAGGAACTGTCT CCAGGGAGCCAAAGT | 139 |
| | | rs10228137 | CTAGAAAATATCCGTCTC TTGTTCTAGCAGCCATAG GTAAATGACAATGG [A/C] GACGCTACTGAAAAATCA CAACTCGTGTGTTCTAAA ATGACCACAAAGGG | 140 |

TABLE 10

| Gene name | Position | Gene polymorphism name | Sequence | SEQ ID NO: |
|---|---|---|---|---|
| ATF2 | 5' Flanking region | rs268174 | ACGCGTGTATGTTTTACAATATACATCTCTCATAATATCAACTGAAGCAA [T/C] ATTTAATGTTTCAGTCTACCACAGATCATTTATTTTCTAGCAAATGTCTT | 141 |
| | | rs13030474 | ACATGTGAGTTGAAGTTACTCCATGAAGCCCCTAAGAATGTGCAGAAAAG [T/G] GATTGATTCAAATGGATCATTCTTTCTTTTCCATTACCTTTTTTTTTTCC | 142 |
| | | rs268237 | TGGACTGACTTATATAAAAAATTAGAGAAAAATACAAATTAGTACACATT [T/C] CAGGACAAAGTTGTGTGATGCACTAAGGGAAATCGCATTAGAAAAGAGAT | 143 |
| | | rs1982235 | TGAGGAGGAAGCAAGAAAGAAGCCAAGATCCACAGTGGCTGCTTCCAAGT [T/G] GCATATGGACTAGTTGCTTGTGGCAGGGAGAGACATGGGTTCCGAAATCC | 144 |
| | | rs10497435 | AAATAGAGATAATTCACGTGTACTGTTCAACAAGCAATTATTCATATAGT [T/C] TCTCAAGTACTCAATTCTAACCAAGAACATGGTGTCCTGTGGTGTCTACA | 145 |
| | | rs268231 | GTAATTCTAACAAATGGCTAATGGAAGTGATATCAACACGTCAACATAAA [A/C] GATTAAACATCTAGAATGCCCTGCTAAGAAGATGGCTGGGGACTGAACTC | 146 |
| | | rs268230 | GAAAGAAGGGTCATTCACTACTTAACAGGAAACTAGGGTCCCCAGCAAAG [A/C] GAAGATATTTATTTCAAGGAACCTGGAAAATGGTTCCAGAAGTATGGCTA | 147 |
| | | rs268229 | ACAAAAAGAAAAACTGTAGATTCACCCCGGCAGAGAGGACTAAACAGATT [A/G] ACTTTTGATATGAGTTGGCTGCAGGATAGTGGGCCTTTTTCTTCACGTTG | 148 |

TABLE 10-continued

| Gene name | Position | Gene polymorphism name | Sequence | SEQ ID NO: |
|---|---|---|---|---|
| | | rs268228 | CCCTGTGCCCTCCACTTACCTTCCCAGGAGGCGGCGGCGGCACGGGCTGC[A/G]GCAGAGGTCGAAGGAGTGGGACTCAATGCGCAAGCGCGGTCCGGCTCTTA | 149 |
| | | rs166531 | GGTGAGCTCCGGAAAGGCTGCTAGAGGGAAAGCAGGATGGGTCCTCCGAG[T/C]CCAGCCCCAGGAGCCGGGTGTCTCCGTTTCCGTCACTTCCCAGCACTAGG | 150 |
| | | rs268214 | TTCTGGAGGGGCGGGACCAGAGGGCCCAAGGAGCGTTACTTCTGTAAAC[T/C]CGGAGCTGTGGAAGACTGTGATTGGCTGTCGGCTGGAGGAGGGCGCGGGT | 151 |
| | Exon | rs10497434 | TTCTAGCTGGTGGGCCATGAGCTTTATTTACTCTGCTTCCAGGAATACCT[T/C]AGCTGTTATCAATAAGCAGTCCTTTCTCAAGTTTCCATCTAGTACCCTTA | 152 |
| | Intron | rs11888507 | CCCCTCTTAAAGAGCTTGATCTGCCAACATTGGAGAAAAGGGCAATCCTA[T/C]ATATCCATGATCCTGACATACCTGCCTCAGGTAAACTAGGGGAGATACTG | 153 |
| | | rs13388308 | TTTCCCTCCTCCTATCCCACCATGGGCTGGATTCTTCATTTCACATCCTA[T/C]AAAACTCAGCATAATTTCCAGGTTTGAAATGGCAACTTTCTCTCTGTCT | 154 |
| | | rs3755490 | AAATTGCATTTTTCATAATTTTGTTCATAAATGAAGTTTCAAGAATGTCA[T/C]GCTCAGAAAAATTTGGTAATTCTTGTGGGGAAATGTGTAACTAGCCAAAG | 155 |
| | | rs7578569 | ATAAATTTGGGAAATGTTGAATGTGTAGGCTTCATTTCACAGGACTTTTC[A/G]TGACCTTAATGTTATGTCAATTAAGGATTCATAACTTTAAAAAATGCCCC | 156 |
| | | rs7566401 | ATACTTTCTAAAGCTCAGTTGCACTATTGAAGAAAAGCAGAATTTCTTG[A/C]CAAAAGTTTCCTGGGTTTTTTTTCATCCTAACTCTAAAATTTTACAGAAT | 157 |
| | | rs1153676 | GAAGGTAACTGTTAATAATCCAAACAAAAGATGATGATGGTTTGGGCTTA[A/C]GTGGTGTCACTGAACACAGACATAGAGGATGAGATTCAGGTCTGATAAAA | 158 |
| | | rs1205399 | GCACTCCAGCCTGAGTGACAAAGAGAAAGACTGTCCAAAAACAACAACAA[A/C]AAAAAAGAATTACAGTCAGGTGCAGTGACTCACGCCTGTAATCCCAACA | 159 |
| | | rs2072538 | TTAGGTTTTCCCTGTCCCCAGTAAGCAGATCTAGTTCTCTTTTGCTGTTG[T/C]AGGTTTGCCAGTTAATTATTGGATTGTACTGGACTCACATTCAGAGCATG | 160 |
| | | rs212361 | ACAAGATACAGTTATGTAAATACCTATGCTTAGGTGGCAATCTAAAACTT[A/G]TTTATATGTGTTTCTTTGATTGAAAACTTTTGCTTTTTAATGCCAATGCT | 161 |
| | | rs212360 | GAAGCTTAATTTCTGCTACTCAGAGTTACATTTGTATATTTTTATGCCTA[T/C]CAAGGATTGGAGGCTTCTTAGAAGTGTATACTGCTCCTTCTCTCCCCATG | 162 |
| | | rs1153685 | CTTATTTCAGTTGCTTTTCATAATAGTACTTATTCTATCAGTTTGACGGA[A/G]AAACAAAGGCTTAGGAAGATTCTTAGTAAAAGCTTCAAATGTAAGTATTA | 163 |
| | | rs12693057 | ATTAGAAGCACAGTCTCCATTTTTAAAGTAGCAGCTCAGTTCACTCTGAC[A/G]GTATTTCACTGACGTAGCCTAAGGCTATAGGTAATGGAACATTACTCACT | 164 |
| | | rs212347 | TCTTATCAAAAAGAAGGACATTACAAAAAGGAAAAGGCACAATTAACCT[T/C]TAAAATGCTGAAAACAAAAGAATCTCATTCTTTGGGAAAACATTTAGCAG | 165 |
| | | rs212349 | ACGGAATCTTTTAAATTAAAAAATATTGCCCATTCTGATGAAACTGCTTA[T/C]AATGACTACAAGTAAAGATGGTGGCCATTAAGTTTTATCGTGAGCACCTG | 166 |
| | | rs3845744 | CCAGTTTTAGCACTGAAAGTCCTGCTTCCTAAGAAGACCCCTCAGTCGTG[A/G]GAAAACCATGACAGTTAGTCACCCCAACAGTTAAGTAATATAAAACCTGA | 167 |

TABLE 10-continued

| Gene name | Position | Gene polymorphism name | Sequence | SEQ ID NO: |
|---|---|---|---|---|
| | | rs2302663 | TTATCAGCAGCTGGGTGGAAAAAAGAAAAATTATTCATTTTCCTAAAATC [A/G] GTAAGAATGCACCAGTATGCTGAGGCAATACACAGAGTAAAAAGTTAGAA | 168 |
| | 3' Flanking region | rs1153699 | GTGGGTTTGATTCTTGTCCTAGTCTAGCCTCAGTTTTGGGCAGGCACTGC [T/G] TTGGGGTGGGGCTTTCTCAAATATCCTGCCCCTTTTCCAGTAGCAGGAAA | 169 |
| | | rs7583431 | ATCCTTTCTGTGTGTCTCCTCTTGTGGCTACACTTGACGGGCCATATTAT [A/C] AAAGAATACAAAACAATAGTACAGACAGGTAAATGTTTATGCCTAGAAAT | 170 |
| | | rs1153702 | TGTTGTTCATATTTTAAAAAAATTCTTAGCCATTATCTCTTCAAATAACA [T/C] GTTTGCCAAGTTCTCAATATGATATTGTTCCATAGATCTTGGATGCTGTG | 171 |
| | | rs1153711 | TGTGTGTCTTGCAGCAGCTGGATGAAGGTTCTGTAAATGTATGCTACGTC [T/G] GTTGAGTCCATGGTGTAGTTTAAGTCTGATAATTTTTGTTGATTTTTTTT | 172 |

In Table 7 to Table 10 (SEQ ID NOS: 1 to 172), 101 nucleotides are shown, and a gene polymorphic site is shown at the 51st nucleotide. For example, one represented by "A/G" means a gene polymorphism associated with transitions between "A" and "G", and "C/T" means a gene polymorphism associated with transitions between "C" and "T".

3. Haplotype Analysis

In the present invention, by using SNP among the above-mentioned gene polymorphisms, a haplotype can be constructed. The SNP to become a target of a haplotype analysis may be any as long as its gene polymorphism frequency is 0.5% or higher, preferably, those with a gene polymorphism frequency of 1%, more preferably those with a gene polymorphism frequency of 5% or higher can be selected. Further, SNP to become a target of a haplotype analysis may be a full or partial sequence thereof.

The haplotype analysis can be carried out using various computer programs, and for example, Haploview (available from the following website: Broad Institute) (the same shall apply hereafter); Barrett J C, Fry B, Maller J, Daly M J. Haploview: analysis and visualization of LD and haplotype maps. Bioinformatics. 2005 Jan. 15 [PubMed ID: 15297300] Whitehead Institute for Biomedical Research Cambridge, Mass. 02142, USA.) can be used.

As an example of the haplotype analysis, among cyclic AMP responsive element binding protein gene polymorphisms in Japanese healthy subjects found as in the above-mentioned 2, with regard to the 17 sites of SNPs which are CREB1 subtype gene polymorphisms, the 40 sites of SNPs which are CREB3 subtype gene polymorphisms, the 64 sites of SNPs which are CREB5 subtype gene polymorphisms, and the 31 sites of SNPs which are ATF2 subtype gene polymorphisms, a haplotype was estimated for each linkage disequilibrium block (haplotype block), using Haploview. The estimated haplotypes are shown in Tables 11 to 14. It is to be noted that the "Tag" shown in the tables indicates a Tag SNP that is a typical gene polymorphism in the linkage disequilibrium block.

TABLE 11

Gene name CREB1
Linkage disequilibrium block No. 1

Gene polymorphism name (✕)

| Haplotype No. | 1 Tag | 2 Tag | 3 Tag | 4 | 5 | 6 | 7 | 8 | 9 | 10 | 11 | 12 Tag | 13 Tag | 14 | 15 | 16 | 17 Tag |
|---|---|---|---|---|---|---|---|---|---|---|---|---|---|---|---|---|---|
| H1 | C | C | C | A | G | G | G | T | C | C | C | C | C | C | A | A | T |
| H2 | C | C | A | G | A | T | A | C | T | A | T | C | C | T | G | G | T |
| H3 | C | T | C | A | G | G | A | T | T | C | C | C | C | C | A | A | T |
| H4 | T | C | A | G | A | T | A | C | T | A | T | C | A | T | G | G | C |
| H5 | C | C | A | G | A | T | A | C | T | A | T | A | C | C | A | A | T |
| H6 | T | C | A | G | A | T | A | C | T | A | T | C | C | T | G | G | T |
| H7 | T | C | A | G | A | T | A | C | T | A | T | C | A | T | G | G | T |
| ... | Haplotypes which are estimated to occur at a frequency of less than 1% | | | | | | | | | | | | | | | | |

(✕) 1~17: (in this order)rs16839837, rs2360969, rs10932200, rs2253206, rs2551640, rs11904814, rs16839883, rs6740584, rs3770704, rs2254137, rs2551645, rs2551946, rs4234080, rs2952768, rs2709386, rs7591784 and rs7594560

TABLE 12

Gene name CREB3

Linkage disequilibrium block No. 1
Gene polymorphism name (※)

| Haplotype No. | 1 Tag | 2 Tag | 3 Tag | 4 | 5 | 6 | 7 | 8 | 9 Tag | 10 | 11 Tag | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| H1 | G | C | G | T | A | T | T | T | C | T | C | C | G | C | T | G | T | G | T | C | A | G | G | A |
| H2 | G | C | G | T | A | T | T | T | T | T | C | C | G | C | T | G | T | G | T | C | A | G | G | A |
| H3 | T | T | A | T | A | T | C | T | C | T | T | C | G | A | G | A | C | A | C | C | G | T | G | C |
| H4 | T | T | A | T | A | T | C | T | C | T | C | C | G | A | G | A | C | A | C | C | G | T | G | C |
| H5 | T | C | G | C | C | C | C | C | C | T | C | C | A | A | G | G | C | A | T | C | A | T | A | C |
| H6 | T | T | G | T | A | T | C | T | C | C | C | T | G | A | T | G | C | G | T | C | A | G | G | C |
| H7 | T | C | A | T | A | T | C | T | C | T | T | C | G | A | G | A | C | A | C | C | G | T | G | C |
| ... | Haplotypes which are estimated to occur at a frequency of less than 1% | | | | | | | | | | | | | | | | | | | | | | | |

Linkage disequilibrium block No. 2
Gene polymorphism name (※)

| Haplotype No. | 25 Tag | 26 Tag | 27 | 28 | 29 Tag | 30 | 31 | 32 | 33 | 34 | 35 | 36 Tag | 37 | 38 Tag | 39 Tag | 40 |
|---|---|---|---|---|---|---|---|---|---|---|---|---|---|---|---|---|
| H8 | C | C | G | G | G | C | G | G | G | A | T | A | C | C | G | C |
| H9 | C | T | A | T | G | T | A | G | A | G | A | A | T | C | A | T |
| H10 | T | C | G | G | C | T | G | A | A | G | A | A | T | C | G | C |
| H11 | C | T | A | G | G | T | A | G | A | G | A | A | T | C | G | T |
| H12 | C | C | G | G | C | T | G | A | A | G | A | A | T | C | G | C |
| H13 | C | T | A | T | G | T | A | G | A | G | A | G | T | C | A | T |
| H14 | C | C | G | G | G | C | G | G | G | A | T | A | C | T | G | C |
| ... | Haplotypes which are estimated to occur at a frequency of less than 1% | | | | | | | | | | | | | | | |

(※) 1~40: (in this order) rs1243872, rs2145925, rs2025126, rs1885373, rs1885374, GA007473, rs2295794, rs4879926, GA007477, rs867194, rs11541908, rs741917, rs7862485, rs2756894, rs2249250, rs2295795, rs877365, rs2737273, rs2295797, rs2295798, rs1534847, rs7873822, rs2737274, rs10972567, rs3763630, rs10814274, rs3750434, rs1570246, GA025684, rs1570248, rs1570249, rs34478611, rs1322045, rs1951432, GA025687, rs10814275, rs10758320, rs4878628, rs10758321 and rs10758322

TABLE 13

Gene name CREB5

| | Linkage disequilibrium block No. | | | | | | | | | | | | | | | | | | |
|---|---|---|---|---|---|---|---|---|---|---|---|---|---|---|---|---|---|---|---|
| | 1 | | | | | | | | 5 | | | | 6 | | 9 | | 10 | | |
| | | | | | | | | | Gene polymorphism name (✕) | | | | | | | | | | |
| Haplotype (H) No. | 1 Tag | 2 Tag | 3 | 4 | 5 Tag | 6 Tag | 7 Tag | 8 Tag | 9 Tag | 10 | 11 | 12 | H No. | 13 Tag | 14 Tag | H No. | 15 Tag | 16 Tag | H No. | 17 Tag | 18 Tag |
| H1 | C | T | A | A | G | C | C | C | G | C | A | G | H11 | T | G | H14 | T | A | H17 | G | T |
| H2 | G | C | G | A | G | T | C | A | A | C | G | G | H12 | C | C | H15 | C | A | H18 | G | G |
| H3 | G | C | G | A | A | T | C | C | G | G | G | G | H13 | C | G | H16 | C | G | H19 | A | G |
| H4 | C | C | G | A | G | T | T | A | A | C | G | A | ... | | | | | | | | |
| H5 | G | C | G | A | G | C | C | C | A | C | G | G | | | | | | | | | |
| ... | Haplotypes which are estimated to occur at a frequency of less than 1% | | | | | | | | | | | | | | | | | | | | |

| | Linkage disequilibrium block No. | | | | | | | | | | | | | | |
|---|---|---|---|---|---|---|---|---|---|---|---|---|---|---|---|
| | 11 | | 12 | | | 13 | | | | 15 | | | 16 | | |
| | | | | | | Gene polymorphism name (✕) | | | | | | | | | |
| Haplotype (H) No. | 19 Tag | 20 Tag | H No. | 21 Tag | 22 Tag | 23 Tag | H No. | 24 Tag | 25 Tag | 26 Tag | 27 Tag | 28 Tag | 29 Tag | 30 Tag | 31 Tag | 32 | 33 |
| H20 | T | A | H24 | G | C | C | H28 | A | A | G | T | C | C | C | C | G | C |
| H21 | T | G | H25 | G | C | T | H29 | G | A | A | C | T | T | C | A | G | C |
| H22 | C | G | H26 | A | C | T | H30 | G | G | A | T | T | C | C | C | G | C |
| H23 | C | A | H27 | G | T | T | ... | | | A | T | C | T | T | T | A | T |
| ... | Haplotypes which are estimated to occur at a frequency of less than 1% | | | | | | | | | | | | | | | |

| | Linkage disequilibrium block No. | | | | | | | | | | | | | | | | |
|---|---|---|---|---|---|---|---|---|---|---|---|---|---|---|---|---|---|
| | 25 | | 26 | | | 27 | | | | | | | | 32 | | | |
| | | | | | | Gene polymorphism name (✕) | | | | | | | | | | | |
| Haplotype (H) No. | 34 Tag | 35 Tag | H No. | 36 Tag | 37 Tag | 38 Tag | 39 Tag | H No. | 40 Tag | 41 Tag | H No. | 42 Tag | 43 Tag | 44 Tag | 45 Tag | 46 | 47 Tag | 48 | 49 | 50 Tag |
| H39 | T | A | H42 | G | A | G | G | H47 | A | A | H49 | A | C | G | T | T | G | T | T | T |
| H40 | C | G | H43 | G | A | A | A | H48 | G | G | H50 | A | C | G | T | T | G | T | T | C |
| H41 | T | G | H44 | A | G | G | A | ... | | | H51 | A | A | C | T | C | G | T | T | C |

TABLE 13-continued

Gene name CREB5

| Haplotype (H) No. | 51 Tag | 52 Tag | 53 Tag | 54 Tag | 55 | 56 | H45 | H52 | | | | | | |
|---|---|---|---|---|---|---|---|---|---|---|---|---|---|---|
| ... | | | | | | | H45 | | G | A | C | C | C | T | C |
| | | | | | | | H46 | H53 | G | G | C | A | C | C | T |
| | | | | | | | ... | H54 | | | A | C | G | T | T |
| | | | | | | | | H55 | | | A | T | G | T | T |

Haplotypes which are estimated to occur at a frequency of less than 1%

Linkage disequilibrium block No. 35

Gene polymorphism name (X̄)

| Haplotype (H) No. | 51 Tag | 52 Tag | 53 Tag | 54 Tag | 55 | 56 | H No. | 57 Tag | 58 Tag | H No. | 59 Tag | 60 | 61 | 62 | 63 | 64 |
|---|---|---|---|---|---|---|---|---|---|---|---|---|---|---|---|---|
| H56 | T | G | G | C | A | A | H61 | C | T | H64 | G | G | C | T | T | C |
| H57 | T | A | A | T | G | C | H62 | T | C | H65 | A | A | T | C | C | A |
| H58 | G | A | A | C | G | C | H63 | T | T | ... | | | | | | |
| H59 | T | A | G | C | A | A | | | | | | | | | | |
| H60 | T | A | A | C | G | C | | | | | | | | | | |

Haplotypes which are estimated to occur at a frequency of less than 1%

(X̄) 1-64: (in this order) rs4722778, rs177479, rs177480, rs11981754, rs177486, rs177498, rs10229500, rs10243659, rs4722785, rs6874503, rs16874525, rs6958133, rs17715174, rs10239810, rs17156649, rs1811248, rs887623, rs740988, rs6952227, rs42695, rs1029897, rs10233653, rs6955105, rs171156699, rs177572, rs177573, rs177580, rs177581, rs177584, rs177585, rs1008262, rs310353, rs41273, rs1637457, rs17156919, rs41276, rs160375, rs917275, rs17157048, rs6462098, rs10951201, rs13311248, rs12540480, rs10265166, rs7798774, rs7799246, rs6972081, rs12533079, rs78806547, rs6950574, rs4722835, rs4722835, rs4722835, rs721993, rs2237351, rs3735566, rs11975539, rs6462107, rs2190306, rs4719955 and rs10228137

TABLE 14

Gene name ATF2

Linkage disequilibrium block No.

| Hap-lotype No. | 1 | | | | | 2 Gene polymorphism name (✗) | | | | | | | | | | |
|---|---|---|---|---|---|---|---|---|---|---|---|---|---|---|---|---|
| | 1 Tag | 2 Tag | 3 Tag | 4 Tag | 5 Tag | 6 | 7 | 8 | 9 | 10 | 11 | 12 | 13 | 14 | 15 | 16 |
| H1 | T | C | A | A | G | C | C | A | G | C | G | T | C | A | A | A |
| H2 | G | C | A | G | G | T | T | G | A | T | A | C | A | C | C | G |
| H3 | T | T | C | G | A | T | T | G | A | T | A | C | A | C | C | G |
| H4 | T | T | A | G | A | T | T | G | A | T | A | C | A | C | C | G |
| | | | | | G | G | T | T | G | A | T | A | C | A | C | G |
| ... | Haplotypes which are estimated to occur at a frequency of less than 1% | | | | | | | | | | | | | | | |

| Hap-lotype No. | Linkage disequilibrium block No. 2 Gene polymorphism name (✗) | | | | | | | | | | | | | | |
|---|---|---|---|---|---|---|---|---|---|---|---|---|---|---|---|
| | 17 | 18 | 19 | 20 | 21 Tag | 22 | 23 | 24 | 25 | 26 | 27 | 28 Tag | 29 | 30 | 31 |
| H5 | C | T | T | C | C | C | G | A | C | A | C | T | T | G | T |
| H6 | T | C | C | T | T | T | A | G | A | C | T | G | C | G | C |
| H7 | T | C | C | T | T | T | A | G | A | C | T | T | C | G | C |
| H8 | T | C | C | T | T | T | A | G | A | C | T | G | C | G | C |
| H9 | T | C | C | T | C | C | G | A | C | A | C | T | T | G | T |
| ... | Haplotypes which are estimated to occur at a frequency of less than 1% | | | | | | | | | | | | | | |

(✗) 1~31: (in this order)rs1153711, rs1153702, rs7583431, rs2302663, rs3845744, s212349, rs212347, rs12693057, rs1153685, rs212360, rs212361, rs2072538, rs1205399, rs1153676, rs7566401, rs7578569, rs3755490, rs13388308, rs11888507, rs10497434, rs268214, rs166531, rs268228, rs268229, rs268230, rs268231, rs10497435, rs1982235, rs268237, rs13030474 and rs268174

Further, from the genotype information of cyclic AMP responsive element binding protein (CREB) genes of the respective individuals in a population, a haplotype frequency in the population is calculated, and a linkage disequilibrium analysis can be carried out based on the thus obtained haplotype frequency. The D' value and r2 value, which indicate measures of linkage disequilibrium, can be calculated based on the following definition.

Definition

It is assumed that there are SNP A and SNP B, and the respective alleles are represented by A and a, and B and b. The four haplotypes formed by SNP A and SNP B are represented by AB, Ab, aB and ab, and the respective haplotype frequencies are represented by PAB, PAb, PaB and Pab.

$D = P_{AB} \times P_{ab} - P_{Ab} \times P_{aB}$ (In the case of $D>0$)

$D' = (P_{AB} \times P_{ab} - P_{Ab} \times P_{aB})/\text{Minimum}(((P_{AB}+P_{aB}) \times (P_{aB}+P_{ab})), ((P_{AB}+P_{Ab}) \times (P_{Ab}+P_{ab})))$ (In the case of $D<0$)

$D' = (P_{AB} \times P_{ab} - P_{Ab} \times P_{aB})/\text{Minimum}(((P_{AB}+P_{aB}) \times (P_{AB}+P_{Ab})), ((P_{aB}+P_{ab}) \times (P_{Ab}+P_{ab})))$ $r2 = (P_{AB} \times P_{ab} - P_{Ab} \times P_{aB})^2/[(P_{AB}+P_{Ab})(P_{AB}+P_{aB})(P_{aB}+P_{ab})(P_{Ab}+P_{ab})]$

[However, Minimum $(((P_{AB}+P_{aB}) \times (P_{aB}+P_{ab})), ((P_{AB}+P_{Ab}) \times (P_{Ab}+P_{ab})))$ means that a smaller value among $(P_{AB}+P_{aB}) \times (P_{aB} P_{ab})$ and $(P_{AB}+P_{Ab}) \times (P_{Ab}+P_{ab})$ is adopted.]

Further, a haplotype block can be estimated from the results of the linkage disequilibrium analysis. As for the haplotype block, a linkage block can be estimated from the results of the haplotype analysis by using, for example, Haploview.

When a specific SNP in the estimated haplotype blocks is examined, the information of SNPs indirectly linked to each other in the same block can be obtained. That is, when a gene polymorphism of the cyclic AMP responsive element binding protein gene (specifically, a CREB1 subtype gene, a CREB3 subtype gene, a CREB5 subtype gene, or an ATF2 subtype gene) is examined, it is not necessary to analyze all the SNPs, and it is only necessary to perform typing for several specific SNPs, for example, representative SNPs such as a Tag SNP.

4. Correlation of Cyclic AMP Responsive Element Binding Protein Gene Polymorphism with Drug Sensitivity and Disease Vulnerability It is considered that when a gene polymorphism occurs in the cyclic AMP responsive element binding protein gene, the function or expression level of the cyclic AMP responsive element binding protein might change. Therefore, there is a correlation between a cyclic AMP responsive element binding protein gene polymorphism and various phenotypes associated with the cyclic AMP responsive element binding protein in some cases.

Here, as the phenotype, a phenotype associated with sensitivity to drugs (drug sensitivity) and a phenotype associated with occurrence of a disease (disease vulnerability) can be exemplified. As the drug sensitivity, an efficacy of drugs, a side effect of drugs, duration of efficacy of drugs and the like can be exemplified. As the disease vulnerability, pain sensitivity, vulnerability to substance dependence (in particular, vulnerability to drug dependence) and the like can be exemplified.

In the present invention, the type of the aforementioned drug is not particularly limited, and preferred examples of the drug include opioid receptor function modulators and cyclic AMP responsive element binding protein function modulators. Examples of such modulators include various drugs acting directly or indirectly on the opioid receptor or the cyclic AMP responsive element binding protein. Specific examples of various drugs acting directly or indirectly on the opioid receptor include a stimulant such as methamphetamine, a dopamine receptor agonist, a dopamine receptor antagonist, a m-, κ-, or δ-opioid receptor agonist, a m-, κ-, or δ-opioid receptor antagonist, and the like. Specific examples of various drugs acting directly or indirectly on the cyclic AMP responsive element binding protein include phosphorylated enzyme, a coactivator, a PDE4 inhibitor, dephosphorylated enzyme, an agonist for each subtypes of the cyclic AMP responsive element binding protein, an antagonist for each subtypes of the cyclic AMP responsive element binding protein, and the like.

Examples of the opioid receptor function modulator include morphine, DAMGO, codeine, methadone, carfentanil, fentanyl, heroin, cocaine, naloxone, naltrexone, nalorphine, levallorphan, pentazocine, pethidine, buprenorphine, oxycodone, hydrocodone, levorphanol, etorphine, dihydroetorphine, hydromorphone, oxymorphone, tramadol, diclofenac, indomethacin, flurbiprofen axetil, marcain, ethanol, methanol, diethyl ether, propanol, butanol, flupirtine, laughing gas, F3 (1-chloro-1,2,2-trifluorocyclobutane), halothane, estradiol, dithiothreitol, thioridazine, pimozide, fluoxetine, paroxetine, desipramine, imipramine, clomipramine, tetramide, isoflurane, ginsenoside, ifenprodil, bupivacaine, tertiapine, clozapine, haloperidol, SCH23390, cocaine, and the like. In particular, morphine, pentazocine, pethidine, buprenorphine, diclofenac, indomethacin, flurbiprofen axetil and marcain are preferred, and morphine, fentanyl and pentazocine are more preferred.

Preferred examples of the cyclic AMP responsive element binding protein function modulator include phosphodiesterase 4 (PDE4), calcineurin, protein kinase A, protein kinase C, p90 ribosome S6 kinase 1 (RSK1), calmodulin kinase, glycogen synthase kinase 3β, and CREB-regulated transcription coactivator 1 (CRTC1).

The correlation between a cyclic AMP responsive element binding protein gene polymorphism and a phenotype can be examined as described in the following (1) to (4), for example.

(1) A gene polymorphism in a linkage disequilibrium block estimated as a result of a linkage disequilibrium analysis and a haplotype analysis in healthy subjects is selected. For example, a Tag SNP which is a typical gene polymorphism is selected as a cyclic AMP responsive element binding protein gene polymorphism for analyzing a correlation with a phenotype.

(2) Then, a gene polymorphism frequency of the gene polymorphism in test subjects (patients) is analyzed. In the case where a correlation between a gene polymorphism and disease vulnerability is examined, a comparison is made in terms of gene polymorphisms between the test subjects and the healthy subjects. It is effective to use a statistical technique such as a chi-square test in the comparison.

Here, the test subjects are classified into groups depending on the difference in phenotypes, and a comparison may be made in terms of gene polymorphism frequencies or genotypes between healthy subjects and test subjects in each group. In the case where the phenotype associated with the occurrence of a disease is a stimulant-induced psychotic-like symptom, it can be classified, for example, according to a period of time from the start of the use of a stimulant to the occurrence of delusion or hallucination, a period of duration of delusion or hallucination after termination of the use thereof; the presence or absence of the relapse, and the presence or absence of multiple drug abuse.

(3) If there is a gene polymorphism significantly linked to drug sensitivity in the test subjects, the gene polymorphism can be used for evaluating the genetic predisposition to drug sensitivity. Further, if there is a gene polymorphism with a significant difference in the gene polymorphism frequency between the healthy subjects and the test subjects, the gene polymorphism can be used for evaluating the genetic predisposition to disease vulnerability.

However, it is suggested that a tendency to gene polymorphism would be affected by the race, birthplace or the like, therefore, it is preferred that in a group showing a similar gene polymorphism to that of a population used for finding an associated gene polymorphism (such as SNP), the above-mentioned evaluation using the gene polymorphism is carried out.

Specific examples of the correlation between a cyclic AMP responsive element binding protein gene polymorphism and a phenotype will be shown in the following (1) to (4).

(1) In the correlation with the measurement results of the required total administration amount of analgesic in 24 hours after surgery, in the case of patients who had a minor allele (C) of the CREB1 subtype gene polymorphism (rs10932200) and underwent the surgery, the required administration amount (logarithmic transformation) of analgesic after the surgery was statistically significantly high in correlation with the number of alleles which they had. Thus, by analyzing the CREB1 subtype gene polymorphism (rs10932200), the sensitivity to analgesic can be more easily predicted.

(2) In the correlation with the measurement results of pain perception latency due to finger immersion in ice water before surgery, the presence or absence of a minor allele (C) of the CREB1 subtype gene polymorphism (rs10932200) and pain perception latency (logarithmic transformation) showed a significant correlation. Thus, by analyzing the CREB1 subtype gene polymorphism (rs10932200), the sensitivity to pain can be more easily predicted.

(3) In the correlation with the measurement results of the scale of the intensity of pain (VAS: on visual analogue scale) 24 hours after surgery, in the case of patients who had a minor allele (C) of the CREB1 subtype gene polymorphism (rs10932200) and underwent the surgery, the value of VAS (logarithmic transformation) was statistically significantly high in correlation with the number of alleles which they had. Thus, by analyzing the CREB1 subtype gene polymorphism (rs10932200), the sensitivity to pain or analgesic after the surgery can be more easily predicted.

(4) In the correlation with the measurement results of a difference in threshold of pain perception latency due to finger immersion in ice water before surgery, in the case of patients who had a minor allele (C) of the ATF2 subtype gene polymorphism (rs7583431) and underwent the surgery, a difference in threshold of pain perception latency (logarithmic transformation) due to finger immersion in ice water was statistically significantly short in correlation with the number of alleles which they had. Thus, by analyzing the ATF2 subtype gene polymorphism (rs7583431), the sensitivity to analgesic before the surgery can be more easily predicted.

5. Use of Analysis Results

As in the above-mentioned 4, the correlation between a cyclic AMP responsive element binding protein gene polymorphism and a phenotype analyzed can be used as an index in a method of predicting sensitivity to various drugs associated with the opioid receptor and the cyclic AMP responsive element binding protein and also to pain, a method of selecting a method of treating or preventing a disease associated with the opioid receptor and the cyclic AMP responsive element binding protein, a method of determining an appropriate administration amount of therapeutic drugs, a method of predicting side effects, or the like.

Further, by using the gene polymorphism or the method of the present invention, it is possible to evaluate drug sensitivity and disease vulnerability in different races. The subjects are not particularly limited, and examples thereof include Japanese, Europeans, Americans and the like. In the present invention, however, they are preferably Japanese or those having a similar gene polymorphism tendency to that of Japanese.

6. Detection of Gene Polymorphism

A genome sample of a test subject can be extracted from the blood, saliva, skin or the like, however, the origin is not limited to these as long as a genome sample can be collected therefrom. The extraction and purification methods of genomic DNA are publicly well known. For example, genomic DNA is purified from a specimen such as the blood, saliva, skin or the like collected from a human using the phenol method or the like. At this time, a commercially available genomic DNA extraction kit such as GFX Genomic Blood DNA Purification Kit (manufactured by GE Healthcare Bio-Sciences KK) or a device may be used. In the case where SNP to be detected is present in an exon, mRNA or total RNA may be extracted instead of genomic DNA.

In the detection of a cyclic AMP responsive element binding protein gene polymorphism in a genome sample, the above-mentioned oligonucleotide of the present invention can be used as a probe or a primer. Hereinafter, an example of the gene polymorphism detection method will be described.

(1) Detection of Gene Polymorphism by PCR Method

In order to amplify a test sample by PCR, it is preferred that a high fidelity DNA polymerase, for example, KOD Dash polymerase (manufactured by TOYOBO) is used. A primer to be used is designed such that a target SNP in the test sample can be amplified and synthesis is carried out. It is preferred that a gene polymorphism or a strand complementary thereto is contained at a given position between the forward and reverse primers. After completion of the amplification reaction, detection of the amplified products is carried out, and the presence or absence of a gene polymorphism is determined by a sequence method or the like.

(2) Detection of Gene Polymorphism by Sequencing Method

The gene polymorphism of the present invention can also be detected by a sequencing method based on the dideoxy method. As a sequencer to be used for the sequencing, a commercially available ABI series (Applied Biosystems (Life Technologies)) can be used.

(3) Detection of Gene Polymorphism Using DNA Microarray

A DNA microarray is a microarray in which oligonucleotide probes have been immobilized on a support, and includes a DNA chip, a Gene chip, a microchip, a bead array and the like. First, a polynucleotide of a test sample is isolated and amplified by PCR, and then labeled with a fluorescent reporter group. Then, a labeled DNA/mRNA, or total RNA is incubated along with an array.

Then, this array is inserted in a scanner, and a hybridization pattern is detected. The data of the hybridization is collected as emitted light from the fluorescent reporter group bound to the probe array (i.e., incorporated in a target sequence). A probe which is completely identical with the target sequence generates a stronger signal than those having a region which is not identical with the target sequence. Because the sequence and the position of each probe on the array are known, the sequence of the target polynucleotide reacted with the probe array can be determined based on the complementarity.

(4) Detection of Gene Polymorphism by TaqMan PCR Method

The TaqMan PCR method is a method utilizing an allele specific oligonucleotide (also referred to as TaqMan probe) labeled with fluorescence and PCR with Taq DNA polymerase. The allele specific oligonucleotide is an oligonucleotide containing a gene polymorphic site. The allele specific oligonucleotide to be used in the TaqMan PCR method can be designed based on the above-mentioned gene polymorphism information.

(5) Detection of Gene Polymorphism by Invader Method

The invader method is a method of detecting a gene polymorphism by subjecting an allele specific oligonucleotide and a template to hybridization. A kit for carrying out the invader method is commercially available (for example, NanoInvader® Array (manufactured by BML, Inc.)), and it is possible to easily detect a gene polymorphism by this method.

7. Kit

The present invention provides a kit for evaluating drug sensitivity and disease vulnerability. The kit for detecting a gene polymorphism of the present invention includes one or more components necessary for carrying out the present invention.

For example, the kit of the present invention preferably includes a component for storing or supplying an enzyme and/or a reaction component necessary for detecting a gene polymorphism. Such a component is not limited, and examples thereof include the oligonucleotide of the present invention, an enzyme buffer solution, dNTP, a reagent for control (such as a tissue sample or a target oligonucleotide for a positive or negative control), a reagent for labeling and/or detection, a solid phase support, a written instruction manual and the like. Further, the kit of the present invention may be a partial kit including only a part of the necessary components. In this case, a user can prepare the other components.

The kit of the present invention can be provided as a microarray in which the above-mentioned oligonucleotide has been immobilized on a support. The microarray is one in which the oligonucleotide of the present invention has been immobilized on a support, and includes a DNA chip, a Gene chip, a microchip, a bead array and the like.

The kit of the present invention preferably includes an oligonucleotide which contains a cyclic AMP responsive element binding protein gene polymorphism found in the present invention and is capable of being specifically hybridized to a DNA fragment containing the gene polymorphism.

In the case where a gene polymorphism is determined using the kit of the present invention, for example, the blood is collected before drugs are applied to patients or the like (for example, before surgery, at the time of occurrence of cancer pain or the like), and DNA containing a cyclic AMP responsive element binding protein 1 gene is isolated. Then, this gene is reacted with an oligonucleotide in the kit, and thereby a genotype is determined.

From the determined genotype and gene polymorphism, a dosage regimen such as the type or administration amount of the drugs can be designed. As a result, an effect of the drugs suitable for an individual can be obtained, which is useful in the personalized medicine. For example, in the case of using morphine, it becomes possible to obtain an analgesic effect suitable for an individual, and also to suppress the side effects to the minimum.

Hereinafter, the present invention will be described in more detail with reference to Examples. However, the present invention is not limited to these.

Example 1

<SNP Analysis and Haplotype Construction>
(SNP Analysis)

Genomic DNA was extracted from the blood of humans (127 Japanese healthy subjects) by a standard method, and gene polymorphisms were identified in four subtypes (CREB1, CREB3, CREB5, and ATF2) of a human cyclic AMP responsive element binding protein.

With regard to the CREB1 subtype gene, an entire exon region, 5' and 3' flanking regions, and an intron region were analyzed. In the case of the CREB1 subtype gene, 7 gene polymorphisms in an intron region were identified in the Japanese samples. Further, 4 and 6 gene polymorphisms were found in the 5' and 3' flanking regions, respectively (see Table 15). As a result of linkage disequilibrium analysis, 1 linkage disequilibrium block was found in a region ranging from the 5' flanking region to the 3' flanking region (see FIG. 1 and FIG. 2). It was found that rs16839837, rs2360969, rs10932200, rs2551946, rs4234080 and rs7594560 were suitable as Tag SNPs representing this linkage disequilibrium block.

Further, in the same manner as above, with regard to the CREB3 subtype gene, an entire exon region, 5' and 3' flanking regions, and an intron region were analyzed. In the case of the CREB3 subtype gene, 1 gene polymorphism in an intron region, and 25 and 14 gene polymorphisms in the 5' and 3' flanking regions, respectively, were identified in the Japanese samples (see Table 15). As a result of linkage disequilibrium analysis, 1 linkage disequilibrium block was found in the 5' flanking region, and 1 linkage disequilibrium block was found in a region ranging from the 5' flanking region to the 3' flanking region (see FIG. 3 and FIG. 4). It was found that rs1243872, rs2145925, rs2025126, GA007477, rs11541908, rs3763630, rs10814274, rsGA025684, rs10814275, rs4878628 and rs10758321 were suitable as Tag SNPs representing this linkage disequilibrium block.

Further, in the same manner as above, with regard to the CREB5 subtype gene, an entire exon region, 5' and 3' flanking regions, and an intron region were analyzed. In the case of the CREB5 subtype gene, 2 gene polymorphisms in a noncoding region of exon, 241 gene polymorphisms in an intron region, and 9 and 5 gene polymorphisms in the 5' and 3' flanking regions, respectively, were identified in the Japanese samples (see Table 16). As a result of linkage disequilibrium analysis performed on some of the aforementioned gene polymorphisms, 1 linkage disequilibrium block was found in the 5' flanking region, 15 linkage disequilibrium blocks were found in the intron region, and 1 linkage disequilibrium block was found in a region ranging from the noncoding region of exon to the 3' flanking region (see FIG. 5 and FIG. 6). It was found that rs4722778, rs177479, rs177486, rs177498, rs10229500, rs10243659, rs4722785, rs11772815, rs16874525, rs17715174, rs6953524, rs10239810, rs17156649, rs1811248, rs887623, rs740988, rs6952227, rs42695, rs1029897, rs10233653, rs6955105, rs17156699, rs177572, rs177573, rs177580, rs177581, rs12666636, rs1008262, rs310353, rs41273, rs1637457, rs17156919, rs41276, rs160375, rs17157048, rs6462098, rs10951201, rs13311248, rs10265166, rs6972081, rs12533079, rs7806547, rs6462100, rs6979352, rs721993, rs2237351 and rs3735566 were suitable as Tag SNPs representing this linkage disequilibrium block.

Further, in the same manner as above, with regard to the ATF2 subtype gene, an entire exon region, 5' and 3' flanking regions, and an intron region were analyzed. In the case of the ATF2 subtype gene, 1 gene polymorphism in a noncoding region of exon 1, 16 gene polymorphisms in an intron region, and 11 and 6 gene polymorphisms in the 5' and 3' flanking regions, respectively, were identified in the Japanese samples (see Table 15). As a result of linkage disequilibrium analysis, 1 linkage disequilibrium block was found in a region ranging from the 5' flanking region to the intron region, and 1 linkage disequilibrium block was found in the 3' flanking region (see FIG. 7 and FIG. 8). It was found that rs1153711, rs1153702, rs7583431, rs2302663, rs3845744, rs268214 and rs1982235 were suitable as Tag SNPs representing this linkage disequilibrium block.

TABLE 15

| | CREB1 gene polymorphism | | | | CREB3 gene polymorphism | | | | ATF2 gene polymorphism | | |
|---|---|---|---|---|---|---|---|---|---|---|---|
| Position | Gene polymorphism name | Major allele: minor allele | Minor allele frequency | Position | Gene polymorphism name | Major allele: minor allele | Minor allele frequency | Position | Gene polymorphism name | Major allele: minor allele | Minor allele frequency |
| 5' Flanking region | rs16839837 | C:T | 0.232 | 5' Flanking region | rs1243872 | G:T | 0.449 | 5' Flanking region | rs268174 | C:T | 0.201 |
| | rs2360969 | C:T | 0.126 | | rs2145925 | C:T | 0.39 | | rs13030474 | G:T | 0.008 |
| | rs1093220 | A:C | 0.315 | | rs2025126 | G:A | 0.366 | | rs268237 | C:T | 0.189 |
| | rs2253206 | G:A | 0.315 | | rs1885373 | T:C | 0.055 | | rs1982235 | T:G | 0.398 |
| Intron | rs2551640 | A:G | 0.323 | | rs1885374 | A:C | 0.051 | | rs10497435 | T:C | 0.189 |
| | rs11904814 | T:G | 0.319 | | GA007473 | T:C | 0.051 | | rs268231 | C:A | 0.197 |
| | rs16839883 | A:G | 0.181 | | rs2295794 | T:C | 0.453 | | rs268230 | A:C | 0.197 |
| | rs6740584 | C:T | 0.307 | | rs4879926 | T:C | 0.051 | | rs268229 | G:A | 0.197 |
| | rs3770704 | T:C | 0.181 | | GA007477 | C:T | 0.358 | | rs268228 | A:G | 0.205 |
| | rs2254137 | A:C | 0.323 | | rs867194 | T:C | 0.028 | | rs166531 | T:C | 0.189 |
| | rs2551645 | T:C | 0.319 | | rs11541908 | C:T | 0.283 | | rs268214 | T:C | 0.189 |
| 3' Flanking region | rs2551946 | C:A | 0.02 | | rs741917 | C:T | 0.028 | Exon | rs10497434 | T:C | 0.154 |
| | rs4234080 | C:A | 0.193 | | rs7862485 | G:A | 0.051 | Intron | rs11888507 | C:T | 0.154 |
| | rs2952768 | T:C | 0.331 | | rs2756894 | C:A | 0.445 | | rs13388308 | C:T | 0.154 |
| | rs2709386 | G:A | 0.331 | | rs2249250 | T:G | 0.425 | | rs3755490 | T:C | 0.146 |
| | rs7591784 | G:A | 0.331 | | rs2295795 | G:A | 0.374 | | rs7578569 | G:A | 0.154 |
| | rs7594560 | T:C | 0.181 | | rs877365 | T:C | 0.445 | | rs7566401 | C:A | 0.154 |
| | | | | | rs2737273 | G:A | 0.413 | | rs1153676 | C:A | 0.154 |

TABLE 15-continued

| | CREB1 gene polymorphism | | | | CREB3 gene polymorphism | | | | ATF2 gene polymorphism | | |
|---|---|---|---|---|---|---|---|---|---|---|---|
| Position | Gene polymorphism name | Major allele: minor allele | Minor allele frequency | Position | Gene polymorphism name | Major allele: minor allele | Minor allele frequency | Position | Gene polymorphism name | Major allele: minor allele | Minor allele frequency |
| | | | | | rs2295797 | T:C | 0.374 | | rs1205399 | A:C | 0.169 |
| | | | | | rs2295798 | C:T | 0.008 | | rs2072538 | C:T | 0.146 |
| | | | | | rs1534847 | A:G | 0.37 | | rs212361 | A:G | 0.154 |
| | | | | | rs7873822 | G:T | 0.417 | | rs212360 | T:C | 0.154 |
| | | | | | rs2737274 | G:A | 0.051 | | rs1153685 | A:G | 0.154 |
| | | | | | rs10972587 | A:C | 0.445 | | rs12693057 | G:A | 0.154 |
| | | | | | rs3763630 | C:T | 0.276 | | rs212347 | T:C | 0.154 |
| | | | | Intron | rs10814274 | C:T | 0.409 | | rs212349 | T:C | 0.154 |
| | | | | 3' Flanking region | rs3750434 | G:A | 0.402 | | rs3845744 | A:G | 0.291 |
| | | | | | rs1570246 | G:T | 0.385 | | rs2302663 | G:A | 0.146 |
| | | | | | GA025684 | G:C | 0.323 | 3' Flanking region | rs35507277 | T:G | 0.008 |
| | | | | | rs1570248 | T:C | 0.268 | | rs1153699 | C:T | 0.472 |
| | | | | | rs1570249 | G:A | 0.409 | | rs1153700 | C:G | 0.425 |
| | | | | | rs34478611 | G:A | 0.323 | | rs7583431 | A:C | 0.366 |
| | | | | | rs1322045 | A:G | 0.268 | | rs1153702 | T:C | 0.476 |
| | | | | | rs1951432 | G:A | 0.26 | | rs1153711 | T:G | 0.209 |
| | | | | | GA025687 | A:T | 0.264 | | | | |
| | | | | | rs10814275 | A:G | 0.067 | | | | |
| | | | | | rs10758320 | T:C | 0.264 | | | | |
| | | | | | rs4878628 | C:T | 0.134 | | | | |
| | | | | | rs10758321 | G:A | 0.394 | | | | |
| | | | | | rs10758322 | C:T | 0.402 | | | | |

TABLE 16

| | CREB5 gene polymorphism | | | | CREB5 gene polymorphism | | | | CREB5 gene polymorphism | | |
|---|---|---|---|---|---|---|---|---|---|---|---|
| Position | Gene polymorphism name | Major allele: minor allele | Minor allele frequency | Position | Gene polymorphism name | Major allele: minor allele | Minor allele frequency | Position | Gene polymorphism name | Major allele: minor allele | Minor allele frequency |
| 5' Flanking region | rs4722778 | C:G | 0.256 | Intron | rs177576 | T:C | 0.327 | Intron | rs41320 | C:T | 0.323 |
| | rs177479 | T:C | 0.252 | | rs177578 | G:A | 0.012 | | rs41321 | A:G | 0.402 |
| | rs177480 | A:G | 0.242 | | rs13437706 | C:T | 0.374 | | rs41322 | A:G | 0.335 |
| | rs11981754 | A:G | 0.008 | | rs177580 | C:T | 0.382 | | rs7780656 | G:T | 0.063 |
| | rs177486 | G:A | 0.161 | | rs177581 | C:T | 0.169 | | rs41327 | A:G | 0.343 |
| | rs177498 | C:T | 0.248 | | rs12666636 | C:A | 0.224 | | rs42322 | T:C | 0.331 |
| | rs849322 | A:G | 0.437 | | rs177584 | G:A | 0.169 | | rs41333 | A:G | 0.331 |
| | rs177505 | T:G | 0.201 | | rs177585 | C:T | 0.169 | | rs9655280 | A:G | 0.063 |
| | rs2175738 | G:A | 0.161 | | rs177588 | G:A | 0.098 | | rs9655281 | G:A | 0.063 |
| Intron | rs4719932 | A:C | 0.016 | | rs6462088 | G:A | 0.437 | | rs4719945 | A:G | 0.307 |
| | rs10258745 | C:T | 0.031 | | rs7796539 | C:T | 0.004 | | rs6945988 | A:G | 0.413 |
| | rs1013900 | G:T | 0.021 | | rs1859020 | A:G | 0.378 | | rs10258405 | T:G | 0.185 |
| | rs6955393 | G:A | 0.035 | | rs1011384 | A:G | 0.236 | | rs10243376 | G:A | 0.185 |
| | rs6953880 | A:G | 0.02 | | rs6462090 | G:T | 0.004 | | rs41334 | T:C | 0.429 |
| | rs17156573 | T:C | 0.035 | | rs12671247 | T:C | 0.154 | | rs10245004 | C:T | 0.189 |
| | rs6960209 | C:T | 0.02 | | rs217508 | T:C | 0.398 | | rs41339 | G:T | 0.317 |
| | rs17156577 | T:C | 0.039 | | rs4719936 | G:T | 0.004 | | rs982947 | C:T | 0.181 |
| | rs7811922 | A:C | 0.035 | | rs217509 | G:T | 0.197 | | rs982950 | A:G | 0.181 |
| | rs6973453 | T:C | 0.201 | | rs217510 | T:C | 0.193 | | rs16874653 | A:G | 0.28 |
| | rs17156579 | C:T | 0.055 | | rs17718257 | G:A | 0.004 | | rs41346 | G:T | 0.02 |
| | rs1073298 | T:C | 0.201 | | rs149591 | C:A | 0.051 | | rs41348 | A:G | 0.396 |
| | rs6961801 | C:T | 0.319 | | rs1910553 | C:A | 0.22 | | rs9989149 | C:T | 0.339 |
| | rs6977728 | C:A | 0.106 | | rs217517 | G:A | 0.193 | | rs6968464 | G:A | 0.02 |
| | rs6978238 | C:T | 0.102 | | rs217519 | G:A | 0.173 | | rs886816 | G:A | 0.181 |
| | rs13230543 | C:A | 0.248 | | rs2391668 | T:G | 0.382 | | rs757980 | A:G | 0.035 |
| | rs12673465 | A:G | 0.343 | | rs4722804 | G:T | 0.189 | | rs41351 | A:G | 0.093 |
| | rs10251129 | T:C | 0.327 | | rs618776 | A:G | 0.378 | | rs96918763 | A:C | 0.098 |
| | rs2391656 | T:C | 0.333 | | rs217503 | C:T | 0.382 | | rs17157048 | A:C | 0.087 |
| | rs6971345 | A:G | 0.327 | | rs217513 | C:T | 0.236 | | rs6462098 | T:C | 0.122 |
| | rs17156603 | A:G | 0.398 | | rs65264 | C:T | 0.394 | | rs10951201 | C:A | 0.154 |
| | rs7806362 | C:A | 0.173 | | rs441355 | G:T | 0.189 | | rs13311248 | G:C | 0.146 |

TABLE 16-continued

| | CREB5 gene polymorphism | | | | CREB5 gene polymorphism | | | | CREB5 gene polymorphism | | |
|---|---|---|---|---|---|---|---|---|---|---|---|
| Position | Gene polymorphism name | Major allele: minor allele | Minor allele frequency | Position | Gene polymorphism name | Major allele: minor allele | Minor allele frequency | Position | Gene polymorphism name | Major allele: minor allele | Minor allele frequency |
| | rs17642145 | T:C | 0.008 | | rs2391670 | C:T | 0.362 | | rs12540480 | T:C | 0.063 |
| | rs10229500 | C:T | 0.138 | | rs2391671 | A:G | 0.362 | | rs10265166 | G:T | 0.043 |
| | rs10243659 | C:A | 0.476 | | rs216708 | A:G | 0.425 | | rs7798774 | T:C | 0.087 |
| | rs4722785 | G:A | 0.488 | | rs11980665 | C:T | 0.173 | | rs7799246 | T:C | 0.056 |
| | rs16874503 | C:T | 0.004 | | rs11980669 | C:T | 0.173 | | rs6972081 | T:C | 0.287 |
| | rs11772815 | G:A | 0.331 | | rs11984308 | T:C | 0.173 | | rs7777929 | T:C | 0.037 |
| | rs6958133 | G:A | 0.13 | | rs160346 | G:A | 0.37 | | rs12533079 | T:G | 0.079 |
| | rs16874525 | C:T | 0.461 | | rs150607 | A:G | 0.276 | | rs7806547 | G:A | 0.157 |
| | rs17715174 | G:C | 0.354 | | rs177594 | G:A | 0.106 | | rs6462100 | G:A | 0.134 |
| | rs10242868 | T:G | 0.205 | | rs6969064 | A:G | 0.169 | | rs6979352 | C:T | 0.012 |
| | rs12709884 | G:A | 0.476 | | rs150610 | A:G | 0.094 | | rs6950574 | A:G | 0.13 |
| | rs17156635 | G:A | 0.189 | | rs216715 | T:C | 0.287 | | rs4722835 | A:C | 0.13 |
| | rs10239606 | C:T | 0.374 | | rs10951197 | T:C | 0.39 | | rs9648352 | A:G | 0.028 |
| | rs16874528 | G:A | 0.008 | | rs12539927 | A:G | 0.185 | | rs879593 | A:C | 0.138 |
| | rs7799687 | C:A | 0.189 | | rs216720 | A:G | 0.951 | | rs879591 | G:T | 0.15 |
| | rs714218 | G:A | 0.327 | | rs17156823 | G:A | 0.252 | | rs2299110 | C:T | 0.228 |
| | rs1860759 | A:G | 0.327 | | rs2078980 | G:A | 0.492 | | rs2237349 | C:T | 0.272 |
| | rs997908 | G:A | 0.476 | | rs216730 | T:G | 0.236 | | rs2066979 | T:C | 0.275 |
| | rs12112050 | C:T | 0.484 | | rs13228899 | G:T | 0.201 | | rs10486589 | A:G | 0.039 |
| | rs2191827 | A:G | 0.484 | | rs160335 | G:A | 0.496 | | rs10486591 | G:A | 0.272 |
| | rs4498447 | T:C | 0.327 | | rs10951200 | G:A | 0.047 | | rs6462103 | C:T | 0.118 |
| | rs10254657 | G:A | 0.449 | | rs10486588 | G:A | 0.461 | | rs721993 | C:T | 0.154 |
| | rs6953524 | G:T | 0.492 | | rs216735 | G:A | 0.287 | | rs2237351 | T:C | 0.091 |
| | rs10239810 | A:G | 0.307 | | rs216737 | C:T | 0.031 | | rs740315 | G:A | 0.004 |
| | rs17156649 | G:A | 0.079 | | rs216743 | G:A | 0.055 | | rs2237353 | A:C | 0.238 |
| | rs1811248 | T:G | 0.13 | | rs216744 | A:G | 0.055 | | rs2073537 | T:C | 0.217 |
| | rs887623 | T:C | 0.252 | | rs216747 | C:T | 0.031 | | rs4722844 | G:T | 0.181 |
| | rs740988 | A:G | 0.276 | | rs1976489 | A:G | 0.496 | | rs17730621 | C:T | 0.327 |
| | rs7794304 | T:C | 0.457 | | rs150613 | C:T | 0.169 | | rs2282907 | G:A | 0.24 |
| | rs42694 | A:G | 0.035 | | rs17156878 | G:A | 0.232 | | rs10238623 | G:A | 0.193 |
| | rs6952227 | G:A | 0.291 | | rs767834 | C:G | 0.437 | | rs2299116 | C:A | 0.091 |
| | rs42695 | C:T | 0.244 | | rs4722820 | G:A | 0.177 | | rs2299117 | T:C | 0.154 |
| | rs1029897 | T:C | 0.409 | | rs160337 | C:A | 0.047 | | rs2237355 | A:G | 0.368 |
| | rs42699 | A:C | 0.024 | | rs160338 | G:A | 0.075 | | rs2237360 | T:G | 0.268 |
| | rs4722793 | C:A | 0.405 | | rs1008262 | T:C | 0.323 | | rs2237361 | T:C | 0.217 |
| | rs735101 | T:C | 0.409 | | rs310353 | G:A | 0.299 | | rs2237362 | T:C | 0.106 |
| | rs10233653 | G:A | 0.421 | | rs310359 | T:C | 0.217 | | rs7791555 | G:T | 0.272 |
| | rs6955105 | G:A | 0.465 | | rs310361 | C:T | 0.169 | | rs2237364 | A:G | 0.26 |
| | rs2286841 | C:A | 0.228 | | rs13233942 | A:G | 0.339 | | rs2282909 | T:G | 0.366 |
| | rs979915 | C:T | 0.012 | | rs310338 | T:C | 0.323 | | rs2282910 | C:T | 0.366 |
| | rs7794347 | C:T | 0.248 | | rs41273 | G:A | 0.169 | | rs2282911 | T:C | 0.366 |
| | rs16874562 | G:T | 0.283 | | rs1637457 | A:G | 0.22 | | rs1544470 | A:G | 0.362 |
| | rs17156685 | A:G | 0.087 | | rs17156919 | G:A | 0.299 | | rs1964240 | A:C | 0.293 |
| | rs174024 | C:T | 0.268 | | rs41276 | A:G | 0.417 | | rs17669844 | T:C | 0.008 |
| | rs6949786 | G:A | 0.26 | | rs160375 | A:G | 0.067 | | rs886750 | A:G | 0.354 |
| | rs7793437 | A:G | 0.016 | | rs917275 | A:G | 0.067 | | rs12531253 | G:A | 0.272 |
| | rs3757677 | T:C | 0.016 | | rs160342 | A:G | 0.264 | | rs10951205 | A:G | 0.374 |
| | rs6462085 | T:G | 0.016 | | rs160343 | T:C | 0.083 | Exon | rs2190305 | A:G | 0.374 |
| | rs17717216 | T:C | 0.016 | | rs41295 | C:T | 0.094 | | rs3735566 | G:A | 0.039 |
| | rs17156694 | G:A | 0.441 | | rs160357 | A:G | 0.492 | 3' | rs11975539 | G:A | 0.039 |
| | rs17156699 | A:G | 0.268 | | rs41298 | G:A | 0.236 | Flanking | rs6462107 | C:T | 0.039 |
| | rs177572 | T:C | 0.331 | | rs41305 | G:A | 0.402 | region | rs2190306 | T:C | 0.043 |
| | rs177573 | T:C | 0.417 | | rs41307 | C:T | 0.425 | | rs4719955 | T:C | 0.047 |
| | rs6977204 | A:G | 0.48 | | rs10228740 | A:G | 0.126 | | rs10228137 | C:A | 0.051 |
| | rs177574 | A:G | 0.047 | | rs3888613 | G:A | 0.205 | | | | |

In Table 15 and Table 16, there is not found any polymorphism causing amino acid substitution, namely, a polymorphism in which the type of amino acid after translation is changed depending on the gene polymorphism allele.

Moreover, in Table 15 and Table 16, "minor allele frequency" means the ratio of a minor allele. It is to be noted that the number of healthy subjects used as test subjects was 127.

(Haplotype Construction)

As some examples of haplotype analysis, with regard to the 17 sites of SNPs which are CREB1 subtype gene polymorphisms, the 40 sites of SNPs which are CREB3 subtype gene polymorphisms, the 83 sites of SNPs which are CREB5 subtype gene polymorphisms, and the 23 sites of SNPs which are ATF2 subtype gene polymorphisms, as shown in Table 15 and Table 16, among the cyclic AMP responsive element binding protein gene polymorphisms in Japanese healthy subjects, a haplotype was estimated for each linkage disequilibrium block (haplotype block), using Haploview. The estimated haplotypes are shown in Tables 17, 18, 19 and 20. It is to be noted that the "Tag" used in each table means a Tag SNP that is a representative gene polymorphism in the linkage disequilibrium block.

TABLE 17

Gene name CREB1

| Hap-lotype No. | Frequency (%) | Linkage disequilibrium block No. 1 Gene polymorphism name (※) | | | | | | | | | | | | | | | |
|---|---|---|---|---|---|---|---|---|---|---|---|---|---|---|---|---|---|
| | | 1 Tag | 2 Tag | 3 Tag | 4 | 5 | 6 | 7 | 8 | 9 | 10 | 11 | 12 Tag | 13 Tag | 14 | 15 | 16 | 17 Tag |
| H1 | 16.9 | C | C | C | A | G | G | G | T | C | C | C | C | C | C | A | A | T |
| H2 | 42.5 | C | C | A | G | A | T | A | C | T | A | T | C | C | T | G | G | T |
| H3 | 12.2 | C | T | C | A | G | G | A | T | T | C | C | C | C | C | A | A | T |
| H4 | 17.7 | T | C | A | G | A | T | A | C | T | A | T | C | A | T | G | G | C |
| H5 | 1.6 | C | C | A | G | A | T | A | C | T | A | T | A | C | C | A | A | T |
| H6 | 3.5 | T | C | A | G | A | T | A | C | T | A | T | C | C | T | G | G | T |
| H7 | 1.2 | T | C | A | G | A | T | A | C | T | A | T | C | A | T | G | G | T |
| ... | | Haplotypes which are estimated to occur at a frequency of less than 1% | | | | | | | | | | | | | | | | |
| 合計 | 100.0% | | | | | | | | | | | | | | | | | |

(※) 1~17: (in this order)rs16839837, rs2360969, rs10932200, rs2253206, rs2551640, rs11904814, rs16839883, rs6740584, rs3770704, rs2254137, rs2551645, rs2551946, rs4234080, rs2952768, rs2709386, rs7591784 and rs7594560

TABLE 18

Gene name CREB3

| Hap-lotype No. | Frequency (%) | Linkage disequilibrium block No. 1 Gene polymorphism name (※) | | | | | | | | | | | | | | | | | | | | | | |
|---|---|---|---|---|---|---|---|---|---|---|---|---|---|---|---|---|---|---|---|---|---|---|---|---|
| | | 1 Tag | 2 Tag | 3 Tag | 4 | 5 | 6 | 7 | 8 | 9 Tag | 10 | 11 Tag | 12 | 13 | 14 | 15 | 16 | 17 | 18 | 19 | 20 | 21 | 22 | 23 | 24 |
| H1 | 18.9 | G | C | G | T | A | T | T | T | C | T | C | C | G | C | T | G | T | G | T | C | A | G | G | A |
| H2 | 35.4 | G | C | G | T | A | T | T | T | T | T | C | C | G | C | T | G | T | G | T | C | A | G | G | A |
| H3 | 25.6 | T | T | A | T | A | T | C | T | C | T | T | C | G | A | G | A | C | A | C | C | G | T | G | C |
| H4 | 8.3 | T | T | A | T | A | T | C | T | C | T | C | C | G | A | G | A | C | A | C | C | G | T | G | C |
| H5 | 4.3 | T | C | G | C | C | C | C | C | C | T | C | C | A | A | G | G | C | A | T | C | A | T | A | C |
| H6 | 2.8 | T | T | G | T | A | T | C | T | C | C | C | T | G | A | T | G | C | G | T | C | A | G | G | C |
| H7 | 1.2 | T | C | A | T | A | T | C | T | C | T | T | C | G | A | G | A | C | A | C | C | G | T | G | C |
| ... | | Haplotypes which are estimated to occur at a frequency of less than 1% | | | | | | | | | | | | | | | | | | | | | | |
| 合計 | 100.0% | | | | | | | | | | | | | | | | | | | | | | | |

| Hap-lotype No. | Frequency (%) | Linkage disequilibrium block No. 2 Gene polymorphism name (※) | | | | | | | | | | | | | | | |
|---|---|---|---|---|---|---|---|---|---|---|---|---|---|---|---|---|---|
| | | 25 Tag | 26 Tag | 27 | 28 | 29 Tag | 30 | 31 | 32 | 33 | 34 | 35 | 36 Tag | 37 | 38 Tag | 39 Tag | 40 |
| H8 | 12.6 | C | C | G | G | G | C | G | G | G | A | T | A | C | C | G | C |
| H9 | 29.8 | C | T | A | T | G | T | A | G | A | G | A | A | T | C | A | T |
| H10 | 25.9 | T | C | G | G | C | T | G | A | A | G | A | A | T | C | G | C |
| H11 | 2.0 | C | T | A | G | G | T | A | G | A | G | A | A | T | C | G | T |
| H12 | 6.4 | C | C | G | G | C | T | G | A | A | G | A | A | T | C | G | C |
| H13 | 6.7 | C | T | A | T | G | T | A | G | A | G | A | G | T | C | A | T |
| H14 | 12.2 | C | C | G | G | G | C | G | G | G | A | T | A | C | T | G | C |
| ... | | Haplotypes which are estimated to occur at a frequency of less than 1% | | | | | | | | | | | | | | | |
| 合計 | 100.0% | | | | | | | | | | | | | | | | |

(※) 1~40: (in this order)rs1243872, rs2145925, rs2025126, rs1885373, rs1885374, GA007473, rs2295794, rs4879926, GA007477, rs867194, rs11541908, rs741917, rs7862485, rs2756894, rs2249250, rs2295795, rs877365, rs2737273, rs2296797, rs2295798, rs1534847, rs7873822, rs273274, rs10972567, rs3763630, rs10814274, rs3750434, rs1570246, GA025684, rs1570248, rs1570249, rs34478611, rs1322045, rs1951432, GA025687, rs10814275, rs10758320, rs4878628, rs10758321 and rs10758322

TABLE 19

Gene name CREB5

Linkage disequilibrium block No. 1

| Haplotype (H) No. | Frequency (%) | 1 Tag | 2 Tag | 3 Tag | 4 Tag | 5 Tag | 6 Tag | H No. |
|---|---|---|---|---|---|---|---|---|
| H1 | 73.2 | G | T | A | A | G | C | H6 |
| H2 | 6.7 | G | C | G | A | G | T | H7 |
| H3 | 16.1 | C | C | G | A | A | T | H8 |
| H4 | 1.2 | C | C | G | A | G | T | H9 |
| H5 | 1.2 | G | C | G | A | G | C | H10 |
| ... | 100.0% | | | | | | | |

Linkage disequilibrium block No. 6

Gene polymorphism name (X)

| Haplotype (H) No. | Frequency (%) | 7 Tag | 8 Tag | 9 Tag | 10 Tag | 11 Tag | Frequency (%) | 12 Tag | H No. |
|---|---|---|---|---|---|---|---|---|---|
| H1 | 13.1 | C | C | G | C | A | 48.1 | G | H11 |
| H2 | 13.9 | C | A | A | C | G | 35.4 | G | H12 |
| H3 | 16.5 | C | A | A | C | G | 18.5 | G | H13 |
| H4 | 12.8 | T | A | A | C | G | | A | ... |
| H5 | 2.0 | C | C | A | G | G | 100.0% | G | |
| ... | | | | | | | | | |

Haplotypes which are estimated to occur at a frequency of less than 1%

Linkage disequilibrium block No. 8

| Haplotype (H) No. | Frequency (%) | 13 Tag | 14 Tag | H No. | Frequency (%) | 15 Tag | 16 Tag | H No. |
|---|---|---|---|---|---|---|---|---|
| H1 | 49.2 | T | G | H14 | 87.0 | T | A | H17 |
| H2 | 50.1 | C | C | H15 | 5.1 | C | A | H18 |
| H3 | 30.3 | C | G | H16 | 7.9 | C | G | H19 |
| ... | | | | | 100.0% | | | |

Linkage disequilibrium block No. 9 / 10

| Haplotype (H) No. | Frequency (%) | 17 Tag | 18 Tag |
|---|---|---|---|
| H1 | | G | T |
| H2 | | G | G |
| H3 | | A | G |

Linkage disequilibrium block No. 11

Gene polymorphism name (X)

| Haplotype (H) No. | Frequency (%) | 19 Tag | 20 Tag | H No. | Frequency (%) | 21 Tag | 22 Tag | 23 Tag | H No. |
|---|---|---|---|---|---|---|---|---|---|
| H20 | 71.2 | T | A | H24 | 40.1 | G | C | C | H28 |
| H21 | 3.4 | T | G | H25 | 6.4 | G | C | T | H29 |
| H22 | 24.0 | C | G | H26 | 28.7 | A | C | T | H30 |
| H23 | 1.2 | C | A | H27 | 24.0 | G | T | T | ... |
| ... | 100.0% | | | | 100.0% | | | | |

Haplotypes which are estimated to occur at a frequency of less than 1%

Linkage disequilibrium block No. 13

| Haplotype (H) No. | Frequency (%) | 24 Tag | 25 Tag | H No. | Frequency (%) | 26 Tag | 27 Tag | 28 Tag | H No. |
|---|---|---|---|---|---|---|---|---|---|
| | 42.1 | A | A | H31 | 26.8 | G | T | C | H35 |
| | 4.3 | G | A | H32 | 33.1 | A | C | T | H36 |
| | 53.5 | G | G | H33 | 25.2 | A | T | T | H37 |
| | | | | H34 | 15.0 | A | T | C | H38 |
| | 100.0% | | | | 100.0% | | | | |

Linkage disequilibrium block No. 15 / 16

| | 29 Tag | 30 Tag | 31 Tag | 32 | 33 |
|---|---|---|---|---|---|
| | C | C | C | G | C |
| | T | G | A | G | C |
| | C | C | A | G | C |
| | T | T | C | A | T |

Linkage disequilibrium block No. 25

Gene polymorphism name (X)

| Haplotype (H) No. | Frequency (%) | 34 Tag | 35 Tag | H No. | Frequency (%) | 36 Tag | 37 Tag | 38 Tag | 39 Tag | H No. | Frequency (%) | 40 Tag | 41 Tag | H No. |
|---|---|---|---|---|---|---|---|---|---|---|---|---|---|---|
| H39 | 29.9 | T | A | H42 | 41.7 | G | A | G | G | H47 | 93.2 | A | A | H49 |
| H40 | 32.3 | C | G | H43 | 29.5 | G | A | A | A | H48 | 8.7 | G | G | H50 |

Linkage disequilibrium block No. 26 / 27

| | 42 Tag | 43 Tag | 44 Tag | 45 Tag | 46 Tag | 47 Tag | 48 | 49 | 50 Tag |
|---|---|---|---|---|---|---|---|---|---|
| | A | T | C | G | T | G | T | T | T |
| | A | T | C | G | T | G | T | T | C |

TABLE 19-continued

Gene name CREB5

| Hap-lotype (H) No. | 37.8 | T | G | H44 H45 H46 ... | 16.3 6.3 5.1 | A G G | G A G | A G G | A A A | ... | | | | | | | | | | | | | |
|---|---|---|---|---|---|---|---|---|---|---|---|---|---|---|---|---|---|---|---|---|---|---|
| H41 ... | | | | | | | | | | | | | | | | | | | | | | | |

100.0%  100.0%

Haplotypes which are estimated to occur at a frequency of less than 1%
100.0%

Linkage disequilibrium block No. 33

| Hap-lotype (H) No. | Frequency (%) | 51 Tag | 52 Tag | 53 Tag |
|---|---|---|---|---|
| H56 | 83.4 | T | G | G |
| H57 | 1.2 | T | A | A |
| H58 | 7.5 | G | A | A |
| H59 | 2.8 | T | A | G |
| H60 | 4.3 | T | A | A |

100.0%

Linkage disequilibrium block No. 35

Gene polymorphism name (Ж)

| | 54 Tag | 55 | 56 | H No. | Frequency (%) | 57 Tag | 58 Tag | H No. | Frequency (%) | 59 Tag | 60 | 61 | 62 | 63 | 64 |
|---|---|---|---|---|---|---|---|---|---|---|---|---|---|---|---|
| | C | A | A | H61 | 84.6 | C | T | H65 | 94.5 | G | G | C | T | T | C |
| | T | G | C | H62 | 9.1 | T | C | H65 | 3.9 | A | A | T | C | G | A |
| | C | G | C | H63 | 6.3 | T | T | ... | | | | | | | |
| | C | A | A | ... | | | | | | | | | | | |
| | C | G | C | | | | | | | | | | | | |

Haplotypes which are estimated to occur at a frequency of less than 1%
100.0%  100.0%

Linkage disequilibrium block No. 40

(Ж) 1–64: (in this order) rs4722778, rs1774479, rs1774480, rs11981754, rs1774486, rs1774498, rs177480, rs10229500, rs10243659, rs1774503, rs1774525, rs16874525, rs17715174, rs6953524, rs6958133, rs16874503, rs1772815, rs6958133, rs16874525, rs17715174, rs6953524, rs6958133, rs16874503, rs1772815, rs6958133, rs10239810, rs17156649, rs17156649, rs1811248, rs887623, rs740988, rs6952227, rs42695, rs1029897, rs10233653, rs6955105, rs17156699, rs10265166, rs10540480, rs12540480, rs1774573, rs1774573, rs1774581, rs1774584, rs1774585, rs1777581, rs1008262, rs310353, rs1637457, rs17156919, rs917275, rs160375, rs41276, rs17157048, rs6462098, rs10951201, rs13311248, rs12540480, rs1774573, rs1774573, rs1774581, rs1774584, rs1774585, rs1777581, rs1008262, rs310353, rs1637457, rs17156919, rs917275, rs160375, rs41276, rs17157048, rs6462098, rs10951201, rs13311248, rs12540480, rs12533079, rs7806547, rs7799248, rs4972081, rs4972081, rs4722835, rs6950574, rs6979352, rs6950574, rs6950574, rs6979352, rs6462100, rs6462107, rs2190306, rs4719955 and rs10228137

TABLE 20

Gene name ATF2

Linkage disequilibrium block No.

Linkage disequilibrium block No. 1

Gene polymorphism name (X)

| Haplotype No. | Frequency (%) | 1 Tag | 2 Tag | 3 Tag | 4 Tag | 5 Tag | 6 | 7 | 8 | 9 | 10 | 11 | 12 | 13 | 14 | 15 | 16 |
|---|---|---|---|---|---|---|---|---|---|---|---|---|---|---|---|---|---|
| H1 | 26.3 | T | C | A | A | G | C | C | A | G | C | G | T | C | A | A | A |
| H2 | 20.9 | G | C | A | G | G | T | T | G | A | T | A | C | A | C | C | G |
| H3 | 36.2 | T | T | C | G | A | T | T | G | A | T | A | C | A | C | C | G |
| H4 | 16.2 | T | T | A | G | A | T | T | G | A | T | A | C | A | C | C | G |
| ... | | | | | G | G | T | T | G | A | T | A | C | A | C | C | G |
| | 100.0% | Haplotypes which are estimated to occur at a frequency of less than 1% | | | | | | | | | | | | | | | |

Linkage disequilibrium block No. 2

Gene polymorphism name (X)

| Haplotype No. | Frequency (%) | 17 | 18 | 19 | 20 | 21 Tag | 22 | 23 | 24 | 25 | 26 | 27 | 28 Tag | 29 | 30 | 31 |
|---|---|---|---|---|---|---|---|---|---|---|---|---|---|---|---|---|
| H5 | 14.6 | C | T | T | C | C | C | G | A | C | A | C | T | T | C | T |
| H6 | 8.8 | T | C | C | T | T | T | A | G | A | C | T | G | C | G | C |
| H7 | 40.3 | T | C | C | T | T | T | A | G | A | C | T | T | C | G | C |
| H8 | 28.3 | T | C | C | T | T | T | A | G | A | C | T | G | C | G | C |
| H9 | 4.3 | T | C | C | T | C | C | G | A | C | A | C | T | T | G | T |
| ... | | Haplotypes which are estimated to occur at a frequency of less than 1% | | | | | | | | | | | | | | |
| | 100.0% | | | | | | | | | | | | | | | |

(X) 1~31: (in this order)rs1153711, rs1153702, rs7583431, rs2302663, rs3845744, s212349, rs212347, rs12693057, rs1153685, rs212360, rs212361, rs2072538, rs1205399, rs1153676, rs7566401, rs7578569, rs3755490, rs13388308, rs11888507, rs10497434, rs268214, rs166531, rs268228, rs268229, rs268230, rs268231, rs10497435, rs1982235, rs268237, rs13030474 and rs268174

As shown in Table 17, at least 7 haplotypes were estimated as the haplotype of CREB1 subtype gene polymorphism in the Japanese healthy subjects, and among these, there were 6 haplotypes observed at a high frequency of 3% or higher (haplotype Nos. H1 to H6). Incidentally, specific description regarding haplotypes which are estimated to occur at a frequency of less than 1% was omitted from Table 17.

In addition, as shown in Table 18, at least 14 haplotypes were estimated as the haplotype of CREB3 subtype gene polymorphism in the Japanese healthy subjects, and among these, there were 11 haplotypes observed at a high frequency of 3% or higher (haplotype Nos. H1 to H5, H8 to H10, and H12 to H14). Incidentally, specific description regarding haplotypes which are estimated to occur at a frequency of less than 1% was omitted from Table 18.

Moreover, as shown in Table 19, at least 65 haplotypes were estimated as the haplotype of CREB5 subtype gene polymorphism in the Japanese healthy subjects, and among these, there were 57 haplotypes observed at a high frequency of 3% or higher (haplotype Nos. H1 to H3, H6 to H9, H11 to H22, H24 to H36, H38 to H54, H56, H58, and H60 to H65). Incidentally, specific description regarding haplotypes which are estimated to occur at a frequency of less than 1% was omitted from Table 19.

Furthermore, as shown in Table 20, at least 9 haplotypes were estimated as the haplotype of ATF2 subtype gene polymorphism in the Japanese healthy subjects, and among these, there were 9 haplotypes observed at a high frequency of 3% or higher (haplotype Nos. H1 to H9). Incidentally, specific description regarding haplotypes which are estimated to occur at a frequency of less than 1% was omitted from Table 20.

Figure 2:
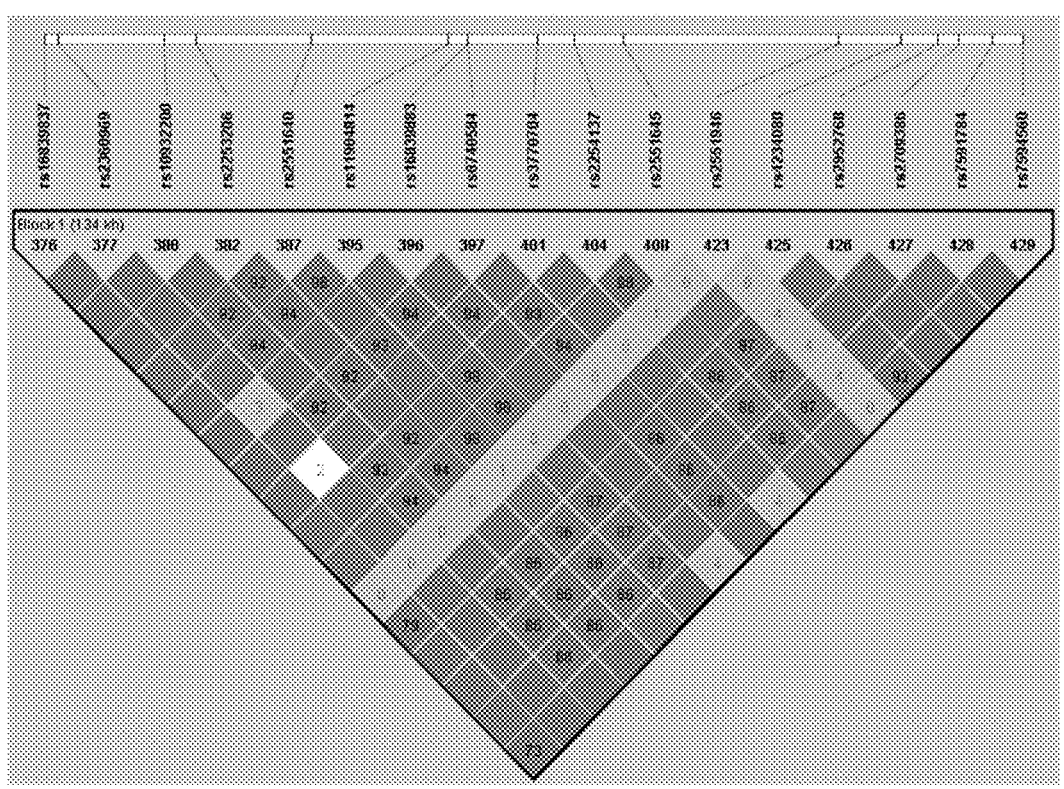
FIG. 2 is a schematic view showing gene polymorphisms identified regarding a CREB1 subtype gene and a linkage disequilibrium found among them. In the figure, high-color squares indicate SNPs showing strong linkage with each other. In addition, the square found at the intersection of squares continued from each SNP to the lower left direction or the lower right direction indicates the calculation value (percentage) of $r^2$ that is an index of the linkage disequilibrium of a SNP and another SNP. For example, the calculation value of $r^2$ between rs16839837 and rs2551640 is 0.12.
Figure 3:
FIG. 3 is a schematic view showing gene polymorphisms identified regarding a CREB3 subtype gene and a linkage disequilibrium found among them. In the figure, high-color squares indicate SNPs showing strong linkage with each other. In addition, the square found at the intersection of squares continued from each SNP to the lower left direction or the lower right direction indicates the calculation value (percentage) of D' that is an index of the linkage disequilibrium of a SNP and another SNP. For example, the calculation value of D' between rs1243872 and rs2025126 is 0.97.
Figure 4:
FIG. 4 is a schematic view showing gene polymorphisms identified regarding a CREB3 subtype gene and a linkage disequilibrium found among them. In the figure, high-color squares indicate SNPs showing strong linkage with each other. In addition, the square found at the intersection of squares continued from each SNP to the lower left direction or the lower right direction indicates the calculation value (percentage) of $r^2$ that is an index of the linkage disequilibrium of a SNP and another SNP. For example, the calculation value of $r^2$ between rs1243872 and rs2025126 is 0.67.
Figure 5:
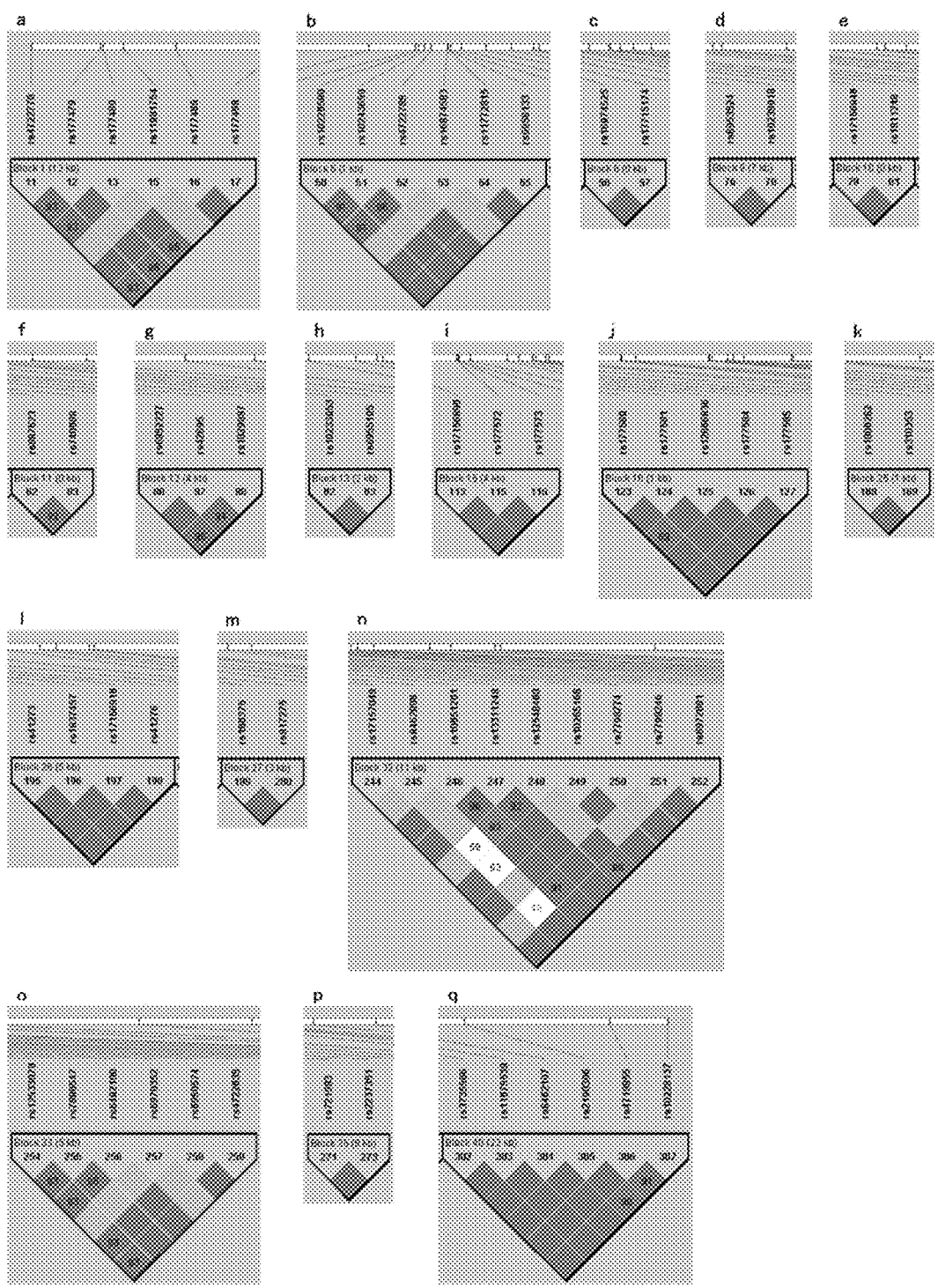
FIG. 5 is a schematic view showing gene polymorphisms identified regarding a CREB5 subtype gene and a linkage disequilibrium found among them. In the figure, high-color squares indicate SNPs showing strong linkage with each other. In addition, the square found at the intersection of squares continued from each SNP to the lower left direction or the lower right direction indicates the calculation value (percentage) of D' that is an index of the linkage disequilibrium of a SNP and another SNP. For example, the calculation value of D' between rs4722778 and rs177479 is 0.93.
Figure 6:
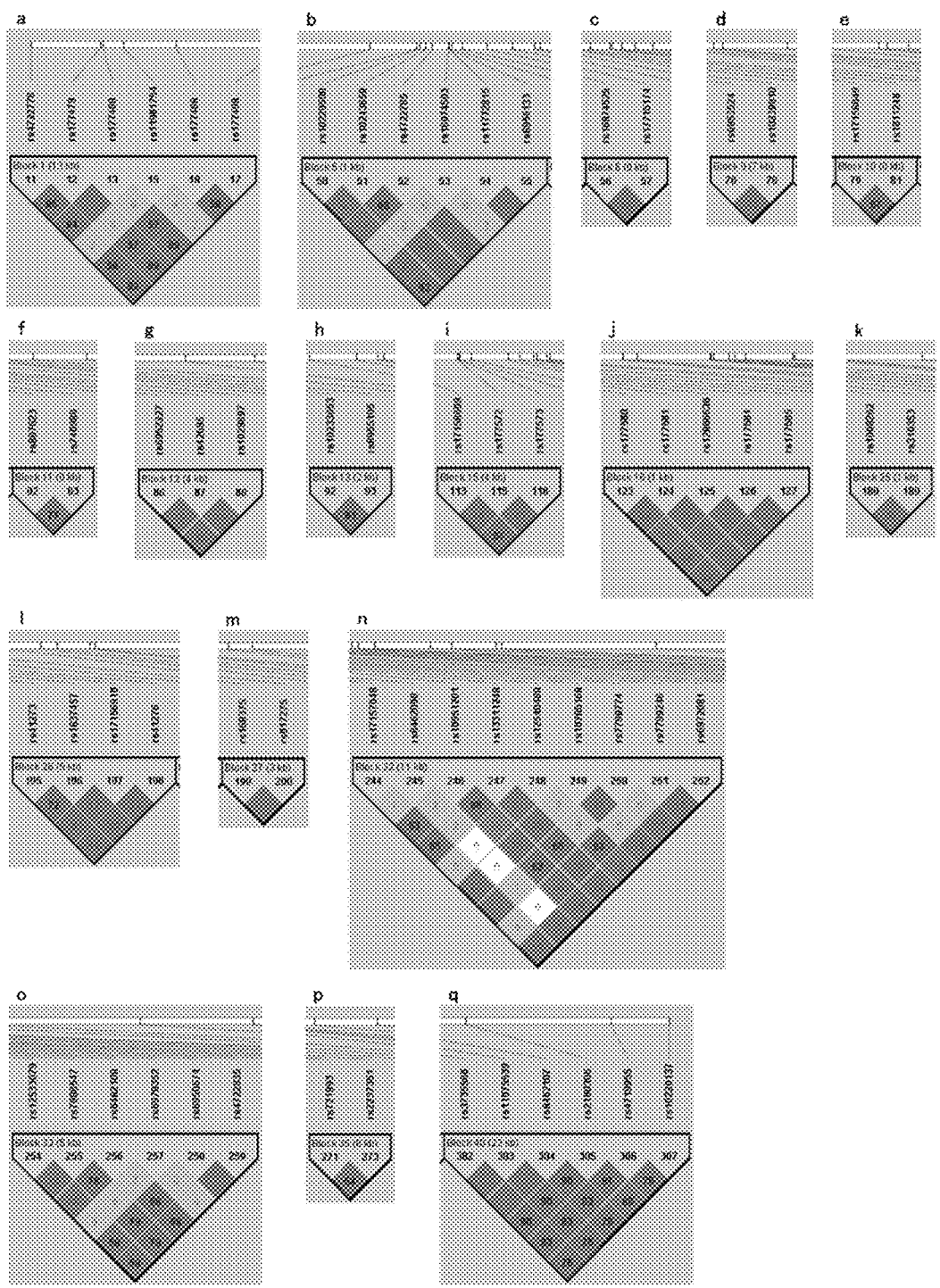
FIG. 6 is a schematic view showing gene polymorphisms identified regarding a CREB5 subtype gene and a linkage disequilibrium found among them. In the figure, high-color squares indicate SNPs showing strong linkage with each other. In addition, the square found at the intersection of squares continued from each SNP to the lower left direction or the lower right direction indicates the calculation value (percentage) of $r^2$ that is an index of the linkage disequilibrium of a SNP and another SNP. For example, the calculation value of $r^2$ between rs4722778 and rs177479 is 0.85.
Figure 7:
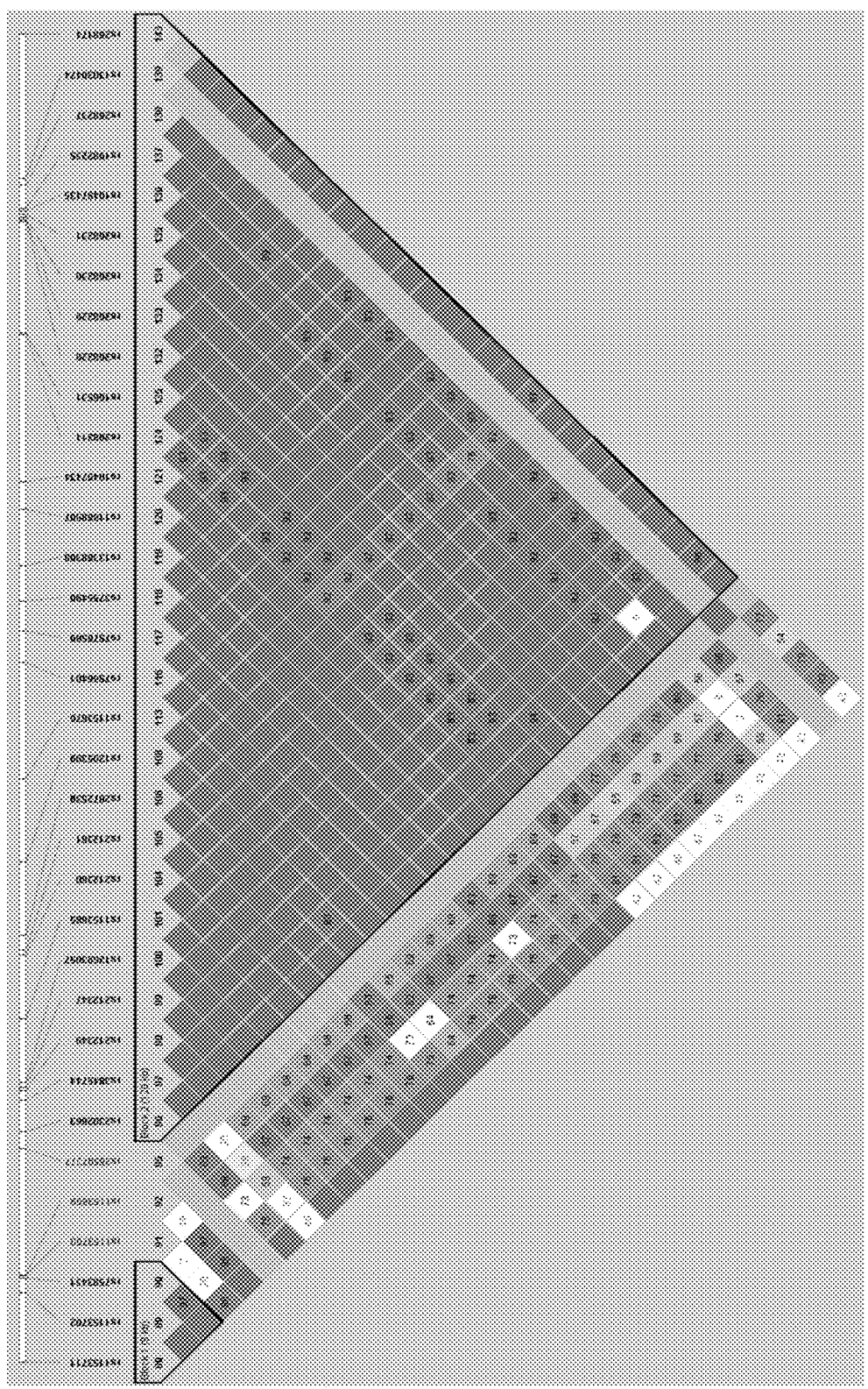
FIG. 7 is a schematic view showing gene polymorphisms identified regarding a ATF2 subtype gene and a linkage disequilibrium found among them. In the figure, high-color squares indicate SNPs showing strong linkage with each other. In addition, the square found at the intersection of squares continued from each SNP to the lower left direction or the lower right direction indicates the calculation value (percentage) of D' that is an index of the linkage disequilibrium of a SNP and another SNP. For example, the calculation value of D' between rs1153711 and rs1153700 is 0.86.
Figure 8:
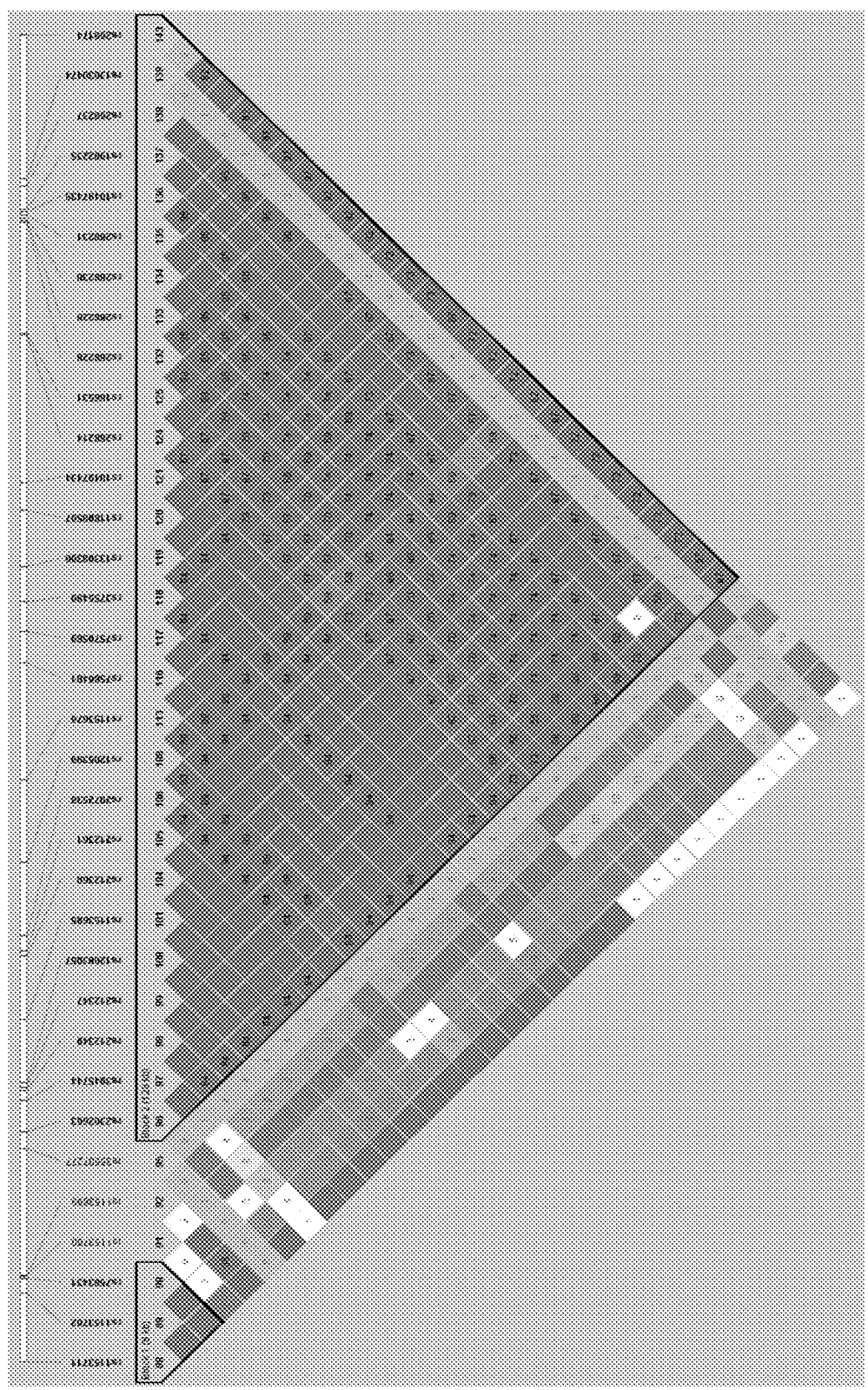
FIG. 8 is a schematic view showing gene polymorphisms identified regarding a ATF2 subtype gene and a linkage disequilibrium found among them. In the figure, high-color squares indicate SNPs showing strong linkage with each other. In addition, the square found at the intersection of squares continued from each SNP to the lower left direction or the lower right direction indicates the calculation value (percentage) of $r^2$ that is an index of the linkage disequilibrium of a SNP and another SNP. For example, the calculation value of $r^2$ between rs1153711 and rs1153700 is 0.14.

As well as an analysis of the haplotype frequencies in the haplotype analysis shown in Tables 17, 18, 19 and 20, a linkage disequilibrium analysis was carried out. The results are shown in FIG. 1 to FIG. 8. The linkage disequilibrium among the CREB1 subtype gene polymorphisms in the Japanese healthy subjects is shown in FIG. 1 and FIG. 2. In addition, the linkage disequilibrium among the CREB3 subtype gene polymorphisms in the Japanese healthy subjects is shown in FIG. 3 and FIG. 4. Moreover, the linkage disequilibrium among the CREB5 subtype gene polymorphisms in the Japanese healthy subjects is shown in FIG. 5 and FIG. 6. Furthermore, the linkage disequilibrium among the ATF2 subtype gene polymorphisms in the Japanese healthy subjects is shown in FIG. 7 and FIG. 8.

A linkage disequilibrium block was estimated from the results of the linkage disequilibrium analysis (FIG. 1 to FIG. 8) using Haploview.

In FIG. 1, a D' value, which is an index of a linkage disequilibrium between SNP and SNP, is calculated, and the resulting value (two places of decimals) is written in the square at the intersection of squares continued from each SNP to the lower left direction or the lower right direction. Further, an $r^2$ value, which is a more stringent index of the linkage disequilibrium, is calculated in the same manner, and the resulting value is written in the same square as defined above in FIG. 2. It is to be noted that the square in which no numbers are written indicates that the D' or $r^2$ value is 1. Also, the same shall apply to FIGS. 3 and 4, FIGS. 5 and 6, and FIGS. 7 and 8.

When focusing attention on the D' values in FIG. 1, a complete linkage disequilibrium (D'=1) was observed in many combinations of gene polymorphisms. Further, when focusing attention on the $r^2$ values in FIG. 2, it was found that several gene polymorphisms showed a strong linkage disequilibrium ($r^2$=1). It was found that suitable Tag SNPs representing these linkage disequilibrium blocks are rs16839837, rs2360969, rs10932200, rs2551946, rs4234080 and rs7594560.

In addition, when focusing attention on the D' values in FIG. 3, a complete linkage disequilibrium (D'=1) was observed in many combinations of gene polymorphisms. Further, when focusing attention on the $r^2$ values in FIG. 4, it was found that several gene polymorphisms showed a strong linkage disequilibrium ($r^2$=1). It was found that suitable Tag SNPs representing these linkage disequilibrium blocks are rs1243872, rs2145925, rs2025126, GA007477, rs11541908, rs3763630, rs10814274, rsGA025684, rs10814275, rs4878628 and rs10758321.

When focusing attention on the D' values in FIG. 5, a complete linkage disequilibrium (D'=1) was observed in many combinations of gene polymorphisms. Further, when focusing attention on the $r^2$ values in FIG. 6, it was found that several gene polymorphisms showed a strong linkage disequilibrium ($r^2$=1). It was found that suitable Tag SNPs representing these linkage disequilibrium blocks are rs4722778, rs177479, rs177486, rs177498, rs10229500, rs10243659, rs4722785, rs11772815, rs16874525, rs17715174, rs6953524, rs10239810, rs17156649, rs1811248, rs887623, rs740988, rs6952227, rs42695, rs1029897, rs10233653, rs6955105, rs17156699, rs177572, rs177573, rs177580, rs177581, rs12666636, rs1008262, rs310353, rs41273, rs1637457, rs17156919, rs41276, rs160375, rs17157048, rs6462098, rs10951201, rs13311248, rs10265166, rs6972081, rs12533079, rs7806547, rs6462100, rs6979352, rs721993, rs2237351 and rs3735566.

In addition, when focusing attention on the D' values in FIG. 7, a complete linkage disequilibrium (D'=1) was observed in many combinations of gene polymorphisms. Further, when focusing attention on the $r^2$ values in FIG. 8, it was found that several gene polymorphisms showed a strong linkage disequilibrium ($r^2$=1). It was found that suitable Tag SNPs representing these linkage disequilibrium blocks are rs1153711, rs1153702, rs7583431, rs2302663, rs3845744, rs268214 and rs1982235.

Further, a linkage disequilibrium block was estimated from the results of the linkage disequilibrium analysis (FIG. 1 to FIG. 8) using Haploview. As a result, with regard to SNP in the CREB1 subtype gene shown in FIG. 1 and FIG. 2, one linkage disequilibrium block was confirmed in a region ranging from the 5' flanking region to the 3' flanking region. In a similar manner, with regard to SNP in the CREB3 subtype gene shown in FIG. 3 and FIG. 4, one linkage disequilibrium block was confirmed in the 5' flanking region, and one linkage disequilibrium block was confirmed in a region ranging from the 5' flanking region to the 3' flanking region. In a similar manner, with regard to SNP in the CREB5 subtype gene shown in FIG. 5 and FIG. 6, one linkage disequilibrium block was confirmed in the 5' flanking region, 15 linkage disequilibrium blocks were confirmed in the intron region, and one linkage disequilibrium block was confirmed in a region ranging from the noncoding region of exon to the 3' flanking region. In a similar manner, with regard to SNP in the ATF2 subtype gene shown in FIG. 7 and FIG. 8, one linkage disequilibrium block was confirmed in a region ranging from the 5' flanking region to the intron region, and one linkage disequilibrium block was confirmed in the 3' flanking region.

Example 2

<Correlation Between CREB1 Subtype Gene Polymorphism (Rs10932200) and Required Administration Amount of Analgesic>

A correlation between a cyclic AMP responsive element binding protein gene polymorphism and the required administration amount of analgesic was examined. Genomic DNA was extracted from the blood of 247 patients undergoing surgery (orthognathic surgery), and one gene polymorphism (rs10932200) in the CREB1 subtype gene was determined. Then, a correlation between these results of determination of the gene polymorphism and the required administration amount of analgesic after the surgery was analyzed.

Incidentally, as the analgesic, fentanyl, which is mainly administered intravenously through a PCA (patient-controlled analgesia) pump, was used.

Figure 9:
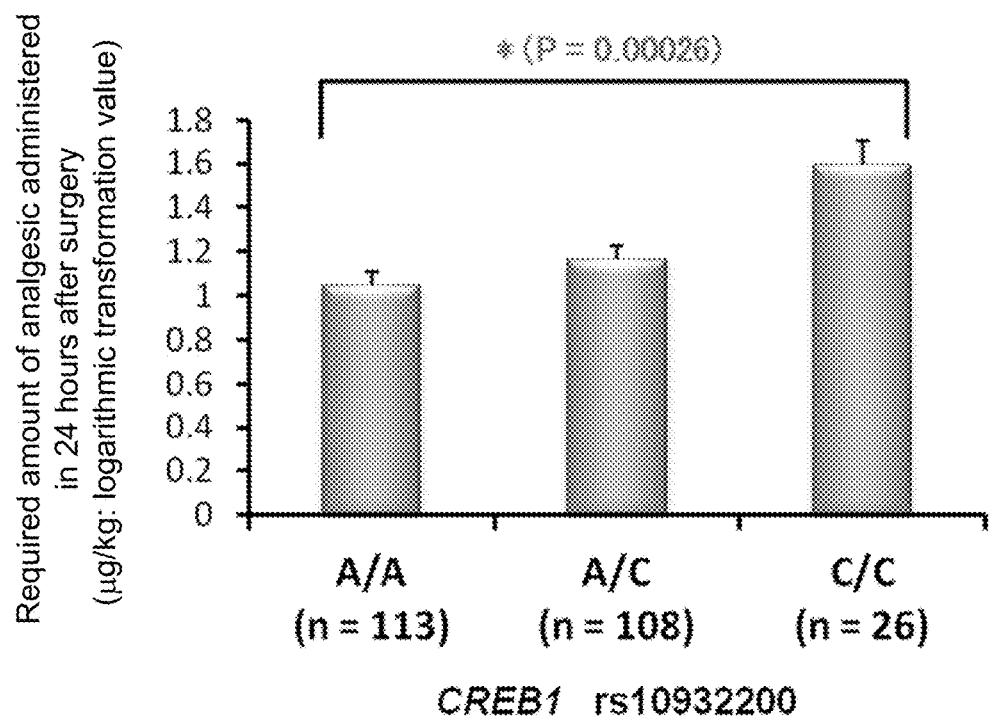
FIG. 9 is a graph showing the effect (overall average±standard deviation) of a polymorphism (rs10932200) of a CREB1 subtype gene on the required administration amount (μg/kg) of analgesic in 24 hours after surgery, in all patients who were administered with analgesic in the surgery (orthognathic surgery).

As a result, as shown in the following Table 21 and FIG. 9, in the case of patients who had a minor allele (C) of the CREB1 subtype gene polymorphism (rs10932200) and underwent the surgery, the required administration amount (logarithmic transformation) of analgesic after the surgery was statistically significantly high in correlation with the number of alleles which they had. Accordingly, by analyzing the CREB1 subtype gene polymorphism (rs10932200), the sensitivity to analgesic can be predicted.

Using the median (2.222 (μg/kg)) of the required administration amounts of fentanyl in 24 hours after the surgery as a reference, a patient group with a value smaller than the reference and a patient group with a value larger than the reference were defined as a "high analgesic sensitivity group" and a "low analgesic sensitivity group," respectively, and the groups were then stratified in terms of the rs10932200 polymorphism of the CREB1 gene. As a result, in terms of this polymorphism, 54% and 46% of patients were determined to belong to the high analgesic sensitivity group and the low analgesic sensitivity group, respectively, in the A/A patient group. In contrast, in the C/C patient group, 23% and 77% of patients were determined to belong to the high analgesic sensitivity group and the low analgesic sensitivity group, respectively.

TABLE 21

Effect of CREB1 rs10932200 polymorphism on required amount of analgesic administered in 24 hours after surgery in patients treated with analgesic in surgery (orthognathic surgery)(descriptive statistics by gender)

| CREB1 rs10932200 | Gender | Average X̄ | Standard deviation | Number of test subjects (subjects) |
|---|---|---|---|---|
| A/A | F | 2.47 | 2.06 | 77 |
| | M | 2.42 | 2.57 | 36 |
| | Total | 2.46 | 2.23 | 113 |
| A/C | F | 3.23 | 2.65 | 75 |
| | M | 2.05 | 1.97 | 33 |
| | Total | 2.87 | 2.51 | 108 |
| C/C | F | 4.37 | 3.32 | 13 |
| | M | 4.94 | 2.70 | 13 |
| | Total | 4.65 | 2.98 | 26 |
| Total | F | 2.96 | 2.50 | 165 |
| | M | 2.67 | 2.54 | 82 |
| | Total | 2.87 | 2.51 | 247 |

X̄:Required administration amount (μg/kg) of analgesic in 24 hours after surgery

Example 3

<Correlation Between CREB1 Subtype Gene Polymorphism (Rs10932200) and Pain Sensitivity>

A correlation between a cyclic AMP responsive element binding protein gene polymorphism and pain sensitivity was examined. Genomic DNA was extracted from the blood of 247 patients undergoing surgery (orthognathic surgery), and one gene polymorphism (rs10932200) in the CREB1 subtype gene was determined. Then, a correlation between these results of determination of the gene polymorphism and the measurement of pain perception latency due to finger immersion in ice water before the surgery was analyzed.

Figure 10:
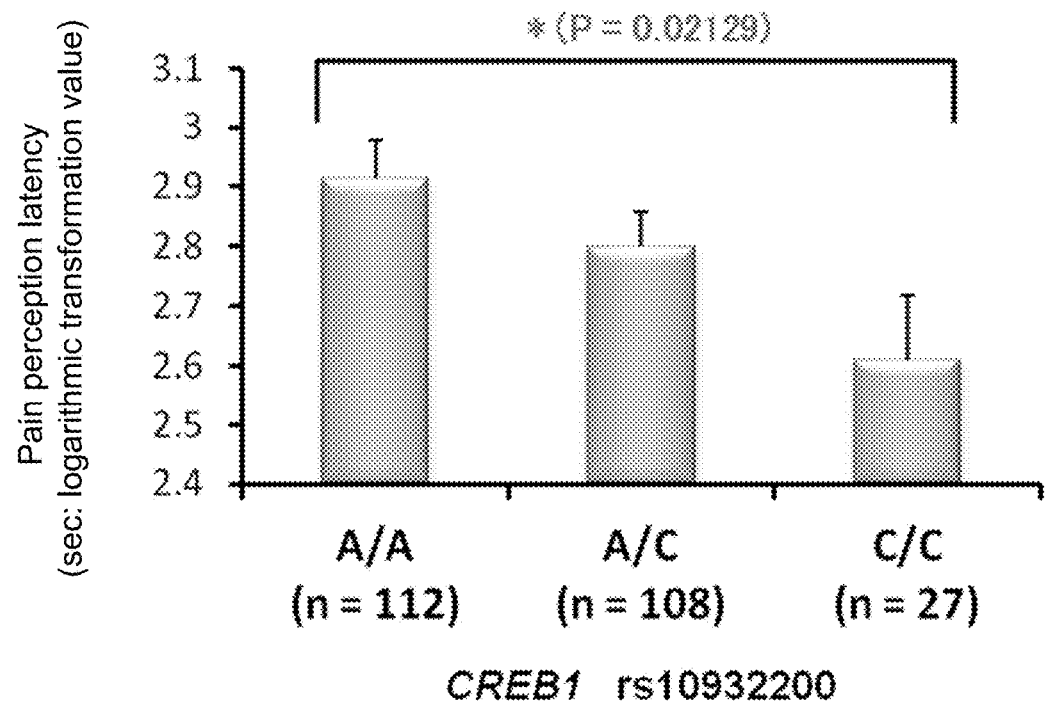
FIG. 10 is a graph showing the effect (overall average±standard deviation) of a polymorphism (rs10932200) of a CREB1 subtype gene on the measurement results (sec) of pain sensitivity before surgery, in all patients who were administered with analgesic in the surgery (orthognathic surgery).

As a result, as shown in the following Table 22 and FIG. 10, in the case of patients who had a minor allele (C) of the CREB1 subtype gene polymorphism (rs10932200) and underwent the surgery, the measurement result (logarithmic transformation) of pain perception latency was statistically significantly low in correlation with the number of alleles which they had. Accordingly, by analyzing the CREB1 subtype gene polymorphism (rs10932200), the sensitivity to pain can be predicted.

Using the median (15 sec) of the measurement results of pain perception latency due to finger immersion in ice water before the surgery as a reference, a patient group with a value smaller than the reference and a patient group with a value larger than the reference were defined as a "high pain sensitivity group" and a "low pain sensitivity group," respectively, and the groups were then stratified in terms of the rs10932200 polymorphism of the CREB1 gene. As a result, in terms of this polymorphism, 45% and 55% of patients were determined to belong to the high pain sensitivity group and the low pain sensitivity group, respectively, in the A/A patient group. In contrast, in the A/C or C/C patient group, 55% and 45% of patients were determined to belong to the high pain sensitivity group and the low pain sensitivity group, respectively.

TABLE 22

Effect of CREB1 rs10932200 polymorphism on measurement results of pain sensitivity before surgery in patients treated with analgesic in surgery (orthognathic surgery) (descriptive statistics by gender)

| CREB1 rs10932200 | Gender | Average ※ | Standard deviation | Number of test subjects (subjects) |
|---|---|---|---|---|
| A/A | F | 20.95 | 18.21 | 76 |
|  | M | 27.96 | 32.07 | 36 |
|  | Total | 23.20 | 23.65 | 112 |
| A/C | F | 17.83 | 15.13 | 75 |
|  | M | 21.91 | 17.12 | 33 |
|  | Total | 19.07 | 15.80 | 108 |
| C/C | F | 12.07 | 8.03 | 14 |
|  | M | 17.73 | 9.86 | 13 |
|  | Total | 14.80 | 9.24 | 27 |
| Total | F | 18.78 | 16.33 | 165 |
|  | M | 23.90 | 24.28 | 82 |
|  | Total | 20.48 | 19.43 | 247 |

※Measurement (sec) of pain perception latency due to finger immersion in ice water before surgery

Example 4

<Correlation Between CREB1 Subtype Gene Polymorphism (Rs10932200) and Pain Sensitivity>

A correlation between a cyclic AMP responsive element binding protein gene polymorphism and pain sensitivity was examined. Genomic DNA was extracted from the blood of 247 patients undergoing surgery (orthognathic surgery), and one gene polymorphism (rs10932200) in the CREB1 subtype gene was determined. Then, a correlation between these results of determination of the gene polymorphism and the measurement of the scale of the intensity of pain (VAS: on visual analogue scale) 24 hours after the surgery was analyzed.

Figure 11:
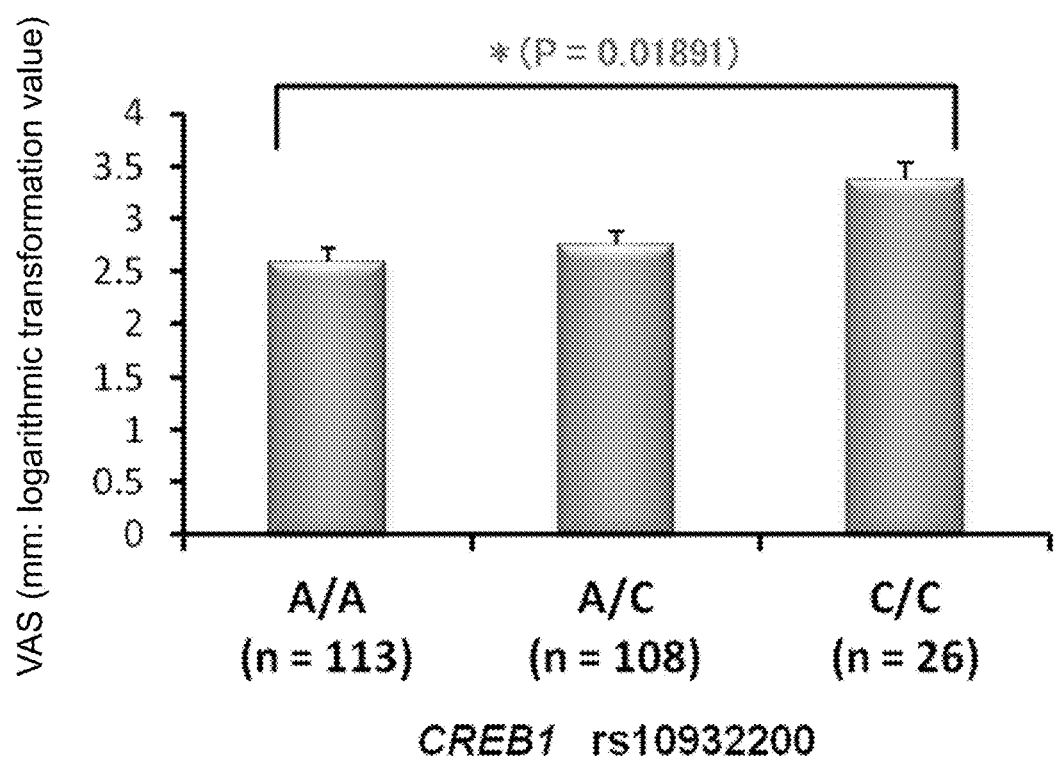
FIG. 11 is a graph showing the effect (overall average±standard deviation) of a polymorphism (rs10932200) of a CREB1 subtype gene on the measurement results (mm) of VAS (the intensity of pain on a visual analogue scale) 24 hours after surgery, in male patients who were administered with analgesic in the surgery (orthognathic surgery).

As a result, as shown in the following Table 23 and FIG. 11, in correlation with the measurement result (logarithmic transformation) of the scale of the intensity of pain (VAS) 24 hours after the surgery, patients who had a minor allele (T) of the CREB1 subtype gene polymorphism (rs10932200) and underwent the surgery had a value of VAS (logarithmic transformation) that was statistically significantly high in correlation with the number of alleles which they had. Accordingly, by analyzing the CREB1 subtype gene polymorphism (rs10932200), the sensitivity to pain or analgesic after the surgery can be more easily predicted.

Using the median (24 mm) of the VAS values 24 hours after the surgery as a reference, a patient group with a value smaller than the reference and a patient group with a value larger than the reference were defined as a "low pain sensitivity group" and a "high pain sensitivity group," respectively, and the groups were then stratified in terms of the rs10932200 polymorphism of the CREB1 gene. As a result, in terms of this polymorphism, 54% and 46% of patients were determined to belong to the low pain sensitivity group and the high pain sensitivity group, respectively, in the A/A patient group. In contrast, in the A/C or C/C patient group, 47% and 53% of patients were determined to belong to the low pain sensitivity group and the high pain sensitivity group, respectively.

TABLE 23

Effect of CRB1 rs10932200 polymorphism on measurement results of VAS (intensity of pain on visual analogue scale) after surgery in patients administered with analgesic in surgery (orthognathic surgery)(descriptive statistics by gender)

| CREB1 rs10932200 | Gender | Average ※ | Standard deviation | Number of test subjects (subjects) |
|---|---|---|---|---|
| A/A | F | 24.17 | 19.35 | 77 |
|  | M | 21.94 | 18.59 | 36 |
|  | Total | 23.46 | 19.06 | 113 |
| A/C | F | 28.51 | 24.49 | 75 |
|  | M | 26.33 | 20.06 | 33 |
|  | Total | 27.84 | 23.15 | 108 |
| C/C | F | 37.31 | 17.78 | 13 |
|  | M | 34.31 | 21.78 | 13 |
|  | Total | 35.81 | 19.54 | 26 |
| Total | F | 27.18 | 21.92 | 165 |
|  | M | 25.67 | 19.92 | 82 |
|  | Total | 26.68 | 21.25 | 247 |

※Measurement (mm) of scale of intensity of pain by VAS after surgery

Example 5

<Correlation Between ATF2 Subtype Gene Polymorphism (Rs7583431) and Analgesic Effect of Fentanyl>

A correlation between a cyclic AMP responsive element binding protein gene polymorphism and pain sensitivity was examined. Genomic DNA was extracted from the blood of 247 patients undergoing surgery (orthognathic surgery), and one gene polymorphism (rs7583431) in the ATF2 subtype gene was determined. Then, a correlation between these results of determination of the gene polymorphism and the analgesic effect of fentanyl that was evaluated based on the measurement of a difference in threshold of pain perception latency due to finger immersion in ice water after administration of an analgesic before the surgery was analyzed.

Figure 12:
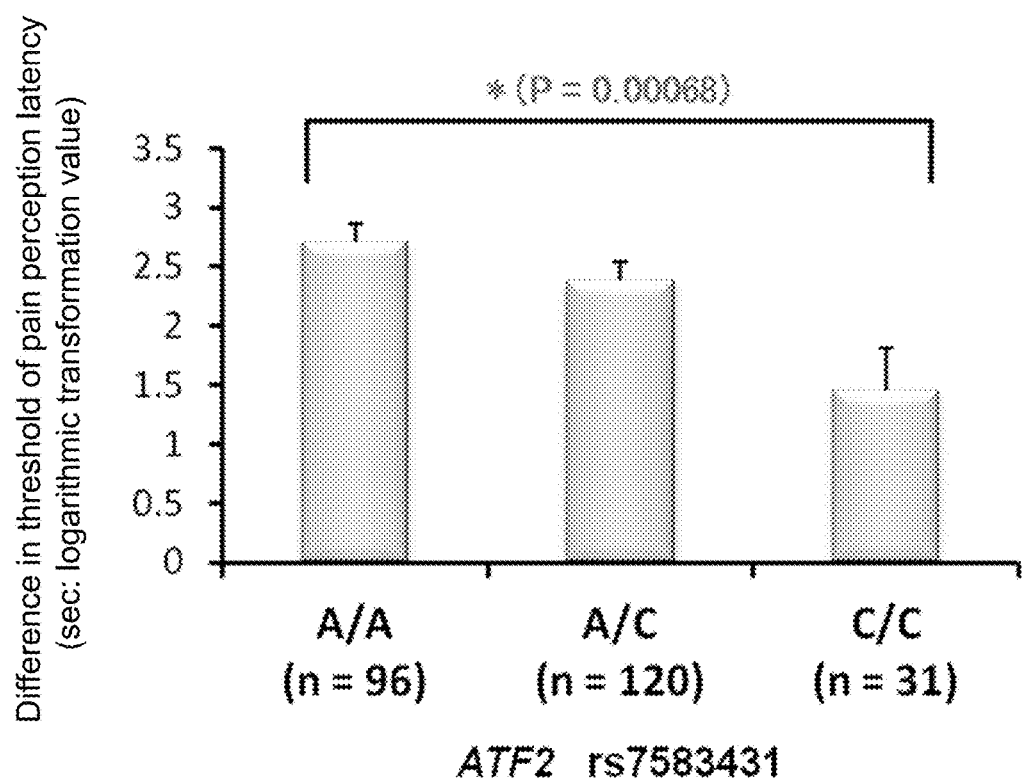
FIG. 12 is a graph showing the effect (overall average±standard deviation) of a polymorphism (rs7583431) of an ATF2 subtype gene on the measurement results (sec) of a difference in threshold of pain perception latency before surgery, in all patients who were administered with analgesic in the surgery (orthognathic surgery).

As a result, as shown in the following Table 24 and FIG. 12, in correlation with the measurement result (logarithmic transformation) of a difference in threshold of pain perception latency due to finger immersion in ice water before the surgery, patients who had a minor allele (C) of the ATF2 subtype gene polymorphism (rs7583431) and underwent the surgery had a difference in threshold of pain perception latency (logarithmic transformation) due to finger immersion in ice water before the surgery that was statistically significantly low in correlation with the number of alleles which they had. Accordingly, by analyzing the ATF2 subtype gene polymorphism (rs7583431), the sensitivity to analgesic before surgery can be more easily predicted.

Using the median (13 sec) of the measurement results of a difference in threshold of pain perception due to finger immersion in ice water before the surgery as a reference, a patient group with a value smaller than the reference and a patient group with a value larger than the reference were defined as a "low analgesic sensitivity group" and a "high analgesic sensitivity group," respectively, and the groups were then stratified in terms of the rs7583431 polymorphism of the ATF2 gene. As a result, in terms of this polymorphism, 40% and 60% of patients were determined to belong to the low analgesic sensitivity group and the high analgesic sensitivity group, respectively, in the A/A patient group. In contrast, in the C/C patient group, 71% and 29% of patients were determined to belong to the low analgesic sensitivity group and the high analgesic sensitivity group, respectively.

TABLE 24

Effect of ATF2 rs7583431 polymorphism on measurement results of difference in threshold of pain sensitivity before surgery in patients treated with analgesic in surgery (orthognathic surgery) (descriptive statistics by gender)

| ATF2 rs7583431 | Gender | Average X̄ | Standard deviation | Number of test subjects (subjects) |
|---|---|---|---|---|
| A/A | F | 26.69 | 32.69 | 64 |
|  | M | 34.78 | 36.28 | 32 |
|  | Total | 29.39 | 33.96 | 96 |
| A/C | F | 26.91 | 36.11 | 76 |
|  | M | 28.73 | 42.97 | 44 |
|  | Total | 27.62 | 38.60 | 120 |
| C/C | F | 14.24 | 25.36 | 25 |
|  | M | 12.00 | 19.07 | 6 |
|  | Total | 13.81 | 24.00 | 31 |

TABLE 24-continued

Effect of ATF2 rs7583431 polymorphism on measurement results of difference in threshold of pain sensitivity before surgery in patients treated with analgesic in surgery (orthognathic surgery) (descriptive statistics by gender)

| ATF2 rs7583431 | Gender | Average X̄ | Standard deviation | Number of test subjects (subjects) |
|---|---|---|---|---|
| Total | F | 24.93 | 33.49 | 165 |
|  | M | 29.87 | 39.24 | 82 |
|  | Total | 26.57 | 35.50 | 247 |

X̄:Measurement (sec) of difference in threshold of pain perception latency due to finger immersion in ice water before surgery Example 6

<Correlation Between Each of CREB1, CREB3, CREB5 and ATF2 Subtype Gene Polymorphisms, and Each of Required Administration Amount of Analgesic, Pain Sensitivity, and Analgesic Effect of Fentanyl>

In the same manner as Examples 2 to 5 above, a correlation between each gene polymorphism of the cyclic AMP responsive element binding protein gene, and each of the required administration amount of analgesic, pain sensitivity, and the analgesic effect of fentanyl was examined. Genomic DNA was extracted from the blood of 355 patients undergoing surgery (orthognathic surgery), and gene polymorphisms in the CREB1, CREB3, CREB5 and ATF2 subtype genes (Tag SNPs in linkage disequilibrium blocks and individual SNPs outside of the linkage disequilibrium blocks) were determined. Then, a correlation between these results of determination of the gene polymorphisms, and each of the required administration amount of analgesic in 24 hours after the surgery, pain sensitivity before the surgery, pain sensitivity (VAS) 24 hours after the surgery and before the surgery, and the analgesic effect of fentanyl, was analyzed.

Incidentally, as the analgesic, fentanyl, which is mainly administered intravenously through a PCA (patient-controlled analgesia) pump, was used.

As a result, the gene polymorphisms of the CREB1, CREB3, CREB5 and ATF2 subtype genes showed a statistically significant correlation with any phenotype of the required administration amount of analgesic in 24 hours after the surgery, pain sensitivity before the surgery, pain sensitivity (VAS) 24 hours after the surgery and before the surgery, and the analgesic effect of fentanyl. Accordingly, by analyzing these gene polymorphisms, the sensitivity to analgesic, pain sensitivity, and the analgesic effect of fentanyl can be predicted.

The results of the present example, as well as the results of Examples 2 to 5, are collectively shown in the following Table 25.

TABLE 25

Tag SNPs in linkage disequilibrium (LD) blocks and SNPs outside of LD blocks found to have significant association with phenotypes

| Gene region | Chromosome No. | LD block No. | Tag SNP | Position | Minor allele frequency | Phenotype | N | Statistics | | | |
|---|---|---|---|---|---|---|---|---|---|---|---|
|  |  |  |  |  |  |  |  | BETA | SE | $R^2$ | P |
| CREB1 | 2 | 1 | rs16839837 | 208079256 | 0.232 | Required amount of fentanyl administered in 24 hours after surgery | 247 | −0.1347 | 0.06718 | 0.01613 | 0.04613 |

TABLE 25-continued

Tag SNPs in linkage disequilibrium (LD) blocks and SNPs outside of LD blocks found to have significant association with phenotypes

| Gene region | Chromosome No. | LD block No. | Tag SNP | Position | Minor allele frequency | Phenotype | N | Statistics | | | |
|---|---|---|---|---|---|---|---|---|---|---|---|
| | | | | | | | | BETA | SE | $R^2$ | P |
| CREB1 | 2 | 1 | rs2360969 | 208081241 | 0.126 | Required amount of fentanyl administered in 24 hours after surgery | 353 | 0.1453 | 0.07182 | 0.01153 | 0.04377 |
| CREB1 | 2 | 1 | rs10932200 | 208095930 | 0.315 | Required amount of fentanyl administered in 24 hours after surgery | 247 | 0.2211 | 0.0597 | 0.05301 | 0.000263 |
| CREB1 | 2 | 1 | rs10932200 | 208095930 | 0.315 | VAS 24 hours after surgery | 247 | 0.3084 | 0.1305 | 0.02228 | 0.01891 |
| CREB1 | 2 | 1 | rs10932200 | 208095930 | 0.315 | pain perception latency before surgery | 247 | −0.14 | 0.06043 | 0.02145 | 0.02129 |
| CREB1 | 2 | 1 | rs4234080 | 208197346 | 0.193 | Required amount of fentanyl administered in 24 hours after surgery | 247 | −0.2078 | 0.07133 | 0.03348 | 0.003906 |
| CREB3 | 9 | 1 | rs2145925 | 35679373 | 0.39 | Required amount of fentanyl administered in 24 hours after surgery | 246 | −0.1258 | 0.05884 | 0.01838 | 0.03358 |
| CREB3 | 9 | 1 | rs2025126 | 35686625 | 0.366 | Required amount of fentanyl administered in 24 hours after surgery | 247 | −0.1281 | 0.06011 | 0.01821 | 0.03402 |
| CREB3 | 9 | 2 | rs4878628 | 35756561 | 0.134 | VAS 24 hours after surgery | 253 | −0.4888 | 0.1739 | 0.0305 | 0.005343 |
| CREB5 | 7 | 1 | rs4722778 | 28278588 | 0.256 | Required amount of fentanyl administered in 24 hours after surgery | 126 | −0.2062 | 0.09913 | 0.03371 | 0.03961 |
| CREB5 | 7 | — | rs2175738 | 28304605 | 0.161 | Required amount of fentanyl administered in 24 hours after surgery | 126 | −0.3309 | 0.1141 | 0.06356 | 0.0044 |
| CREB5 | 7 | — | rs2175738 | 28304605 | 0.161 | VAS 24 hours after surgery | 126 | −0.5459 | 0.2322 | 0.04267 | 0.0203 |
| CREB5 | 7 | — | rs17156579 | 28327642 | 0.055 | Required amount of fentanyl administered in 24 hours after surgery | 253 | −0.306 | 0.1293 | 0.02184 | 0.01868 |
| CREB5 | 7 | — | rs17156603 | 28348671 | 0.398 | pain perception latency before surgery | 253 | −0.1105 | 0.05533 | 0.01564 | 0.04692 |
| CREB5 | 7 | — | rs17642145 | 28355789 | 0.008 | pain perception latency before surgery | 247 | −0.7505 | 0.319 | 0.02209 | 0.01943 |
| CREB5 | 7 | 5 | rs4722785 | 28356666 | 0.488 | Required amount of fentanyl administered in 24 hours after surgery | 253 | −0.1142 | 0.05564 | 0.01651 | 0.04114 |
| CREB5 | 7 | 6 | rs16874525 | 28357707 | 0.461 | VAS 24 hours after surgery | 252 | 0.2455 | 0.121 | 0.01621 | 0.04345 |
| CREB5 | 7 | 10 | rs17156649 | 28386945 | 0.079 | Analgesic effect of fentanyl before surgery | 247 | −0.6983 | 0.2917 | 0.02285 | 0.01743 |
| CREB5 | 7 | — | rs7794304 | 28394916 | 0.457 | pain perception latency before surgery | 354 | −0.1154 | 0.05005 | 0.01487 | 0.02175 |
| CREB5 | 7 | 12 | rs1029897 | 28400928 | 0.409 | pain perception latency before surgery | 353 | −0.09985 | 0.04979 | 0.01133 | 0.04568 |
| CREB5 | 7 | — | rs4722793 | 28404054 | 0.405 | pain perception latency before surgery | 252 | −0.1225 | 0.05698 | 0.01817 | 0.03246 |
| CREB5 | 7 | 13 | rs10233653 | 28406845 | 0.421 | pain perception latency before surgery | 354 | −0.119 | 0.05004 | 0.0158 | 0.01796 |
| CREB5 | 7 | 13 | rs6955105 | 28409814 | 0.465 | pain perception latency before surgery | 354 | −0.1222 | 0.0481 | 0.01802 | 0.01147 |

TABLE 25-continued

Tag SNPs in linkage disequilibrium (LD) blocks and SNPs outside of LD blocks found to have significant association with phenotypes

| Gene region | Chromosome No. | LD block No. | Tag SNP | Position | Minor allele frequency | Phenotype | N | BETA | SE | $R^2$ | P |
|---|---|---|---|---|---|---|---|---|---|---|---|
| CREB5 | 7 | — | rs17156685 | 28431959 | 0.087 | pain perception latency before surgery | 247 | −0.2359 | 0.1053 | 0.02007 | 0.02598 |
| CREB5 | 7 | — | rs17156694 | 28451480 | 0.441 | pain perception latency before surgery | 253 | −0.1379 | 0.05492 | 0.02449 | 0.0127 |
| CREB5 | 7 | 15 | rs177572 | 28460820 | 0.331 | pain perception latency before surgery | 253 | 0.1454 | 0.06446 | 0.01988 | 0.02492 |
| CREB5 | 7 | — | rs177574 | 28461566 | 0.047 | Analgesic effect of fentanyl before surgery | 247 | 0.7803 | 0.3685 | 0.01798 | 0.03521 |
| CREB5 | 7 | — | rs177576 | 28463632 | 0.327 | Analgesic effect of fentanyl before surgery | 247 | 0.4179 | 0.1582 | 0.02771 | 0.008764 |
| CREB5 | 7 | — | rs13437706 | 28465016 | 0.374 | Analgesic effect of fentanyl before surgery | 253 | 0.3854 | 0.1501 | 0.02559 | 0.01083 |
| CREB5 | 7 | 16 | rs177580 | 28465195 | 0.382 | Analgesic effect of fentanyl before surgery | 253 | −0.3177 | 0.1503 | 0.01749 | 0.03554 |
| CREB5 | 7 | 16 | rs12666636 | 28465748 | 0.224 | VAS 24 hours after surgery | 354 | −0.2569 | 0.1182 | 0.01325 | 0.03036 |
| CREB5 | 7 | — | rs216715 | 28539407 | 0.287 | VAS 24 hours after surgery | 354 | −0.2213 | 0.1069 | 0.01202 | 0.03923 |
| CREB5 | 7 | — | rs10951197 | 28540048 | 0.39 | VAS 24 hours after surgery | 253 | −0.248 | 0.1181 | 0.01726 | 0.03676 |
| CREB5 | 7 | — | rs160335 | 28554342 | 0.496 | VAS 24 hours after surgery | 247 | 0.2437 | 0.122 | 0.01602 | 0.04693 |
| CREB5 | 7 | 25 | rs310353 | 28603649 | 0.299 | VAS 24 hours after surgery | 247 | −0.2846 | 0.1258 | 0.02047 | 0.02451 |
| CREB5 | 7 | — | rs310359 | 28606311 | 0.217 | Required amount of fentanyl administered in 24 hours after surgery | 126 | 0.2233 | 0.1071 | 0.0339 | 0.03904 |
| CREB5 | 7 | 26 | rs1637457 | 28615963 | 0.22 | pain perception latency before surgery | 253 | −0.1327 | 0.06564 | 0.01603 | 0.04422 |
| CREB5 | 7 | — | rs41348 | 28683373 | 0.386 | pain perception latency before surgery | 354 | −0.1254 | 0.04985 | 0.01765 | 0.01235 |
| CREB5 | 7 | — | rs886816 | 28689932 | 0.181 | Required amount of fentanyl administered in 24 hours after surgery | 354 | 0.1596 | 0.06074 | 0.01924 | 0.008961 |
| CREB5 | 7 | 32 | rs17157048 | 28703823 | 0.087 | Required amount of fentanyl administered in 24 hours after surgery | 354 | −0.2175 | 0.09867 | 0.01361 | 0.02816 |
| CREB5 | 7 | 32 | rs10951201 | 28711867 | 0.154 | Required amount of fentanyl administered in 24 hours after surgery | 354 | −0.2078 | 0.07776 | 0.01988 | 0.007896 |
| CREB5 | 7 | 32 | rs10265166 | 28713821 | 0.043 | Analgesic effect of fentanyl before surgery | 253 | 0.9373 | 0.4605 | 0.01624 | 0.04285 |
| CREB5 | 7 | 32 | rs6972081 | 28715571 | 0.287 | pain perception latency before surgery | 354 | −0.1289 | 0.05762 | 0.01402 | 0.02588 |
| CREB5 | 7 | 33 | rs6462100 | 28720620 | 0.134 | Required amount of fentanyl administered in 24 hours after surgery | 354 | −0.2022 | 0.08 | 0.01782 | 0.01194 |
| CREB5 | 7 | — | rs2066979 | 28730634 | 0.276 | pain perception latency before surgery | 250 | −0.1395 | 0.06557 | 0.01792 | 0.0344 |

TABLE 25-continued

Tag SNPs in linkage disequilibrium (LD) blocks and SNPs outside of LD blocks found to have significant association with phenotypes

| Gene region | Chromosome No. | LD block No. | Tag SNP | Position | Minor allele frequency | Phenotype | N | Statistics | | | |
|---|---|---|---|---|---|---|---|---|---|---|---|
| | | | | | | | | BETA | SE | $R^2$ | P |
| CREB5 | 7 | — | rs10486591 | 28733403 | 0.272 | pain perception latency before surgery | 354 | −0.1231 | 0.05973 | 0.01192 | 0.04007 |
| CREB5 | 7 | 35 | rs721993 | 28745985 | 0.154 | Required amount of fentanyl administered in 24 hours after surgery | 354 | −0.1698 | 0.07741 | 0.01348 | 0.02898 |
| CREB5 | 7 | 40 | rs3735566 | 28831314 | 0.039 | Required amount of fentanyl administered in 24 hours after surgery | 247 | −0.2901 | 0.1445 | 0.01618 | 0.04582 |
| ATF2 | 2 | 1 | rs1153702 | 175629003 | 0.476 | Analgesic effect of fentanyl before surgery | 354 | 0.2496 | 0.1214 | 0.01188 | 0.04044 |
| ATF2 | 2 | 1 | rs7583431 | 175630628 | 0.366 | Analgesic effect of fentanyl before surgery | 247 | −0.5442 | 0.1582 | 0.04606 | 0.000685 |
| ATF2 | 2 | — | rs1153699 | 175631032 | 0.472 | Analgesic effect of fentanyl before surgery | 247 | 0.3865 | 0.1524 | 0.02558 | 0.01184 |
| ATF2 | 2 | — | rs1153699 | 175631032 | 0.472 | pain perception latency before surgery | 247 | 0.1173 | 0.0577 | 0.01659 | 0.04312 |
| ATF2 | 2 | 2 | rs268214 | 175741461 | 0.189 | Analgesic effect of fentanyl before surgery | 247 | 0.4065 | 0.1863 | 0.01907 | 0.03004 |

Example 7

<Correlation Between CREB1 Subtype Gene Polymorphism (Rs2952768) and Required Administration Amount of Analgesic>

A correlation between a cyclic AMP responsive element binding protein gene polymorphism and the required administration amount of analgesic was examined. Genomic DNA was extracted from the blood of 354 patients undergoing surgery (orthognathic surgery), and one gene polymorphism (rs2952768) in the CREB1 subtype gene was determined. Then, a correlation between these results of determination of the gene polymorphism and the required administration amount of analgesic after the surgery was analyzed.

Incidentally, as the analgesic, fentanyl, which is mainly administered intravenously through a PCA (patient-controlled analgesia) pump, was used.

Figure 13:
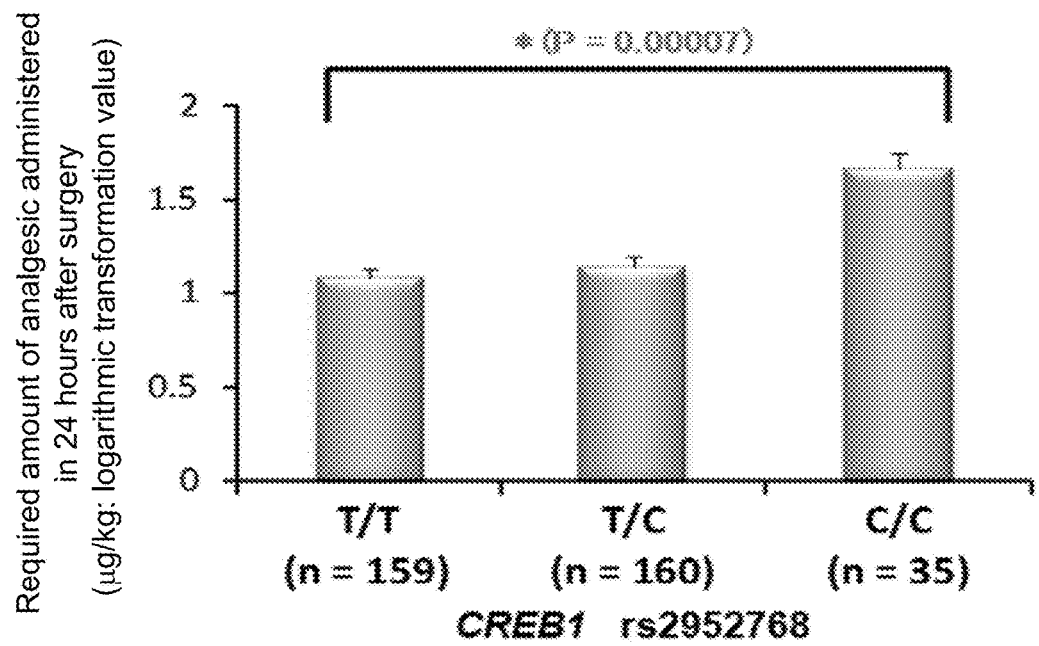
FIG. 13 is a graph showing the effect (overall average±standard deviation) of a polymorphism (rs2952768) of a CREB1 subtype gene on the required administration amount (μg/kg) of analgesic in 24 hours after surgery, in all patients who were administered with analgesic in the surgery (orthognathic surgery).

As a result, as shown in the following Table 26 and FIG. 13, in the case of patients who had a minor allele (C) of the CREB1 subtype gene polymorphism (rs2952768) and underwent the surgery, the required administration amount (logarithmic transformation) of analgesic after the surgery was statistically significantly high in correlation with the number of alleles which they had. Accordingly, by analyzing the CREB1 subtype gene polymorphism (rs2952768), the sensitivity to analgesic can be predicted.

Using the median (2.268 (μg/kg)) of the required administration amount of fentanyl in 24 hours after the surgery as a reference, a patient group with a value smaller than the reference and a patient group with a value larger than the reference were defined as a "high analgesic sensitivity group" and a "low analgesic sensitivity group," respectively, and the groups were then stratified in terms of the rs2952768 polymorphism of the CREB1 gene. As a result, in terms of this polymorphism, 53% and 47% of patients were determined to belong to the high analgesic sensitivity group and the low analgesic sensitivity group, respectively, in the T/T or T/C patient group. In contrast, in the C/C patient group, 22% and 78% of patients were determined to belong to the high analgesic sensitivity group and the low analgesic sensitivity group, respectively.

TABLE 26

Effect of CREB1 rs2952768 polymorphism on required amount of analgesic administered in 24 hours after surgery in patients treated with analgesic in surgery (orthognathic surgery)(descriptive statistics by gender)

| CREB1 rs2952768 | Gender | Average X̄ | Standard deviation | Number of test subjects (subjects) |
|---|---|---|---|---|
| T/T | F | 2.78 | 2.43 | 101 |
| | M | 2.38 | 2.46 | 58 |
| | Total | 2.64 | 2.44 | 159 |
| T/C | F | 2.99 | 2.42 | 108 |
| | M | 2.38 | 2.50 | 52 |
| | Total | 2.79 | 2.46 | 160 |
| C/C | F | 4.80 | 3.05 | 20 |
| | M | 5.08 | 2.55 | 15 |
| | Total | 4.92 | 2.81 | 35 |
| Total | F | 3.05 | 2.53 | 229 |
| | M | 2.71 | 2.62 | 125 |
| | Total | 2.93 | 2.57 | 354 |

X̄:Required amount (μg/kg) of analgesic administered in 24 hours after surgery

Example 8

<Correlation Between CREB1 Subtype Gene Polymorphism (Rs2952768) and Required Administration Amount of Analgesic>

A correlation between a cyclic AMP responsive element binding protein gene polymorphism and the required administration amount of analgesic was examined. Genomic DNA was extracted from the blood or the oral mucosa of 112 patients undergoing surgery (abdominal surgery), and one gene polymorphism (rs2952768) in the CREB1 subtype gene was determined. Then, a correlation between these results of determination of the gene polymorphism and the required administration amount of analgesic after the surgery was analyzed.

Incidentally, as the analgesic, analgesics such as pentazocine and pethidine, which are mainly administered intravenously, buprenorphine, diclofenac and indomethacin, which are mainly administered as a suppository, flurbiprofen axetil, which is injected by intravenous infusion, as well as epidural morphine and marcain were used.

Incidentally, the total amount of each analgesic in terms of fentanyl means the total amount of analgesic (mg) in the case where the amount of each administered analgesic is converted to a value corresponding to the potency equivalent to fentanyl. The conversion of the amount of each analgesic to a value corresponding to the potency of fentanyl was carried out by setting a potency equivalent to 0.3 mg of fentanyl at 90 mg of pentazocine, 360 mg in the case of pethidine (Opystan), 1 mg in the case of buprenorphine (Lepetan), 300 mg in the case of diclofenac (Voltaren), 300 mg in the case of flurbiprofen axetil (Ropion), and 6 mg in the case of epidural morphine.

Figure 14:
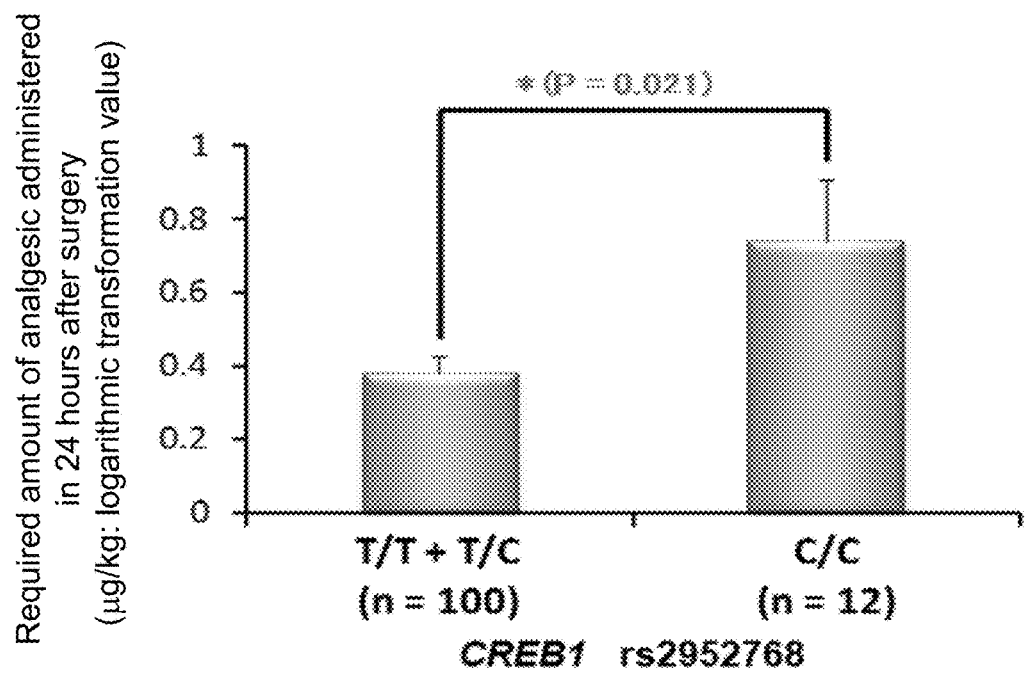
FIG. 14 is a graph showing the effect (overall average±standard deviation) of a polymorphism (rs2952768) of a CREB1 subtype gene on the required administration amount (μg/kg) of analgesic in 24 hours after surgery, in all patients who were administered with analgesic in the surgery (abdominal surgery).

As a result, as shown in the following Table 27 and FIG. 14, in the case of patients who did not have a major allele (T) of the CREB1 subtype gene polymorphism (rs2952768) and underwent the surgery, the required administration amount (logarithmic transformation) of analgesic after the surgery was statistically significantly higher compared with patients having the aforementioned allele (T). Accordingly, by analyzing the CREB1 subtype gene polymorphism (rs2952768), the sensitivity to each analgesic can be predicted.

Using the median (2.453 (μg/kg)) of the required total administration amount of each analgesic in terms of fentanyl in 24 hours after the surgery as a reference, a patient group with a value smaller than the reference and a patient group with a value larger than the reference were defined as a "high analgesic sensitivity group" and a "low analgesic sensitivity group," respectively, and the groups were then stratified in terms of the rs2952768 polymorphism of the CREB1 gene. As a result, in terms of this polymorphism, 52% and 48% of patients were determined to belong to the high analgesic sensitivity group and the low analgesic sensitivity group, respectively, in the T/T or T/C patient group. In contrast, in the C/C patient group, 33% and 67% of patients were determined to belong to the high analgesic sensitivity group and the low analgesic sensitivity group, respectively.

TABLE 27

Effect of CREB1 rs2952768 polymorphism on required amount of analgesic administered in 24 hours after surgery in patients treated with analgesic in surgery (abdominal surgery) (descriptive statistics by gender)

| CREB1 rs2952768 | Gender | Average ✕ | Standard deviation | Number of test subjects (subjects) |
|---|---|---|---|---|
| T/T | F | 0.93 | 1.35 | 18 |
|  | M | 0.43 | 0.63 | 26 |
|  | total | 0.63 | 1.01 | 44 |
| T/C | F | 0.67 | 1.32 | 28 |
|  | M | 0.78 | 1.01 | 28 |
|  | Total | 0.72 | 1.17 | 56 |
| C/C | F | 1.12 | 1.34 | 6 |
|  | M | 1.78 | 1.61 | 6 |
|  | Total | 1.45 | 1.45 | 12 |
| Total | F | 0.81 | 1.32 | 52 |
|  | M | 0.73 | 1.00 | 60 |
|  | Total | 0.77 | 1.15 | 112 |

✕Required total amount (μg/kg) of analgesic administered in terms of fentanyl in 24 hours after surgery

Example 9

<Correlation Between CREB1 Subtype Gene Polymorphism (Rs2952768) and Severity of Drug Dependence in Methamphetamine-Dependent Patients>

A correlation between a cyclic AMP responsive element binding protein gene polymorphism and vulnerability to drug dependence associated with the severity of drug dependence was examined. Genomic DNA was extracted from the blood of 194 methamphetamine-dependent patients, and one gene polymorphism (rs2952768) in the CREB1 subtype gene was determined. The patients were classified based on the presence or absence of the abuse of many drugs, and a comparison was made among them. The results are shown in the following Table 28. Here, the methamphetamine-dependent patients were classified into two groups, namely, a patient group involving the abuse of drugs other than stimulants (two or more types) and a patient group involving the abuse of a single drug (only one type).

As a result, as is clear from the following Table 28, a significant difference in genotype frequency was observed in terms of the gene polymorphism (rs2952768), and in methamphetamine-dependent patients having a major allele (T), the number of patients who abused many drugs was statistically significantly higher compared with patient who did not have the aforementioned allele T.

From the above results, it was demonstrated that drug sensitivity associated with the severity of stimulant dependence can be easily predicted by determining genotype frequency in the cyclic AMP responsive element binding protein gene polymorphism.

TABLE 28

Comparison of genotype and allele frequencies in rs2952768 polymorphism in methamphetamine-dependent patients classified based on presence or absence of abuse of many drugs
Gene polymorphism name: CREB1 rs2952768

| Sample name | (Number of samples) | Genotype frequency (%) | | | | Allele frequency | |  |
|---|---|---|---|---|---|---|---|---|
| | | T/T | T/C | C/C | | T | C | |
| Metham- phetamine dependent patients | Abuse of many drugs No (53) Yes (141) | 19 (35.8%) 58 (41.1%) | 22 (41.5%) 67 (47.5%) | 12 (22.6%) 16 (11.3%) | (P = 0.137: genotype) (P = 0.603: dominant model) *(P = 0.046: recessive model) | 0.556 0.644 | 0.444 0.356 | (P = 0.133: allele) |

※Each model indicates hereditary mode regarding minor allele (C): *, P < 0.05.

Example 10

<Correlation Between CREB1 Subtype Gene Polymorphism (Rs2952768) and Severity of Drug Dependence in Alcohol-Dependent Patients>

A correlation between a cyclic AMP responsive element binding protein gene polymorphism and vulnerability to drug dependence associated with the severity of drug dependence was examined. Genomic DNA was extracted from the blood of 436 alcohol-dependent patients, and one gene polymorphism (rs2952768) in the CREB1 subtype gene was determined. The patients were classified based on the presence or absence of drug abuse, and a comparison was made among them. The results are shown in the following Table 29. Here, the alcohol-dependent patients were classified into two groups, namely, a patient group with drug abuse (one or more types) and a patient group without drug abuse (only alcohol ingestion).

As a result, as is clear from the following Table 29, a significant difference in genotype and allele frequencies was observed in terms of the gene polymorphism (rs2952768), and it was demonstrated that the frequency of major allele (T) was statistically significantly higher in the patient group with drug abuse than in the patient group without drug abuse.

From the above results, it was demonstrated that vulnerability to drug dependence associated with the severity of drug dependence can be easily predicted by determining genotype and allele frequencies in the cyclic AMP responsive element binding protein gene polymorphism.

Example 11

<Correlation Between CREB1 Subtype Gene Polymorphism (Rs2952768) and Severity of Drug Dependence in Eating Disorder Patients>

A correlation between a cyclic AMP responsive element binding protein gene polymorphism and vulnerability to drug dependence associated with the severity of drug dependence was examined. Genomic DNA was extracted from the blood of 221 patients with eating disorder, and one gene polymorphism (rs2952768) in the CREB1 subtype gene was determined. The patients were classified based on the presence or absence of drug dependence, and a comparison was made among them. The results are shown in the following Table 30. Here, the eating disorder patients were classified into two groups, namely, a patient group with a complication of drug dependence and a patient group without a complication of drug dependence.

As a result, as is clear from the following Table 30, a significant difference in genotype and allele frequencies was observed in terms of the gene polymorphism (rs2952768), and it was demonstrated that the frequency of major allele (T) was statistically significantly higher in the patient group with a complication of drug dependence than in the patient group without a complication of drug dependence.

From the above results, it was demonstrated that vulnerability to drug dependence associated with the severity of drug dependence can be easily predicted by determining genotype and allele frequencies in the cyclic AMP responsive element binding protein gene polymorphism.

TABLE 29

Comparison of genotype and allele frequencies in rs2952768 polymorphism in alcohol-dependent patients classified based on presence or abscence of drug abuse
Gene polymorphism name: CREB1 rs2952768

| Sample name | (Number of samples) | Genotype frequency (%) | | | | Allele frequency | | |
|---|---|---|---|---|---|---|---|---|
| | | T/T | T/C | C/C | | T | C | |
| Alcohol- dependent patients | Drug abuse No (391) Yes (45) | 172 (44.0%) 25 (55.6%) | 166 (42.5%) 18 (40.0%) | 53 (13.6%) 2 (4.4%) | (P = 0.142: genotype) (P = 0.140: dominant model) †(P = 0.097: recessive model) | 0.652 0.756 | 0.348 0.244 | * (P = 0.049: allele) |

※Each model indicates hereditary mode regarding minor allele (C): *, P < 0.05 †, 0.05 ≤ P < 0.1.

TABLE 30

Comparison of genotype and allele frequencies in rs2952768 polymorphism in
patients with eating disorder classified based on presence or absence of complication of drug dependence
Gene polymorphism name: CREB1 rs2952768

| Sample name | (Number of samples) | Genotype frequency (%) | | | | Allele frequency | | |
|---|---|---|---|---|---|---|---|---|
| | | T/T | T/C | C/C | | T | C | |
| Eating disorder patients | Complication of drug (200) No (21) Yes | 85 (42.5%) 14 (66.7%) | 93 (46.5%) 6 (28.6%) | 22 (11.0%) 1 (4.9%) | (P = 0.103: genotype) *(P = 0.034: dominant model) (P = 0.705: recessive model) | 0.658 0.610 | 0.343 0.190 | * (P = 0.046: allele) |

※Each model indicates hereditary mode regarding minor allele (C): *, P < 0.05.

Example 12

<Correlation Between CREB1 Subtype Gene Polymorphism (Rs2952768) and Severity of Substance Dependence in Eating Disorder Patients>

A correlation between a cyclic AMP responsive element binding protein gene polymorphism and vulnerability to substance (alcohol) dependence associated with the severity of substance (alcohol) dependence was examined. Genomic DNA was extracted from the blood of 221 patients with eating disorder, and one gene polymorphism (rs2952768) in the CREB1 subtype gene was determined. The patients were classified based on the presence or absence of alcohol dependence, and a comparison was made among them. The results are shown in the following Table 31. Here, the eating disorder patients were classified into two groups, namely, a patient group with a complication of alcohol dependence and a patient group without a complication of alcohol dependence.

As a result, as is clear from the following Table 31, a significant difference in genotype and allele frequencies was observed in terms of the gene polymorphism (rs2952768), and it was demonstrated that the frequency of major allele (T) was statistically significantly higher in the patient group with a complication of alcohol dependence than in the patient group without a complication of alcohol dependence.

From the above results, it was demonstrated that vulnerability to substance (alcohol) dependence associated with the severity of substance (alcohol) dependence can be easily predicted by determining genotype and allele frequencies in the cyclic AMP responsive element binding protein gene polymorphism.

Example 13

<Correlation Between CREB1 Subtype Gene Polymorphism (Rs2952768) and Reward Dependence>

A correlation between a cyclic AMP responsive element binding protein gene polymorphism and dependence-prone personality associated with reward dependence was examined. Genomic DNA was extracted from the oral mucosa of 495 healthy subjects, and one gene polymorphism (rs2952768) in the CREB1 subtype gene was determined. Then, a correlation between these results of determination of the gene polymorphism and dependence-prone personality was analyzed.

It is to be noted that, as a test of dependence-prone personality, a reward dependence (RD) score (average) in the Temperament and Character Inventory (TCI) was used.

Figure 15:
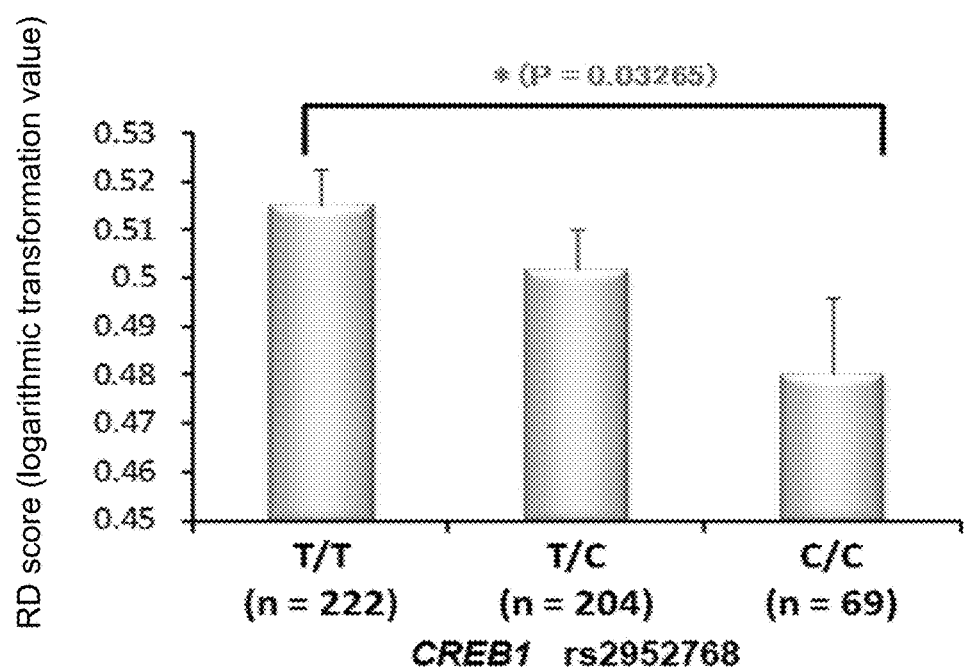
FIG. 15 is a graph showing the effect (overall average±standard deviation) of a polymorphism (rs2952768) of a CREB1 subtype gene on the reward dependence (RD) score (average) of Temperament and Character Inventory (TCI) in all healthy subjects.

As a result, as is shown in the following Table 32 and FIG. 15, healthy subjects having a minor allele (C) in the CREB1 subtype gene polymorphism (rs2952768) had an RD score (logarithmic transformation) that was statistically significantly low in correlation with the number of alleles which they had. Accordingly, by analyzing the CREB1 subtype gene polymorphism (rs2952768), dependence-prone personality can be predicted.

Using the median (0.667) of the RD score as a reference, a patient group with a value smaller than the reference and a patient group with a value larger than the reference were defined as a "low reward dependence group" and a "high reward dependence group," respectively, and the groups were then stratified in terms of the rs2952768 polymorphism of the CREB1 gene. As a result, in terms of this polymorphism, 43% and 57% of healthy subjects were determined to

TABLE 31

Comparison of genotype and allele frequencies in rs2952768 polymorphism in patients with
eating disorder classified based on presence or abscence of complication of alcohol dependence
Gene polymorphism name: CREB1 rs2952768

| Sample name | (Number of samples) | Genotype frequency (%) | | | | Allele frequency | | |
|---|---|---|---|---|---|---|---|---|
| | | T/T | T/C | C/C | | T | C | |
| Eating disorder patients | Complication of alcohol (151) No (70) Yes | 61 (40.4%) 38 (54.3%) | 72 (47.7%) 27 (38.6%) | 18 (11.9%) 5 (7.1%) | (P = 0.136: genotype) †(P = 0.053: dominant model) (P = 0.279: recessive model) | 0.642 0.738 | 0.358 0.264 | † (P = 0.052: allele) |

※Each model indicates hereditary mode regarding minor allele (C): †, 0.05 ≤ P < 0.1.

belong to the low reward dependence group and the high reward dependence group, respectively, in the T/T patient group. In contrast, in the C/C patient group, 58% and 42% of healthy subjects were determined to belong to the low reward dependence group and the high reward dependence group, respectively.

From the above results, it was demonstrated that dependence-prone personality associated with reward dependence can be easily predicted by determining genotype and allele frequencies in the cyclic AMP responsive element binding protein gene polymorphism.

TABLE 32

Effect of CREB1 rs2952768 polymorphism on reward dependence (RD) score (average) (descriptive statistics by gender)

| CREB1 rs2952768 | Gender | Average X̄ | Standard deviation | Number of test subjects (subjects) |
|---|---|---|---|---|
| T/T | F | 0.72 | 0.18 | 98 |
| | M | 0.66 | 0.18 | 122 |
| | Unknown | 0.60 | 0.09 | 2 |
| | Total | 0.68 | 0.18 | 222 |
| T/C | F | 0.70 | 0.18 | 103 |
| | M | 0.62 | 0.20 | 98 |
| | Unknown | 0.78 | 0.08 | 3 |
| | Total | 0.66 | 0.19 | 204 |
| C/C | F | 0.68 | 0.22 | 37 |
| | M | 0.58 | 0.18 | 32 |
| | Total | 0.63 | 0.21 | 69 |
| 総和 | F | 0.70 | 0.19 | 238 |
| | M | 0.63 | 0.19 | 252 |
| | Unknown | 0.71 | 0.12 | 5 |
| | Total | 0.67 | 0.19 | 495 |

X̄:Average in dimension of average score in each subscale

Example 14

<Correlation Between CREB1 Subtype Gene Polymorphism (Rs2952768) and Expression Level of CREB1 Gene>

A correlation between a cyclic AMP responsive element binding protein gene polymorphism and a gene expression level was examined. Genomic DNA was extracted from the blood of 100 postmortem brain tissue donors at the Stanley Foundation Brain Bank, and one gene polymorphism (rs2952768) in the CREB1 subtype gene was determined. Then, a correlation between these results of determination of the gene polymorphism and a gene expression level was analyzed.

Incidentally, as the gene expression level, the value of the relative mRNA expression level of CREB1, which was standardized with the value of the mRNA expression level of a β-actin gene (ACTB), was used.

Figure 16:
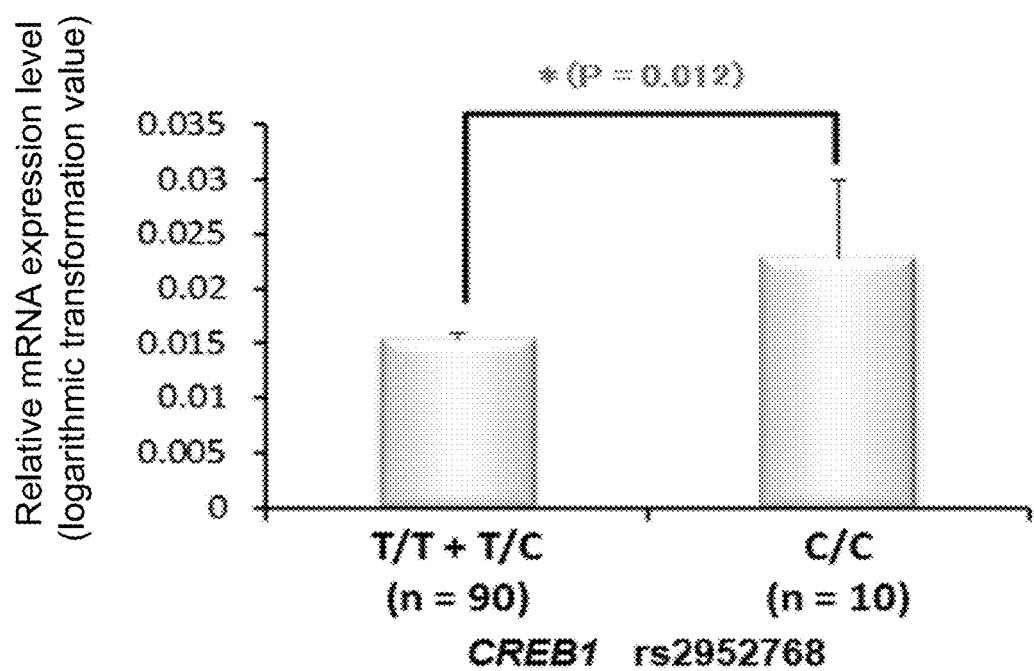
FIG. 16 is a graph showing the effect (overall average±standard deviation) of a polymorphism (rs2952768) of a CREB1 subtype gene on the expression level of a CREB1 subtype gene in postmortem brain tissue donors at the Stanley Foundation Brain Bank.

As a result, as shown in the following Table 33 and FIG. 16, in the case of subjects who did not have a major allele (T) of the CREB1 subtype gene polymorphism (rs2952768), the mRNA expression level (logarithmic transformation) of CREB1 was statistically significantly higher compared with subjects having the aforementioned allele (T). Accordingly, by analyzing the CREB1 subtype gene polymorphism (rs2952768), the gene expression level can be predicted.

Using the median (0.0145) of the relative mRNA expression level as a reference, a subject group with a value smaller than the reference and a subject group with a value larger than the reference were defined as a "low gene expression group" and a "high gene expression group," respectively, and the groups were then stratified in terms of the rs2952768 polymorphism of the CREB1 gene. As a result, in terms of this polymorphism, 52% and 48% of subjects were determined to belong to the low gene expression group and the high gene expression group, respectively, in the T/T or T/C subject group. In contrast, in the C/C subject group, 30% and 70% of subjects were determined to belong to the low gene expression group and the high gene expression group, respectively.

From the above results, it was demonstrated that the tendency of the expression level of a CREB1 gene (whether the gene tends to be expressed at a high level or at a low level) can be easily predicted by determining genotype and allele frequencies in the cyclic AMP responsive element binding protein gene polymorphism.

TABLE 33

Effect of CREB1 rs2952768 polymorphism on gene expression level in postmortem brain tissue donors at Stanley Foundation Brain Bank (descriptive statistics)

| CREB1 rs2952768 | Average X̄ | Standard deviation | Number of test subjects (subjects) |
|---|---|---|---|
| T/T | 0.015345 | 0.006618 | 48 |
| T/C | 0.015667 | 0.005267 | 42 |
| C/C | 0.023360 | 0.023537 | 10 |
| Total | 0.016282 | 0.009396 | 100 |

X̄:Relative mRNA expression level value of CREB1 standardized with mRNA expression level value of β-actin gene (ACTB)

INDUSTRIAL APPLICABILITY

According to the present invention, it becomes possible to provide: a gene polymorphism of a cyclic AMP responsive element binding protein gene or a haplotype constituted by the gene polymorphism, which can evaluate an individual difference in terms of drug sensitivity and disease vulnerability; a method for evaluating drug sensitivity and disease vulnerability using the gene polymorphism or the haplotype; and the like. According to this evaluation method, it becomes possible to readily know or predict a proper prescribed amount, a proper prescribed schedule associated with a narcotic drug such as morphine, and the like, and hence the method is extremely useful for personalized pain therapy, drug dependence therapy and the like.

The invention claimed is:

1. A method for treating a human subject with fentanyl following surgery comprising:
   (a) obtaining from the human subject a nucleic acid sample;
   (b) detecting the nucleic acids in the nucleic acid sample to determine the genotype of the rs2952768 polymorphism;
   (c1) administering to the human subject having a C/C genotype at rs2952768 a higher amount of fentanyl, wherein the higher amount of fentanyl is in comparison to predetermined median reference value, or
   (c2) administering to the human subject having a T/C or T/T genotype at rs2952768 a lower amount of fentanyl, wherein the lower amount of fentanyl is in comparison to predetermined median reference value.

2. The method according to claim 1, wherein the nucleic acid sample is extracted from blood or oral mucosa of the human subject.

3. The method according to claim 1, wherein the surgery is orthognathic surgery, and wherein the predetermined median reference value is 2.268 µg/kg.

4. The method according to claim 1, wherein 4.80 to 5.08 µg/kg of fentanyl is administered to the human subject having a C/C genotype at rs2952768 after orthognathic surgery.

5. The method according to claim 1, wherein 2.38 to 2.78 µg/kg of fentanyl is administered to the human subject having a T/T genotype at rs2952768 after orthognathic surgery.

6. The method according to claim 1, wherein 2.38 to 2.99 µg/kg of fentanyl is administered to the human subject having a T/C genotype at rs2952768 after orthognathic surgery.

7. The method according to claim 1, wherein the surgery is abdominal surgery, and wherein the predetermined median reference value is 2.453 µg/kg.

8. The method according to claim 1, wherein 1.12 to 1.78 µg/kg of fentanyl is administered to the human subject having a C/C genotype at rs2952768 after abdominal surgery.

9. The method according to claim 1, wherein 0.43 to 0.93 µg/kg of fentanyl is administered to the human subject having a T/T genotype at rs2952768 after abdominal surgery.

10. The method according to claim 1, wherein 0.67 to 0.78 µg/kg of fentanyl is administered to the human subject having a T/C genotype at rs2952768 after abdominal surgery.

* * * * *

SEQUENCE LISTING

<160> NUMBER OF SEQ ID NOS: 172

<210> SEQ ID NO 1
<211> LENGTH: 101
<212> TYPE: DNA
<213> ORGANISM: Homo sapiens

```
<400> SEQUENCE: 1
atttaaagaa gaccagcaga aaaatattta tgaacttatt ttcaacttgt ycccattttt      60 gaacttttt atcagtgaag aaatggaaac attttttcaa t                         101

<210> SEQ ID NO 2
<211> LENGTH: 101
<212> TYPE: DNA
<213> ORGANISM: Homo sapiens

<400> SEQUENCE: 2
atgaaaaact ggggatgagg gccagtcatc tgtatttcaa caagtcttgc yggtgattcc     60
gatgcacgcc atagcgtgag aaccagtata gcaataaaac c                        101

<210> SEQ ID NO 3
<211> LENGTH: 101
<212> TYPE: DNA
<213> ORGANISM: Homo sapiens

<400> SEQUENCE: 3
aatagggaga gcaaaagagc aaagaggtgg ttgttcggtg atcaatttcc mccagagtag     60
taaggaaagg cctcacagaa acaggagcat ttgagcaaag a                        101

<210> SEQ ID NO 4
<211> LENGTH: 101
<212> TYPE: DNA
<213> ORGANISM: Homo sapiens

<400> SEQUENCE: 4
acaaataatg agaagtagga attggaaaag aaagtgataa gttacagtta rgtaggagga    60
atgggtgaca gaaaaaaatt ccaggggaag ggaagggcat g                        101

<210> SEQ ID NO 5
<211> LENGTH: 101
<212> TYPE: DNA
<213> ORGANISM: Homo sapiens

<400> SEQUENCE: 5
ttataatacc ttatacagtg cctgcccatc acttgactct tatgggttca rcataggagt    60
cagcatgcag caaattcaag ctttacttct gggacttggg g                        101

<210> SEQ ID NO 6
<211> LENGTH: 101
<212> TYPE: DNA
<213> ORGANISM: Homo sapiens

<400> SEQUENCE: 6
aagatagtgt tgtgcatgta aagatctaag aacttgatat ttctatgaaa kcacaatgac    60
tgagcaatag tcctttgcct tagttttat tccattgagt g                         101

<210> SEQ ID NO 7
<211> LENGTH: 101
<212> TYPE: DNA
<213> ORGANISM: Homo sapiens

<400> SEQUENCE: 7
cgagggatag tacttaagtt tccaaaggac catatatagg tttaggaaac rtcgaatatt    60
accattgttt tgattggttc tagttacttt atagtttatt t                        101
```

```
<210> SEQ ID NO 8
<211> LENGTH: 101
<212> TYPE: DNA
<213> ORGANISM: Homo sapiens

<400> SEQUENCE: 8
gtacttaagt tccaaagga ccatatatag gtttaggaaa catcgaatat yaccattgtt      60
ttgattggtt ctagttactt tatagtttat tttaaaattt c                        101

<210> SEQ ID NO 9
<211> LENGTH: 101
<212> TYPE: DNA
<213> ORGANISM: Homo sapiens

<400> SEQUENCE: 9
aaaatttaat ttaaaaatta gatgatttat ttggaagaag cattttaga yaggtggcaa     60 tatcctctct agacaattct ccctgtaggg gtcaagcttt t                         101

<210> SEQ ID NO 10
<211> LENGTH: 101
<212> TYPE: DNA
<213> ORGANISM: Homo sapiens

<400> SEQUENCE: 10
aaacctttaa cttaaaatta gaagcaagtc tgatcaagaa gtctcaagca maggctgagt     60
agtaatattt aagacaacac tgcttactaa agaaaagagt t                         101

<210> SEQ ID NO 11
<211> LENGTH: 101
<212> TYPE: DNA
<213> ORGANISM: Homo sapiens

<400> SEQUENCE: 11
aggtcatatg tactaaaaca gtttatccaa aaaggccttt ctaagacaca ytattttcaa     60
actcaaaagt caaaaacaaa gaaaaaattc ttatggaacc a                         101

<210> SEQ ID NO 12
<211> LENGTH: 101
<212> TYPE: DNA
<213> ORGANISM: Homo sapiens

<400> SEQUENCE: 12
gtgtttatgt aatacatata taatcactga aaaattactg aattgtatga magtaatgta     60
agtgaaaata cttgttcttt aagtggtaag ttaaagttgt t                         101

<210> SEQ ID NO 13
<211> LENGTH: 101
<212> TYPE: DNA
<213> ORGANISM: Homo sapiens

<400> SEQUENCE: 13
atttctgcaa cccaaattcc gtggtctcct catagggcac gagggccatt mcgcctgcac     60
cccgccctct gctcagacct gccgtgcaaa agaatcctgg g                         101

<210> SEQ ID NO 14
<211> LENGTH: 101
<212> TYPE: DNA
<213> ORGANISM: Homo sapiens

<400> SEQUENCE: 14
```

```
ctctgtctca aaaaaaaaaa aaatagtgct ttttactttt atctgaatga ytgaaatgtc    60
cttttcccaa tcctatgatg cctgactgca aaataatggt a                       101
```

<210> SEQ ID NO 15
<211> LENGTH: 101
<212> TYPE: DNA
<213> ORGANISM: Homo sapiens

<400> SEQUENCE: 15

```
aacactgact tcctatcact gactgtaaat atacaactga tacattatca rttttcttgt    60
tatctttaac gtgaaagcag tatagagaga gtgtgttcaa a                       101
```

<210> SEQ ID NO 16
<211> LENGTH: 101
<212> TYPE: DNA
<213> ORGANISM: Homo sapiens

<400> SEQUENCE: 16

```
ctggctgtcc agtccccact ccacaccaca gagcaacacc tagccaaaga rggtaggtaa    60
gaaaagctaa acacccaggg atatgaaacc agccttcaca g                       101
```

<210> SEQ ID NO 17
<211> LENGTH: 101
<212> TYPE: DNA
<213> ORGANISM: Homo sapiens

<400> SEQUENCE: 17

```
tggcaatttt tgaataaaaa gattaactac taattctgag gcagtggaga ytgaggagaa    60
taagaaagat ggccagcact gcttgcttct ctggctgtcc a                       101
```

<210> SEQ ID NO 18
<211> LENGTH: 101
<212> TYPE: DNA
<213> ORGANISM: Homo sapiens

<400> SEQUENCE: 18

```
agtcctcctg ttccctgtga gagcacttca agtgctgggg ccaggtctga kgcagctctg    60
attcctacac agcaaagcct ggcccaggta aggggatggg a                       101
```

<210> SEQ ID NO 19
<211> LENGTH: 101
<212> TYPE: DNA
<213> ORGANISM: Homo sapiens

<400> SEQUENCE: 19

```
ggagacgcgg tgtgtgtagg ggcgctacta agatttggag gctactggga yggaagcgga    60
ataacataaa agggacagta cagtcaaggg tactggtggg a                       101
```

<210> SEQ ID NO 20
<211> LENGTH: 101
<212> TYPE: DNA
<213> ORGANISM: Homo sapiens

<400> SEQUENCE: 20

```
gttgccaacc taagacgact gtcagagagt ccatgcatta tggacagagt rgctggatgg    60
ggacgtggaa gcacacagca tccacctctc tgactgcctc t                       101
```

<210> SEQ ID NO 21
<211> LENGTH: 101

```
<212> TYPE: DNA
<213> ORGANISM: Homo sapiens

<400> SEQUENCE: 21 cccctctaa caataaattc tcacacctgg gtcaagctct tcacttttag ygctaccta      60 ggcaggagtg tcccaaccca atcaagagcg gtgcctaccc g                       101

<210> SEQ ID NO 22
<211> LENGTH: 101
<212> TYPE: DNA
<213> ORGANISM: Homo sapiens

<400> SEQUENCE: 22
aatgtcctgg tagccacaag gaactgtggt agctgctgtc ccagcagcag magaacgaca   60
ctttgtgagg cttaggtgct ggccagggag gtgaggataa c                       101

<210> SEQ ID NO 23
<211> LENGTH: 101
<212> TYPE: DNA
<213> ORGANISM: Homo sapiens

<400> SEQUENCE: 23
gatagtatca aaaacggtg aagagagctg atgaggctgt ggggactggc yggaagctgc    60
tggcagggtg gagtgggctg ggccccggc agattcagat c                        101

<210> SEQ ID NO 24
<211> LENGTH: 101
<212> TYPE: DNA
<213> ORGANISM: Homo sapiens

<400> SEQUENCE: 24
agctttaggc cccgcagatc cctacagttt ctctcccact atgttctggc ycaaagctgc   60
ctcacggaaa tgcctcaagg atttctacct tgcaagcccg a                       101

<210> SEQ ID NO 25
<211> LENGTH: 101
<212> TYPE: DNA
<213> ORGANISM: Homo sapiens

<400> SEQUENCE: 25
gaacttggac ttttacataa tatgtgaaag tcataaaata ttttgatgta ygggttcaat   60
ctgcaaacat ttattaaaga tcagctaggt ggcagattct a                       101

<210> SEQ ID NO 26
<211> LENGTH: 101
<212> TYPE: DNA
<213> ORGANISM: Homo sapiens

<400> SEQUENCE: 26
ctcccagctg cgttttgcac caggaccttg gtgtcctcca ccagcacctt ygcagtcttc   60
aggatgccct ccctgaggga gggcccagct tagtcagatc t                       101

<210> SEQ ID NO 27
<211> LENGTH: 101
<212> TYPE: DNA
<213> ORGANISM: Homo sapiens

<400> SEQUENCE: 27 cataaccca tacaggccac atggtaatcc acggccctct gattcccaca ytcaagcata    60
```
aagtgctcct ccccttctcc ccactgtgct taacacaatc c    101

<210> SEQ ID NO 28
<211> LENGTH: 101
<212> TYPE: DNA
<213> ORGANISM: Homo sapiens

<400> SEQUENCE: 28
gtggattacc aaacaactat ggtgcggaca gccaaggcca ttgcagtgac ygttcaggag    60
atggtgagtt tgggcgagtc ccagaggact gccctcggag a    101

<210> SEQ ID NO 29
<211> LENGTH: 101
<212> TYPE: DNA
<213> ORGANISM: Homo sapiens

<400> SEQUENCE: 29
tgcccatcct ccattctgcc acaatgtatg cccccagcc acactggttc yccatccctc    60
aatacctcat gcttgtaatt agcttcttga tggagtctga g    101

<210> SEQ ID NO 30
<211> LENGTH: 101
<212> TYPE: DNA
<213> ORGANISM: Homo sapiens

<400> SEQUENCE: 30
cagagatacc caaagatgaa ctgggcatgg gagaggaaag acatactaat rgagaaacca    60
taagagggca tgtgggagag taagctcgaa catctacaga g    101

<210> SEQ ID NO 31
<211> LENGTH: 101
<212> TYPE: DNA
<213> ORGANISM: Homo sapiens

<400> SEQUENCE: 31
atgttgggtc ttagagtgaa aagtatggct tactgtaagt agcagtaaaa mgtttgagag    60
ccatatataa atacacacct ttgtgcacac aagcaaagcc t    101

<210> SEQ ID NO 32
<211> LENGTH: 101
<212> TYPE: DNA
<213> ORGANISM: Homo sapiens

<400> SEQUENCE: 32
gagcttcttg aaatgtccca gtgctaggag gaagctgcaa ggtgagaggg kaagtcagac    60
agaagagtgg ggaatgatgc agggagaagt ctggtaaagg a    101

<210> SEQ ID NO 33
<211> LENGTH: 101
<212> TYPE: DNA
<213> ORGANISM: Homo sapiens

<400> SEQUENCE: 33
ctggcattct ttgactccta cgttccccca cccctaccg tcctcctacc ragtcactca    60
ggagtcgctt gctggcatct ccaactgccc tcagggcatt a    101

<210> SEQ ID NO 34
<211> LENGTH: 101
<212> TYPE: DNA

```
<400> SEQUENCE: 34
ccagctccca ttttcctacc tccctcacaa tatgccccat gcctggctct ytgcccacat    60
acctgcataa ttctcattgc cctgggcaac ctctcccagt a                      101

<210> SEQ ID NO 35
<211> LENGTH: 101
<212> TYPE: DNA
<213> ORGANISM: Homo sapiens

<400> SEQUENCE: 35
cctcccgaag tgttaggatt gcaggcatga gccaccacac ctggcctaaa rttatttttt    60
aattgacata attttacata ttcatgaggt acatagtgac a                      101

<210> SEQ ID NO 36
<211> LENGTH: 101
<212> TYPE: DNA
<213> ORGANISM: Homo sapiens

<400> SEQUENCE: 36
atggggaaga atttagcaaa gagtttcata tcacagctaa ggaattaagg ytggatgcta    60
actctaacga gagagaatta tggggacact ggaaaggttg a                      101

<210> SEQ ID NO 37
<211> LENGTH: 101
<212> TYPE: DNA
<213> ORGANISM: Homo sapiens

<400> SEQUENCE: 37
tcagattatg ctacctcatt tgatcctatc agtcctacac ggggcaagta ytgttatccc    60
aaatcagagg taaataaaag attacaagaa tattgaactg a                      101

<210> SEQ ID NO 38
<211> LENGTH: 101
<212> TYPE: DNA
<213> ORGANISM: Homo sapiens

<400> SEQUENCE: 38
atgtagttca gtatctctgc ccctaccccc atctctgaag caagcatgtc rctcttttt    60 gagattatct gaagaatttt gctgcagtag ccagagggaa a                      101

<210> SEQ ID NO 39
<211> LENGTH: 101
<212> TYPE: DNA
<213> ORGANISM: Homo sapiens

<400> SEQUENCE: 39
ttatctggtc aactcttgtg ttttggagaa ggggaaatag actctgggag kccaggaaac    60
attttcaaga caggccagag aaaggaccca gtccctgtaa c                      101

<210> SEQ ID NO 40
<211> LENGTH: 101
<212> TYPE: DNA
<213> ORGANISM: Homo sapiens

<400> SEQUENCE: 40
tctcaccaga ggcttccgtg cttgaggagg aagggggtgt ctaagtgtcc rgaggaaatg    60
gggggagaca tgcagtttca gcttagtgtg aagggtcctt t                      101
```

<210> SEQ ID NO 41
<211> LENGTH: 101
<212> TYPE: DNA
<213> ORGANISM: Homo sapiens

<400> SEQUENCE: 41
acaagtatga gtagaagcta gctcattcct cctttggcct gagaactttg mtcccttttc    60
cattgtgttt gatggaacag caactcccca ctgccgtgtc c                       101

<210> SEQ ID NO 42
<211> LENGTH: 101
<212> TYPE: DNA
<213> ORGANISM: Homo sapiens

<400> SEQUENCE: 42
ggtccctatt tcccacctat gttgtctgta acaacacag tccagaatct ytgtcccta     60 actgtggtgg ccacagcaag ggccttgggc ttagagaatg g                       101

<210> SEQ ID NO 43
<211> LENGTH: 101
<212> TYPE: DNA
<213> ORGANISM: Homo sapiens

<400> SEQUENCE: 43
tttttttaat agtttaaaat ggtctggctt gttagggtta cacctggtc ygtggaggca    60 ttcagaaaga atctgaatgc ctgttggtca gggaagctgt a                       101

<210> SEQ ID NO 44
<211> LENGTH: 101
<212> TYPE: DNA
<213> ORGANISM: Homo sapiens

<400> SEQUENCE: 44
aaggaacatg tacctcccaa gatggaaagg atttgggggt tcagcagagt rggatcatca   60
aatgaatccc agtgcaagtc tactgactttt ggtgggtgga g                      101

<210> SEQ ID NO 45
<211> LENGTH: 101
<212> TYPE: DNA
<213> ORGANISM: Homo sapiens

<400> SEQUENCE: 45
attccagatg cgggcgccgg tcgttgttag gtatcgtccc ggagggccgg kcgttgggga   60
aagcttaaat gagctggtgt ttcagtggag ccggggagct c                       101

<210> SEQ ID NO 46
<211> LENGTH: 101
<212> TYPE: DNA
<213> ORGANISM: Homo sapiens

<400> SEQUENCE: 46
ttggctgggg aggcgctgga gtgtgtagtg accgtcacca accccctcc scccacggcc    60 acttctgcat ccaggtgggg atgctggcac tgaaggtggt g                       101

<210> SEQ ID NO 47
<211> LENGTH: 101
<212> TYPE: DNA
<213> ORGANISM: Homo sapiens

<400> SEQUENCE: 47

-continued tttagccatc tcatgttaga atctaaaacc ctaacctcta ctctcatctc ygttccctct      60
cagcattacc tctccactca ttctttctct aggccttcag g                          101

<210> SEQ ID NO 48
<211> LENGTH: 101
<212> TYPE: DNA
<213> ORGANISM: Homo sapiens

<400> SEQUENCE: 48
gagggtgtaa tggatcctga ttccttatac acactcccag acatacccac rtctagcctc      60
tgacccggaa cagtttctca gaccttcaac ctcttcctgt t                          101

<210> SEQ ID NO 49
<211> LENGTH: 101
<212> TYPE: DNA
<213> ORGANISM: Homo sapiens

<400> SEQUENCE: 49
agtacgcact atccccgtat ttagtttgtc tttcctgttt cacagctgga rgaagcctgg      60
gtattttgac acgggatcat ctgtaaggcc ccatcctccc t                          101

<210> SEQ ID NO 50
<211> LENGTH: 101
<212> TYPE: DNA
<213> ORGANISM: Homo sapiens

<400> SEQUENCE: 50 tggaggggc actggactgg gcacttcccc agcaaggagg caggaggggc ragggccccc      60
aggtggtccc cagatctctt ccctgacctg gagagaagga a                          101

<210> SEQ ID NO 51
<211> LENGTH: 101
<212> TYPE: DNA
<213> ORGANISM: Homo sapiens

<400> SEQUENCE: 51
ctggcgcgca ggtcccggag ggggcggctg gcgcgcacta cacgcttggg racaaggaaa      60
acatccgccg gaggcccggc cgggcggcgc tccagcctcg g                          101

<210> SEQ ID NO 52
<211> LENGTH: 101
<212> TYPE: DNA
<213> ORGANISM: Homo sapiens

<400> SEQUENCE: 52
gtcgtggtgt cgctacgggc gcgaaacgga cactgaacac agtctgactg watggaggca      60
ggtggggagg gatcccctgg gagaacttgg cgggccgaga g                          101

<210> SEQ ID NO 53
<211> LENGTH: 101
<212> TYPE: DNA
<213> ORGANISM: Homo sapiens

<400> SEQUENCE: 53
gtcgtggtgt cgctacgggc gcgaaacgga cactgaacac agtctgactg watggaggca      60
ggtggggagg gatcccctgg gagaacttgg cgggccgaga g                          101

<210> SEQ ID NO 54

-continued

```
<211> LENGTH: 101
<212> TYPE: DNA
<213> ORGANISM: Homo sapiens

<400> SEQUENCE: 54
ttggataaca aattaacctc catttccact ggacagagaa ctcattcttc yggtatgttt      60
cagaaggcta atggagcaag gataaaccta tattactaat g                         101

<210> SEQ ID NO 55
<211> LENGTH: 101
<212> TYPE: DNA
<213> ORGANISM: Homo sapiens

<400> SEQUENCE: 55
tggctagtgt tttttgtatc ctgcataaga aatcttccct tacaccaggt yacaaagatt     60
tttttcctac attttctcct atatctaaaa gttttatgat t                         101

<210> SEQ ID NO 56
<211> LENGTH: 101
<212> TYPE: DNA
<213> ORGANISM: Homo sapiens

<400> SEQUENCE: 56
agacatcatt aaattcatca tggcattctt tcttgctgag cctggacata rcctggtaag     60
actagaacta gataatagga aagaaatgt agacattaag t                         101

<210> SEQ ID NO 57
<211> LENGTH: 101
<212> TYPE: DNA
<213> ORGANISM: Homo sapiens

<400> SEQUENCE: 57
tgggagaggc tggcatcaaa ttactcctct gttttctct cttggtgacc yagcaggtgt      60
ttaggacaat gacgactact catgtggaac ctttgcagtc a                         101

<210> SEQ ID NO 58
<211> LENGTH: 101
<212> TYPE: DNA
<213> ORGANISM: Homo sapiens

<400> SEQUENCE: 58
aatcaccatt ttatgtgaac aaattgaagt ctttatagca ttcttaattt sgtttctgaa     60
agacatttag ataattgggc aatttacaaa agagtatgtt c                         101

<210> SEQ ID NO 59
<211> LENGTH: 101
<212> TYPE: DNA
<213> ORGANISM: Homo sapiens

<400> SEQUENCE: 59
caagtttcat ccacgttgta gcgtgtatca aaacttcaat taatattctt ytatatgggt     60
atgttacatt ttgtttatcc attcatcagt tggtagacat g                         101

<210> SEQ ID NO 60
<211> LENGTH: 101
<212> TYPE: DNA
<213> ORGANISM: Homo sapiens

<400> SEQUENCE: 60
gctgctgtgg acatttgcat acaagttttt ttgtgtggaa atatgttttc rattctcttg     60
```
ggaatatacc taggactgga atgggtcatt tggaaactac g         101

<210> SEQ ID NO 61
<211> LENGTH: 101
<212> TYPE: DNA
<213> ORGANISM: Homo sapiens

<400> SEQUENCE: 61
attcaaaaat aacaggattg tgaaatatcc aactaaaatc atatttgaaa rtggtccagg    60
aatccccaaa taacttttat gcatgttata tgaagataaa t                      101

<210> SEQ ID NO 62
<211> LENGTH: 101
<212> TYPE: DNA
<213> ORGANISM: Homo sapiens

<400> SEQUENCE: 62
ccttcctttc agcatgcaga attgaacttg gctctgaagt aaaacaatac rggttttga    60 gtgatccagc agctgttcta ctttggtgag agttttcttc t                      101

<210> SEQ ID NO 63
<211> LENGTH: 101
<212> TYPE: DNA
<213> ORGANISM: Homo sapiens

<400> SEQUENCE: 63
gtcctcaatt acatctttgt gagaatcaaa tgtgataagg cataacactc ytggcatggt    60
ggctttagat attaacaact cttgctatgt tggttgtgct t                      101

<210> SEQ ID NO 64
<211> LENGTH: 101
<212> TYPE: DNA
<213> ORGANISM: Homo sapiens

<400> SEQUENCE: 64
attagtttct ggctattgca gctaattctc gggtaaagaa tttgaatggc rttctagtat    60
tgcattttac ctagactaca ctgttacaga attgtgtgta g                      101

<210> SEQ ID NO 65
<211> LENGTH: 101
<212> TYPE: DNA
<213> ORGANISM: Homo sapiens

<400> SEQUENCE: 65
tatcacaggg ttctttgttg gctatttatt gacccatctt ctctcaggca ygtatattct    60
ctgggcaagt atagactcac aagtgcctgg agtccctcct c                      101

<210> SEQ ID NO 66
<211> LENGTH: 101
<212> TYPE: DNA
<213> ORGANISM: Homo sapiens

<400> SEQUENCE: 66
atcagtacat caaacaactc aattaacaaa tgcttgcatc tgcaatgttc rttataatac    60
agcatcatag ttgcagaatt aaaatggcaa gattataaaa c                      101

<210> SEQ ID NO 67
<211> LENGTH: 101
<212> TYPE: DNA

<213> ORGANISM: Homo sapiens

<400> SEQUENCE: 67
ggaagtagga ccaccatcgg cccatacaac ttaagtccaa tatatagact yttaacctat    60
gtcagtgtga atagttgcct gcttgaccag ggactttaat t                        101

<210> SEQ ID NO 68
<211> LENGTH: 101
<212> TYPE: DNA
<213> ORGANISM: Homo sapiens

<400> SEQUENCE: 68
tccagtcaga tgactatttg ttcaaatatt tattctacta catgacacac ygtgctggac    60
acttcagaga tagctgtgag ttttgcttcc tgtgtggtag c                        101

<210> SEQ ID NO 69
<211> LENGTH: 101
<212> TYPE: DNA
<213> ORGANISM: Homo sapiens

<400> SEQUENCE: 69
gtgggatgca ggacaaagtg tttactttttg tctttcagag tcaaaatggg maaggttaac   60
acaaggagta aactaagaaa atatatccat atccatattc a                        101

<210> SEQ ID NO 70
<211> LENGTH: 101
<212> TYPE: DNA
<213> ORGANISM: Homo sapiens

<400> SEQUENCE: 70
aactggcttc agccaattac tatacctgtt tcctctggct atagtgattg rttcagggag    60
aggcccttaa tctagtagct gttgagatgg aaaaaaaaac a                        101

<210> SEQ ID NO 71
<211> LENGTH: 101
<212> TYPE: DNA
<213> ORGANISM: Homo sapiens

<400> SEQUENCE: 71
gagatagttc ctattcagga cacacaccca gtgcttgcag atccatactg ytagactacg    60
tgaaggagga agaaagatgt ttgcaaagga gccaaggggg a                        101

<210> SEQ ID NO 72
<211> LENGTH: 101
<212> TYPE: DNA
<213> ORGANISM: Homo sapiens

<400> SEQUENCE: 72
atccatactg ctagactacg tgaaggagga agaaagatgt ttgcaaagga rccaaggggg    60
aaagcaggtt gcctgcacca agatcagact gtctcttgtg t                        101

<210> SEQ ID NO 73
<211> LENGTH: 101
<212> TYPE: DNA
<213> ORGANISM: Homo sapiens

<400> SEQUENCE: 73
gatgtttgca aaggagccaa gggggaaagc aggttgcctg caccaagatc rgactgtctc    60
ttgtgttctt tgataactct gagattttcc tttcctattc c                        101

<210> SEQ ID NO 74
<211> LENGTH: 101
<212> TYPE: DNA
<213> ORGANISM: Homo sapiens

<400> SEQUENCE: 74
ctttcttccc atctattaat gagcatgaac tacatcctgg cctttaatca ytgatatcat    60
ttcatatata cttttttcatt atcctcatct ctcctttgct t                      101

<210> SEQ ID NO 75
<211> LENGTH: 101
<212> TYPE: DNA
<213> ORGANISM: Homo sapiens

<400> SEQUENCE: 75 cattttttcat agagtctttg gcattgggtt ggacaatgat ggaaattagt sagttttact   60
cagacaaggt cccttccttt gaggaattta tcctccataa t                       101

<210> SEQ ID NO 76
<211> LENGTH: 101
<212> TYPE: DNA
<213> ORGANISM: Homo sapiens

<400> SEQUENCE: 76
tggtatttcc agggaagaat acattagtaa tgcaggcttg ggtaaccact ygcagctcac   60
ctcactactg agcaatgacg tggaattgga gctggtatca c                       101

<210> SEQ ID NO 77
<211> LENGTH: 101
<212> TYPE: DNA
<213> ORGANISM: Homo sapiens

<400> SEQUENCE: 77
atcagagcct gagccaataa tatgagctgt cttcttggat agcttgggct rggctccaca   60
acagaagaag ctggggcaaa ttggctctgt tgctgagacc t                       101

<210> SEQ ID NO 78
<211> LENGTH: 101
<212> TYPE: DNA
<213> ORGANISM: Homo sapiens

<400> SEQUENCE: 78
ttctggcagt gtgaacttca atggcccaca taatttttt gacctaatgt rtaaacattt    60
tacctcatgt gtagaaatag ggacaatggt actacctcgt g                       101

<210> SEQ ID NO 79
<211> LENGTH: 101
<212> TYPE: DNA
<213> ORGANISM: Homo sapiens

<400> SEQUENCE: 79
atcctcattt taaagggaag gaaaccaatg agagtgaaat ttaagaaaca katcagatta   60
ttgggaaatg gagtattctt cccagagctc ctcaaaatat c                       101

<210> SEQ ID NO 80
<211> LENGTH: 101
<212> TYPE: DNA
<213> ORGANISM: Homo sapiens

<400> SEQUENCE: 80
gagtacccct taactcagtg aggtagacac ccaaaagcaa ccatcctgca yttttttccg    60
tgagcattaa taaagtctat tgttcattgt agaatgttct g                       101

<210> SEQ ID NO 81
<211> LENGTH: 101
<212> TYPE: DNA
<213> ORGANISM: Homo sapiens

<400> SEQUENCE: 81
tcccatcttt ctcaccatta acatgtacac attatgccta acacgaatcc rccaatccct    60
tgcagccact ggcatgctca ttggtctctg cctccagacc c                       101

<210> SEQ ID NO 82
<211> LENGTH: 101
<212> TYPE: DNA
<213> ORGANISM: Homo sapiens

<400> SEQUENCE: 82
tccttgctta cttctttctc aatcacgcat aatgcctcaa ctcttagagc yggcatttgt    60
tgtatcagtc ctaataactc ttgaggtatc tctgaaatca g                       101

<210> SEQ ID NO 83
<211> LENGTH: 101
<212> TYPE: DNA
<213> ORGANISM: Homo sapiens

<400> SEQUENCE: 83
taaagacttg gaaagtgtca cattgtagta cagtggggtt ttctcctgat rgctacaatt    60
tacatgccag gagccctgta agccctctag cattttcttg a                       101

<210> SEQ ID NO 84
<211> LENGTH: 101
<212> TYPE: DNA
<213> ORGANISM: Homo sapiens

<400> SEQUENCE: 84
cataatttta tcaaattttt tttcacatac gttggcatgg tcttcagacc ygtggtaata    60
atcacacctc tcttaacggg tggcgtgctg atcaaataag t                       101

<210> SEQ ID NO 85
<211> LENGTH: 101
<212> TYPE: DNA
<213> ORGANISM: Homo sapiens

<400> SEQUENCE: 85
ctgttgagtg ttcaagtctg atttggcttc accaagaata gaacaatgtt yctaaaagt    60 ttgtcatgaa gagaagccca tttagaaatt catcctctaa c                       101

<210> SEQ ID NO 86
<211> LENGTH: 101
<212> TYPE: DNA
<213> ORGANISM: Homo sapiens

<400> SEQUENCE: 86
gggaggtgta ttaacttttg cctatggagc tagtaacagg tagaaccggg mttctttttt    60
ttcatcattt tttattatgt aaaatatata taacaaaatt t                       101

-continued

```
<210> SEQ ID NO 87
<211> LENGTH: 101
<212> TYPE: DNA
<213> ORGANISM: Homo sapiens

<400> SEQUENCE: 87
aagttcagag taacttccca gattttaaat attctgtgtc atgtaagaac raggaggaat      60
cgctgatcaa ttaggtttaa aagctactga aattctcaag a                         101

<210> SEQ ID NO 88
<211> LENGTH: 101
<212> TYPE: DNA
<213> ORGANISM: Homo sapiens

<400> SEQUENCE: 88
cggctgtcaa atctcttgct gtctgctgcc tttcctctca gcatgtgagc rtggagctgg     60
gggtctggtg gatcctgtca atcatatgtc tgtgggcagc a                         101

<210> SEQ ID NO 89
<211> LENGTH: 101
<212> TYPE: DNA
<213> ORGANISM: Homo sapiens

<400> SEQUENCE: 89
tttatcatat gtatctccag cttgcacctc tctccttggc aatggccttc rctgcacctt     60
tgacattttc caactgcgcc tttgacattt tcctctagat g                         101

<210> SEQ ID NO 90
<211> LENGTH: 101
<212> TYPE: DNA
<213> ORGANISM: Homo sapiens

<400> SEQUENCE: 90
ctcagacttt ctttgatgga gccagcctcc ttgaaagcag ttattttag rtgttccaac      60 agccatctat cttacaaaag gattttctct tcagataggc t                         101

<210> SEQ ID NO 91
<211> LENGTH: 101
<212> TYPE: DNA
<213> ORGANISM: Homo sapiens

<400> SEQUENCE: 91
agaggagctc agtcaatggt gagatcgaat ctttggacct cctttggacc rccggaatga     60
aatcacacgt tccctacaat aacaagagaa gctgttattt t                         101

<210> SEQ ID NO 92
<211> LENGTH: 101
<212> TYPE: DNA
<213> ORGANISM: Homo sapiens

<400> SEQUENCE: 92
ctcaccttat ttccatgatg cttggttgtc agtgaacgca gatattggag ytaaggccag     60
tgtttgtccc agggccccag atccaactgg agtgaatatt a                         101

<210> SEQ ID NO 93
<211> LENGTH: 101
<212> TYPE: DNA
<213> ORGANISM: Homo sapiens

<400> SEQUENCE: 93
```

```
tttctatggg tgctattaag catataaaat ttttttttcaa aaggactgag ytgagttggt    60
atgccactgt gaacagtaac ttcatcactt ggaagatccg a                        101
```

<210> SEQ ID NO 94
<211> LENGTH: 101
<212> TYPE: DNA
<213> ORGANISM: Homo sapiens

<400> SEQUENCE: 94

```
atttcctcat ggtagcattt gaaccaagcc tttaagtaga acaagatttt rctaaacata    60
gaaggcagaa agggcactgc tgactagcta tttgaagaaa a                        101
```

<210> SEQ ID NO 95
<211> LENGTH: 101
<212> TYPE: DNA
<213> ORGANISM: Homo sapiens

<400> SEQUENCE: 95

```
tcattggtgg atctggagag tagctgacct gaaaacagtc ttcatctttc ygccaaaata    60
attttaacac ttaaaaaaaa ttttttttgag aaggtactag a                       101
```

<210> SEQ ID NO 96
<211> LENGTH: 101
<212> TYPE: DNA
<213> ORGANISM: Homo sapiens

<400> SEQUENCE: 96

```
ctgagacaca gtgggccttg gaaatggcag ttcccatagg gagtcctgca ygagccatga    60
aggcgagaag ccaaggcttt gcatgctatg ctttgggtgt g                        101
```

<210> SEQ ID NO 97
<211> LENGTH: 101
<212> TYPE: DNA
<213> ORGANISM: Homo sapiens

<400> SEQUENCE: 97

```
tgcagatctg atgacagtac atccacaccc tgtcgctttc cctgccaaga ygaactgtag    60
ccgtcagagc ctccattctg ctccccacac ccatccagtg a                        101
```

<210> SEQ ID NO 98
<211> LENGTH: 101
<212> TYPE: DNA
<213> ORGANISM: Homo sapiens

<400> SEQUENCE: 98

```
tgacagtaca tccacaccct gtcgctttcc ctgccaagac gaactgtagc ygtcagagcc    60
tccattctgc tccccacacc catccagtga ccatccacta a                        101
```

<210> SEQ ID NO 99
<211> LENGTH: 101
<212> TYPE: DNA
<213> ORGANISM: Homo sapiens

<400> SEQUENCE: 99

```
tcttctgcac tccagcctct ccctctactt ccctcctttt tgcttcagcc mgaggcagat    60
ggcagacatg gatacacatt tatggattgg ctgatgtgtc t                        101
```

<210> SEQ ID NO 100
<211> LENGTH: 101

```
<212> TYPE: DNA
<213> ORGANISM: Homo sapiens

<400> SEQUENCE: 100
gggtgacgta aggggggtgca gagattccca cttgggttta tgctggcctc rtctttgact    60
ggctctgtca tgttgccctt gtgggtcct gttttcatta a                          101

<210> SEQ ID NO 101
<211> LENGTH: 101
<212> TYPE: DNA
<213> ORGANISM: Homo sapiens

<400> SEQUENCE: 101
ttttgcacgg taaatgcttc gtaaacgtca gctattcatt agtgaggtgt ygggggagttg    60 tcgggggaag agagaggaga aagaaggaag tgagagggga g                         101

<210> SEQ ID NO 102
<211> LENGTH: 101
<212> TYPE: DNA
<213> ORGANISM: Homo sapiens

<400> SEQUENCE: 102
aaaaagaaag agccagcctt taaggaaacg ggaagtcaaa gcttgtgtaa ygaagcaaga     60
ccagactttt taaatctacc tcccttaacc tttataaaca t                         101

<210> SEQ ID NO 103
<211> LENGTH: 101
<212> TYPE: DNA
<213> ORGANISM: Homo sapiens

<400> SEQUENCE: 103
atggtgctac ataggctggc ttaacatctt tttttgaaat aaaaaccaag ygtaaacatg     60
agtcagaatg acagggcata tgcaggactc caacatttac t                         101

<210> SEQ ID NO 104
<211> LENGTH: 101
<212> TYPE: DNA
<213> ORGANISM: Homo sapiens

<400> SEQUENCE: 104
tgaatttgat gctgttctct tggtcttttt cacaactgaa acattgggcc rttggtggga     60
cgttctgtgc cttgaaactt ttaatacgtg cagctccatc t                         101

<210> SEQ ID NO 105
<211> LENGTH: 101
<212> TYPE: DNA
<213> ORGANISM: Homo sapiens

<400> SEQUENCE: 105
gtcttctccc caagaggcca cctttttgac caggtgactc tcctcagtga ygatatggtg     60
caatttttat gagattttgg gatgtgaagc agctctgtag a                         101

<210> SEQ ID NO 106
<211> LENGTH: 101
<212> TYPE: DNA
<213> ORGANISM: Homo sapiens

<400> SEQUENCE: 106
tgctaacagt gcccttgggg aatgtttgga gggacttgat tccagatcag raaagataaa    60
```

```
cagtgatctg agggtctgg tttagatgca agtcatattt c                          101
```

<210> SEQ ID NO 107
<211> LENGTH: 101
<212> TYPE: DNA
<213> ORGANISM: Homo sapiens

<400> SEQUENCE: 107

```
caccctttac atacctgtgt ccctggatct tcctttctcc atggtcctca yagcctctct    60
tcttttacac ttacctctcc ttgagctccc tgatgtgcct t                         101
```

<210> SEQ ID NO 108
<211> LENGTH: 101
<212> TYPE: DNA
<213> ORGANISM: Homo sapiens

<400> SEQUENCE: 108

```
tggttctgac aagaaaaaga aagtattcat atttggtgga cgtggtggta rgtaaactac    60
taatttgtaa acattggaaa tttttacttt aagtgagagc a                        101
```

<210> SEQ ID NO 109
<211> LENGTH: 101
<212> TYPE: DNA
<213> ORGANISM: Homo sapiens

<400> SEQUENCE: 109

```
agctgttgag cacactcgcc tgtggttgac aggactctgg cacaagtgcc rtggaggatg    60
atgttagaga ggtggacaca tggggtcaga agaggaagga g                        101
```

<210> SEQ ID NO 110
<211> LENGTH: 101
<212> TYPE: DNA
<213> ORGANISM: Homo sapiens

<400> SEQUENCE: 110

```
attcaccgca tacattcacg caaaggggaa aatttactgc ctaaacagag rgacctaaat    60
cccccaggct aaataaaccc aatgaaaaca caagaactgc a                        101
```

<210> SEQ ID NO 111
<211> LENGTH: 101
<212> TYPE: DNA
<213> ORGANISM: Homo sapiens

<400> SEQUENCE: 111

```
taaaaaggtt tcttcaaatg aaaatggat ggctgagctg ctaatggccc rgtaacctaa     60
aaatttaact cttccctaat gctcagggac ctcaggtaag g                        101
```

<210> SEQ ID NO 112
<211> LENGTH: 101
<212> TYPE: DNA
<213> ORGANISM: Homo sapiens

<400> SEQUENCE: 112

```
tttttgtcct ttattatttt ttgaattact ttgctttatt tttcatgtgt raaaacacca    60
tatggtggcc acagtgggaa gccaggtcct ctgcactaag a                        101
```

<210> SEQ ID NO 113
<211> LENGTH: 101
<212> TYPE: DNA
<213> ORGANISM: Homo sapiens

<400> SEQUENCE: 113
ataggaggtt aggtatggtt ctgacattgc aatattctct tcaagttaac rgcaggcatt    60
tgttacatgc tcagagaatt ttatgattta taaagaactt t                        101

<210> SEQ ID NO 114
<211> LENGTH: 101
<212> TYPE: DNA
<213> ORGANISM: Homo sapiens

<400> SEQUENCE: 114
ttcatttacg ttatcaactt aattaattta tttataaaat ttccatgacc rtaggatgac    60
cacgtagaag tgtggactat ggatcactag catcaaaatc t                        101

<210> SEQ ID NO 115
<211> LENGTH: 101
<212> TYPE: DNA
<213> ORGANISM: Homo sapiens

<400> SEQUENCE: 115
caggaaagcc atctttacat cacctctatt taaagcacag ggtccctttt rcctatgtca    60
ctgaaaaaca gcagaagcct ggtatctagt ggattcaccc c                        101

<210> SEQ ID NO 116
<211> LENGTH: 101
<212> TYPE: DNA
<213> ORGANISM: Homo sapiens

<400> SEQUENCE: 116
atgcaatctg atttatttcc atggattctg agctaggaat cgcaattggg matctccaga    60
accaatgggg atttttgctg taggaccatc gttcttttct g                        101

<210> SEQ ID NO 117
<211> LENGTH: 101
<212> TYPE: DNA
<213> ORGANISM: Homo sapiens

<400> SEQUENCE: 117
ttttccaaag cagcttaatg tagaacaata gggccaagaa ggggtttttt ygctctgaaa    60
aataccgagt cccctgccca agagctccag tgcctccctc c                        101

<210> SEQ ID NO 118
<211> LENGTH: 101
<212> TYPE: DNA
<213> ORGANISM: Homo sapiens

<400> SEQUENCE: 118
ccccaaatac cacatttgtt tgcaagtagg aataggactg tctgaggaat matttgagaa    60
actgagcaag tcactctctt tggcaacatg cagggccacc a                        101

<210> SEQ ID NO 119
<211> LENGTH: 101
<212> TYPE: DNA
<213> ORGANISM: Homo sapiens

<400> SEQUENCE: 119
ttgtgtgcca agctcagtgc tctcaaatat tctcccttca gcctagaaga sagactggta    60
cctgctgtaa ggggtctggc atggagagaa agccggcttc c                        101

<210> SEQ ID NO 120
<211> LENGTH: 101
<212> TYPE: DNA
<213> ORGANISM: Homo sapiens

<400> SEQUENCE: 120
tattttctac agcagatcac tcatctctta aatagattat gcattgatcg ycttcaaagg    60
gctaagcaca ctcaaaatat tctctaaagt cattctcatg c                       101

<210> SEQ ID NO 121
<211> LENGTH: 101
<212> TYPE: DNA
<213> ORGANISM: Homo sapiens

<400> SEQUENCE: 121
tccctagaaa gcaagtcaga cagggacaag tctatttttt aagagcccaa kaagaggaaa    60
tttcaaaatc tctattagcc atttaattgt tttacactat t                       101

<210> SEQ ID NO 122
<211> LENGTH: 101
<212> TYPE: DNA
<213> ORGANISM: Homo sapiens

<400> SEQUENCE: 122
catcattatc tgccagcctt ctctaatgtc tcccccatgg gctaaagaag ycttatttcc    60 tttactttc ccattaagtc ttcccttccg gcttttagt a                         101

<210> SEQ ID NO 123
<211> LENGTH: 101
<212> TYPE: DNA
<213> ORGANISM: Homo sapiens

<400> SEQUENCE: 123
tcagccttgt taggcaatgc ccctttcctt gttcatgttt ccttggagaa yaagtgatcc    60
tctcagcacg ctatcacttt atcattaaga atagaacttg a                       101

<210> SEQ ID NO 124
<211> LENGTH: 101
<212> TYPE: DNA
<213> ORGANISM: Homo sapiens

<400> SEQUENCE: 124
ttggttaata aatgaatcaa gctgactgca tgactaattc agattaatgg ygcagaaatc    60
agtcactaaa gaagccaaaa aaagtttgct ttaatagtct t                       101

<210> SEQ ID NO 125
<211> LENGTH: 101
<212> TYPE: DNA
<213> ORGANISM: Homo sapiens

<400> SEQUENCE: 125
gcttgacagt aagatttggt tcggaacatg agctcattca caaaagata kgggtaataa    60 gacgtctttt aaaaatatgg gtcaggcagc tttctcgtgt t                       101

<210> SEQ ID NO 126
<211> LENGTH: 101
<212> TYPE: DNA
<213> ORGANISM: Homo sapiens

<400> SEQUENCE: 126
cttcaagagt ctttgagatg cctataggct catctgttca ttacaagatg rtgaaatgga    60
gagcctgaaa gttaagagtc ttttccccca gtcaataact t                       101

<210> SEQ ID NO 127
<211> LENGTH: 101
<212> TYPE: DNA
<213> ORGANISM: Homo sapiens

<400> SEQUENCE: 127
cagatcttct gaagacctga gaaaggacag cagggtggag agacccctto rcaccttcca    60 gacgaaagca ctggcctgag gataggcttg cccaagggca a                       101

<210> SEQ ID NO 128
<211> LENGTH: 101
<212> TYPE: DNA
<213> ORGANISM: Homo sapiens

<400> SEQUENCE: 128
acccctagac aggaaaacat ccttcggggg gaaaaatgag gacatgaaat ygcttgctgc    60
ggtgcctatc attctgttaa ggacagtgaa aacacagtct g                       101

<210> SEQ ID NO 129
<211> LENGTH: 101
<212> TYPE: DNA
<213> ORGANISM: Homo sapiens

<400> SEQUENCE: 129
tattcagaat ccaaacatat agggatctca aataatcctt tcccttctat rcactactaa    60
ttagcttgat cgatatcatt aggaaattat tattataatc c                       101

<210> SEQ ID NO 130
<211> LENGTH: 101
<212> TYPE: DNA
<213> ORGANISM: Homo sapiens

<400> SEQUENCE: 130
acattaagac cggaggatat caacaaattt ggttgactga gccacatcct mtacctatct    60
gactcagtct atccacctgt gaaggagact ttaagaccta g                       101

<210> SEQ ID NO 131
<211> LENGTH: 101
<212> TYPE: DNA
<213> ORGANISM: Homo sapiens

<400> SEQUENCE: 131
tggtgaatga aaggcagtgc agagactgcc tctcttttttg aggatgtttg ytacagagcc    60
ttggtgtcag ataatcatgt aacaagcact ggattggcaa g                       101

<210> SEQ ID NO 132
<211> LENGTH: 101
<212> TYPE: DNA
<213> ORGANISM: Homo sapiens

<400> SEQUENCE: 132
ggattcattt tctgaagaat taagtcaaca gacatggctt cacaatgcac rtattggatt    60
ccttttgggg gtcagagcag actcagagct ctgagaggct t                       101

<210> SEQ ID NO 133

```
<211> LENGTH: 101
<212> TYPE: DNA
<213> ORGANISM: Homo sapiens

<400> SEQUENCE: 133
gagagcctca gcttcccagt tgcttgctgg accctaaagc tgtaagaact ytgtgaaact      60
tgaatgtttc ttttttaac caaggtaagg aatttaatgc c                          101

<210> SEQ ID NO 134
<211> LENGTH: 101
<212> TYPE: DNA
<213> ORGANISM: Homo sapiens

<400> SEQUENCE: 134
ggaggtacct tcatccttga aagagagac ttcagtatct gtggaacaag ygaagctaga       60
acttggcatc ggagcatagt gctgagcaaa gaagcctcta c                         101

<210> SEQ ID NO 135
<211> LENGTH: 101
<212> TYPE: DNA
<213> ORGANISM: Homo sapiens

<400> SEQUENCE: 135
tctcttaaac tccctccact caacacaact gataccttc attatctcct rtagtgtctg       60
tggcattggt attctaaagg agaaaactag aatctaatga g                         101

<210> SEQ ID NO 136
<211> LENGTH: 101
<212> TYPE: DNA
<213> ORGANISM: Homo sapiens

<400> SEQUENCE: 136
ttgttgtttt tgttgccacc acaagagcaa aggtatttcc tattttgttt raatttgtca     60
ctaagatcta aaacagtgga cacacaatgg gcacacaaca a                         101

<210> SEQ ID NO 137
<211> LENGTH: 101
<212> TYPE: DNA
<213> ORGANISM: Homo sapiens

<400> SEQUENCE: 137
atgcctccag gcttatgttc ttagtctaat actcagccct tagctcacaa yggaatcatc      60
aatcccagca actagatatt gggacaggga acctagagag t                         101

<210> SEQ ID NO 138
<211> LENGTH: 101
<212> TYPE: DNA
<213> ORGANISM: Homo sapiens

<400> SEQUENCE: 138
ttgataacct agtttagtat cctatgagtg ccttaaatac agaggatgct yaatgaaaat      60
ttattagact gcccgctcag cagctcactg ggattgaata t                         101

<210> SEQ ID NO 139
<211> LENGTH: 101
<212> TYPE: DNA
<213> ORGANISM: Homo sapiens

<400> SEQUENCE: 139
atctgcacat gccagtggtc tgaataacag aaggagtcct tccaaggcca ycctgacctg      60
```
cagccatgtt ggtgtaggaa ctgtctccag ggagccaaag t              101

<210> SEQ ID NO 140
<211> LENGTH: 101
<212> TYPE: DNA
<213> ORGANISM: Homo sapiens

<400> SEQUENCE: 140
ctagaaaata tccgtctctt gttctagcag ccataggtaa atgacaatgg mgacgctact     60
gaaaaatcac aactcgtgtg ttctaaaatg accacaaagg g                        101

<210> SEQ ID NO 141
<211> LENGTH: 101
<212> TYPE: DNA
<213> ORGANISM: Homo sapiens

<400> SEQUENCE: 141
acgcgtgtat gttttacaat atacatctct cataatatca actgaagcaa yatttaatgt    60
ttcagtctac cacagatcat ttattttcta gcaaatgtct t                        101

<210> SEQ ID NO 142
<211> LENGTH: 101
<212> TYPE: DNA
<213> ORGANISM: Homo sapiens

<400> SEQUENCE: 142
acatgtgagt tgaagttact ccatgaagcc cctaagaatg tgcagaaaag kgattgattc    60
aaatggatca ttctttcttt tccattacct ttttttttc c                         101

<210> SEQ ID NO 143
<211> LENGTH: 101
<212> TYPE: DNA
<213> ORGANISM: Homo sapiens

<400> SEQUENCE: 143
tggactgact tatataaaaa attagagaaa aatacaaatt agtacacatt ycaggacaaa    60
gttgtgtgat gcactaaggg aaatcgcatt agaaaagaga t                        101

<210> SEQ ID NO 144
<211> LENGTH: 101
<212> TYPE: DNA
<213> ORGANISM: Homo sapiens

<400> SEQUENCE: 144
tgaggaggaa gcaagaaaga agccaagatc cacagtggct gcttccaagt kgcatatgga    60
ctagttgctt gtggcaggga gagacatggg ttccgaaatc c                        101

<210> SEQ ID NO 145
<211> LENGTH: 101
<212> TYPE: DNA
<213> ORGANISM: Homo sapiens

<400> SEQUENCE: 145
aaatagagat aattcacgtg tactgttcaa caagcaatta ttcatatagt ytctcaagta    60
ctcaattcta accaagaaca tggtgtcctg tggtgtctac a                        101

<210> SEQ ID NO 146
<211> LENGTH: 101
<212> TYPE: DNA

<213> ORGANISM: Homo sapiens

<400> SEQUENCE: 146
gtaattctaa caaatggcta atggaagtga tatcaacacg tcaacataaa mgattaaaca        60
tctagaatgc cctgctaaga agatggctgg ggactgaact c                           101

<210> SEQ ID NO 147
<211> LENGTH: 101
<212> TYPE: DNA
<213> ORGANISM: Homo sapiens

<400> SEQUENCE: 147
gaaagaaggg tcattcacta cttaacagga aactagggtc cccagcaaag mgaagatatt        60
tatttcaagg aacctggaaa atggttccag aagtatggct a                           101

<210> SEQ ID NO 148
<211> LENGTH: 101
<212> TYPE: DNA
<213> ORGANISM: Homo sapiens

<400> SEQUENCE: 148
acaaaaagaa aaactgtaga ttcaccccgg cagagaggac taaacagatt racttttgat        60
atgagttggc tgcaggatag tgggccttt tcttcacgtt g                            101

<210> SEQ ID NO 149
<211> LENGTH: 101
<212> TYPE: DNA
<213> ORGANISM: Homo sapiens

<400> SEQUENCE: 149
ccctgtgccc tccacttacc ttcccaggag gcggcggcgg cacgggctgc rgcagaggtc        60
gaaggagtgg gactcaatgc gcaagcgcgg tccggctctt a                           101

<210> SEQ ID NO 150
<211> LENGTH: 101
<212> TYPE: DNA
<213> ORGANISM: Homo sapiens

<400> SEQUENCE: 150
ggtgagctcc ggaaaggctg ctagagggaa agcaggatgg gtcctccgag yccagcccca        60
ggagccgggt gtctccgttt ccgtcacttc ccagcactag g                           101

<210> SEQ ID NO 151
<211> LENGTH: 101
<212> TYPE: DNA
<213> ORGANISM: Homo sapiens

<400> SEQUENCE: 151
ttctggaggg ggcgggacca gagggcccaa ggagcgttac ttctgtaaac ycggagctgt        60
ggaagactgt gattggctgt cggctggagg agggcgcggg t                           101

<210> SEQ ID NO 152
<211> LENGTH: 101
<212> TYPE: DNA
<213> ORGANISM: Homo sapiens

<400> SEQUENCE: 152
ttctagctgg tgggccatga gctttattta ctctgcttcc aggaatacct yagctgttat        60
caataagcag tccttttctca agtttccatc tagtaccctt a                          101

<210> SEQ ID NO 153
<211> LENGTH: 101
<212> TYPE: DNA
<213> ORGANISM: Homo sapiens

<400> SEQUENCE: 153
cccctcttaa agagcttgat ctgccaacat tggagaaaag ggcaatccta yatatccatg    60
atcctgacat acctgcctca ggtaaactag gggagatact g                       101

<210> SEQ ID NO 154
<211> LENGTH: 101
<212> TYPE: DNA
<213> ORGANISM: Homo sapiens

<400> SEQUENCE: 154
tttccctcct cctatcccac catgggctgg attcttcatt tcacatccta yaaaaactca    60
gcataatttc caggtttgaa atggcaactt tctctctgtc t                       101

<210> SEQ ID NO 155
<211> LENGTH: 101
<212> TYPE: DNA
<213> ORGANISM: Homo sapiens

<400> SEQUENCE: 155
aaattgcatt tttcataatt tgttcataa atgaagtttc aagaatgtca ygctcagaaa     60
aatttggtaa ttcttgtggg gaaatgtgta actagccaaa g                       101

<210> SEQ ID NO 156
<211> LENGTH: 101
<212> TYPE: DNA
<213> ORGANISM: Homo sapiens

<400> SEQUENCE: 156
ataaatttgg gaaatgttga atgtgtaggc ttcatttcac aggacttttc rtgaccttaa    60
tgttatgtca attaaggatt cataacttta aaaaatgccc c                       101

<210> SEQ ID NO 157
<211> LENGTH: 101
<212> TYPE: DNA
<213> ORGANISM: Homo sapiens

<400> SEQUENCE: 157
atactttcta aagctcagtt gcactattga agaaaaagca gaatttcttg mcaaaagttt    60
cctgggtttt ttttcatcct aactctaaaa ttttacagaa t                       101

<210> SEQ ID NO 158
<211> LENGTH: 101
<212> TYPE: DNA
<213> ORGANISM: Homo sapiens

<400> SEQUENCE: 158
gaaggtaact gttaataatc caaacaaaag atgatgatgg tttgggctta mgtggtgtca    60
ctgaacacag acatagagga tgagattcag gtctgataaa a                       101

<210> SEQ ID NO 159
<211> LENGTH: 101
<212> TYPE: DNA
<213> ORGANISM: Homo sapiens

<400> SEQUENCE: 159
gcactccagc ctgagtgaca aagagaaaga ctgtccaaaa acaacaacaa maaaaaaaga    60
attacagtca ggtgcagtga ctcacgcctg taatcccaac a    101

<210> SEQ ID NO 160
<211> LENGTH: 101
<212> TYPE: DNA
<213> ORGANISM: Homo sapiens

<400> SEQUENCE: 160
ttaggttttc cctgtcccca gtaagcagat ctagttctct tttgctgttg yaggtttgcc    60
agttaattat tggattgtac tggactcaca ttcagagcat g    101

<210> SEQ ID NO 161
<211> LENGTH: 101
<212> TYPE: DNA
<213> ORGANISM: Homo sapiens

<400> SEQUENCE: 161
acaagataca gttatgtaaa tacctatgct taggtggcaa tctaaaactt rtttatatgt    60
gtttctttga ttgaaaactt ttgctttta atgccaatgc t    101

<210> SEQ ID NO 162
<211> LENGTH: 101
<212> TYPE: DNA
<213> ORGANISM: Homo sapiens

<400> SEQUENCE: 162
gaagcttaat ttctgctact cagagttaca tttgtatatt tttatgccta ycaaggattg    60
gaggcttctt agaagtgtat actgctcctt ctctccccat g    101

<210> SEQ ID NO 163
<211> LENGTH: 101
<212> TYPE: DNA
<213> ORGANISM: Homo sapiens

<400> SEQUENCE: 163
cttatttcag ttgcttttca taatagtact tattctatca gtttgacgga raaacaaagg    60
cttaggaaga ttcttagtaa aagcttcaaa tgtaagtatt a    101

<210> SEQ ID NO 164
<211> LENGTH: 101
<212> TYPE: DNA
<213> ORGANISM: Homo sapiens

<400> SEQUENCE: 164
attagaagca cagtctccat ttttaaagta gcagctcagt tcactctgac rgtatttcac    60
tgacgtagcc taaggctata ggtaatggaa cattactcac t    101

<210> SEQ ID NO 165
<211> LENGTH: 101
<212> TYPE: DNA
<213> ORGANISM: Homo sapiens

<400> SEQUENCE: 165
tcttatcaaa aaagaaggac attacaaaaa ggaaaaggca caattaacct ytaaaatgct    60
gaaaacaaaa gaatctcatt ctttgggaaa acatttagca g    101

```
<210> SEQ ID NO 166
<211> LENGTH: 101
<212> TYPE: DNA
<213> ORGANISM: Homo sapiens

<400> SEQUENCE: 166
acggaatctt ttaaattaaa aaatattgcc cattctgatg aaactgctta yaatgactac     60
aagtaaagat ggtggccatt aagtttatc gtgagcacct g                         101

<210> SEQ ID NO 167
<211> LENGTH: 101
<212> TYPE: DNA
<213> ORGANISM: Homo sapiens

<400> SEQUENCE: 167
ccagttttag cactgaaagt cctgcttcct aagaagaccc ctcagtcgtg rgaaaaccat     60
gacagttagt caccccaaca gttaagtaat ataaaacctg a                        101

<210> SEQ ID NO 168
<211> LENGTH: 101
<212> TYPE: DNA
<213> ORGANISM: Homo sapiens

<400> SEQUENCE: 168
ttatcagcag ctgggtggaa aaagaaaaa ttattcattt tcctaaaatc rgtaagaatg     60
caccagtatg ctgaggcaat acacagagta aaaagttaga a                        101

<210> SEQ ID NO 169
<211> LENGTH: 101
<212> TYPE: DNA
<213> ORGANISM: Homo sapiens

<400> SEQUENCE: 169
gtgggtttga ttcttgtcct agtctagcct cagttttggg caggcactgc kttggggtgg     60
ggctttctca aatatcctgc ccctttccca gtagcaggaa a                        101

<210> SEQ ID NO 170
<211> LENGTH: 101
<212> TYPE: DNA
<213> ORGANISM: Homo sapiens

<400> SEQUENCE: 170
atcctttctg tgtgtctcct cttgtggcta cacttgacgg gccatattat maaagaatac     60
aaaacaatag tacagacagg taaatgttta tgcctagaaa t                        101

<210> SEQ ID NO 171
<211> LENGTH: 101
<212> TYPE: DNA
<213> ORGANISM: Homo sapiens

<400> SEQUENCE: 171
tgttgttcat attttaaaaa aattcttagc cattatctct tcaaataaca ygtttgccaa     60
gttctcaata tgatattgtt ccatagatct tggatgctgt g                        101

<210> SEQ ID NO 172
<211> LENGTH: 101
<212> TYPE: DNA
```

-continued

```
<400> SEQUENCE: 172
tgtgtgtctt gcagcagctg gatgaaggtt ctgtaaatgt atgctacgtc kgttgagtcc    60
atggtgtagt ttaagtctga taatttttgt tgatttttt t                       101
```